(12) United States Patent
Allmendinger

(10) Patent No.: US 8,486,255 B2
(45) Date of Patent: Jul. 16, 2013

(54) SYSTEM, APPARATUS, AND METHOD FOR MEASURING AN ION CONCENTRATION OF A MEASURED FLUID

(75) Inventor: Klaus K. Allmendinger, San Juan Capistrano, CA (US)

(73) Assignee: EmiSense Technologies, LLC, Irvine, CA (US)

( * ) Notice: Subject to any disclaimer, the term of this patent is extended or adjusted under 35 U.S.C. 154(b) by 1335 days.

(21) Appl. No.: 12/134,832

(22) Filed: Jun. 6, 2008

(65) Prior Publication Data

US 2009/0145778 A1 Jun. 11, 2009

Related U.S. Application Data

(60) Continuation-in-part of application No. 11/767,629, filed on Jun. 25, 2007, now Pat. No. 8,029,656, which is a continuation-in-part of application No. 11/244,210, filed on Oct. 5, 2005, now Pat. No. 7,249,489, which is a division of application No. 10/699,182, filed on Nov. 1, 2003, now Pat. No. 6,978,655.

(60) Provisional application No. 60/443,628, filed on Jan. 30, 2003, provisional application No. 60/942,781, filed on Jun. 8, 2007.

(51) Int. Cl.
*G01N 27/02* (2006.01)

(52) U.S. Cl.
USPC ......... 205/783.5; 205/782; 205/781; 204/424

(58) Field of Classification Search
USPC ............... 204/424, 425; 205/781, 782, 783.5, 205/783; 73/23.31, 31.05
See application file for complete search history.

(56) References Cited

U.S. PATENT DOCUMENTS

| | | | |
|---|---|---|---|
| 6,623,618 B1 * | 9/2003 | Kato et al. | 205/781 |
| 2005/0077177 A1 * | 4/2005 | Sakayanagi | 204/425 |
| 2005/0098449 A1 * | 5/2005 | Ochs et al. | 205/781 |

* cited by examiner

*Primary Examiner* — Keith D. Hendricks
*Assistant Examiner* — Kourtney S Carlson
(74) *Attorney, Agent, or Firm* — Jeffrey T. Holman

(57) ABSTRACT

A primary pump current is directed through a primary electrochemical cell system between first and second constant primary pump currents to direct a first ion flow into and out from a shared measuring chamber. A first output signal generated by the primary electrochemical cell system in accordance with a first ion concentration within the shared measuring chamber is detected. A second output signal generated by a secondary electrochemical cell system in accordance with a second ion concentration within the shared measuring chamber is also detected. Based on a relationship between the first and second output signals, a secondary pump current is directed through the secondary electrochemical cell system between first and second constant secondary pump currents to direct a second ion flow into and out from the shared measuring chamber.

19 Claims, 21 Drawing Sheets

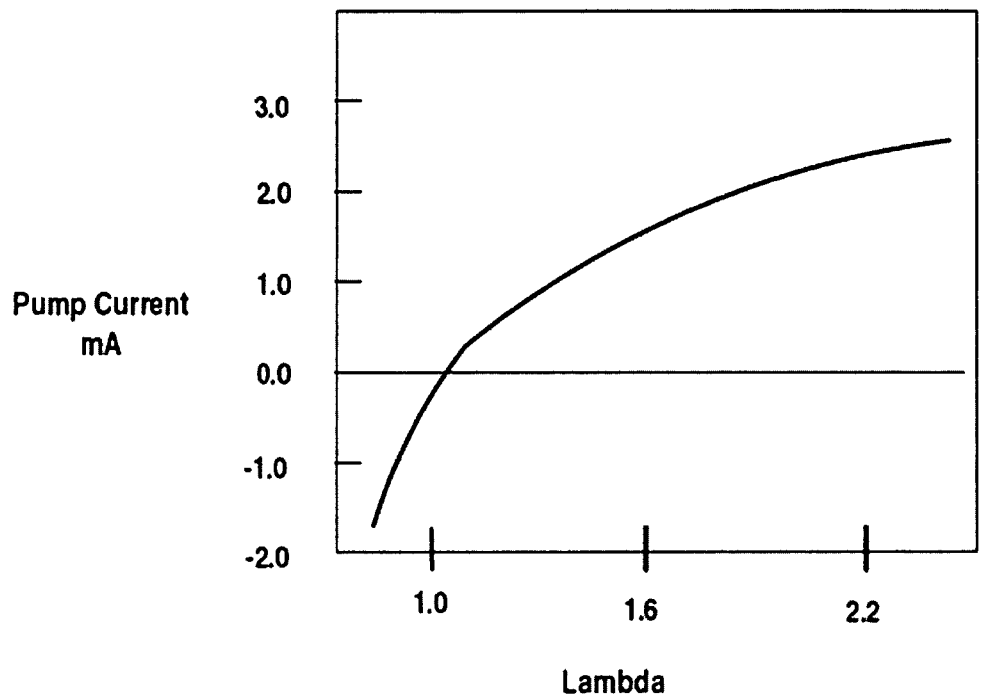
FIG. 1A *(PRIOR ART)*
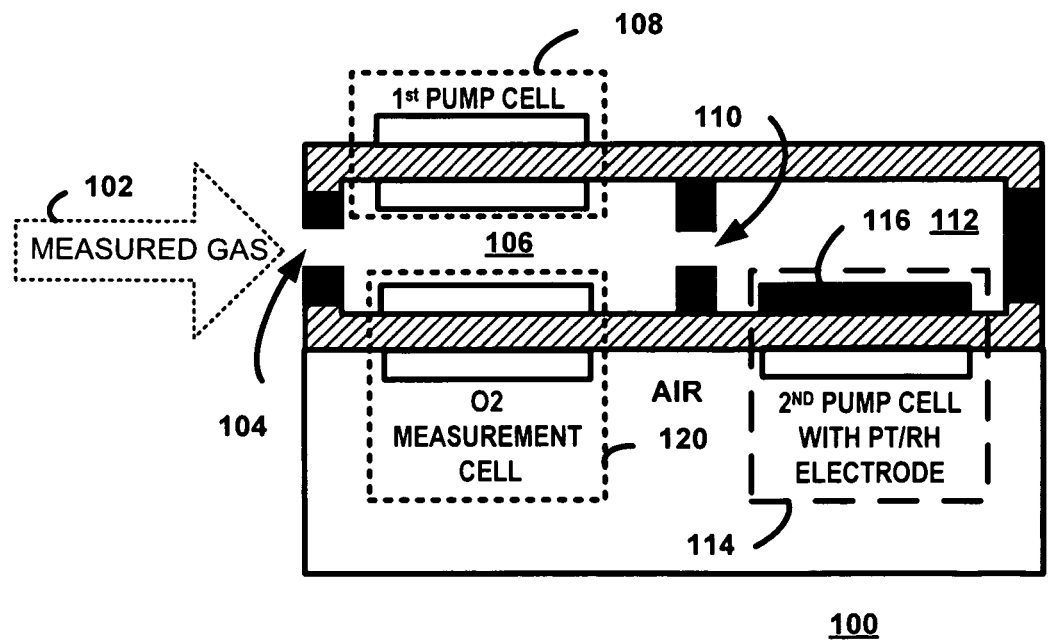
FIG. 1B *(PRIOR ART)*

SYSTEM, APPARATUS, AND METHOD FOR MEASURING AN ION CONCENTRATION OF A MEASURED FLUID

RELATED APPLICATIONS

This application is a continuation-in-part (CIP) patent application of U.S. patent application Ser. No. 11/767,629 entitled "System, Apparatus, And Method For Measuring An Ion Concentration Of A Fluid" filed on Jun. 25, 2007 now U.S. Pat. No. 8,029,656 which is a continuation-in-part (CIP) patent application of a U.S. patent application Ser. No. 11/244,210 entitled "System, Apparatus, And Method For Measuring An Oxygen Concentration Of A Gas" filed on Oct. 5, 2005, now U.S. Pat. No. 7,249,489 which is a divisional patent application of U.S. patent application Ser. No. 10/699,182, filed on Nov. 1, 2003, now U.S. Pat. No. 6,978,655, entitled "System, Apparatus, And Method For Measuring An Oxygen Concentration Of A Gas" which claims the benefit of priority of U.S. Provisional Application Ser. No. 60/443,628 filed on Jan. 30, 2003, entitled "System, Apparatus, And Method For Measuring An Oxygen Concentration Of A Gas", all hereby incorporated by reference in their entirety herein. This application also claims the benefit of priority of U.S. provisional application No. 60/942,781, entitled "Pulse Width Modulation Wideband Ion Sensor", filed Jun. 8, 2007 and incorporated by reference in its entirety herein. This application is also related to International application number PCT/US08/66090, entitled "System, Apparatus, And Method For Measuring An Ion Concentration Of A Fluid" filed on Jun. 6, 2008 and incorporated by reference in its entirety herein.

BACKGROUND

The invention relates in general to ion sensors and more specifically to an apparatus, system and method for monitoring an ion concentration of a measured fluid.

Wideband ion sensors are used to measure the concentration of particular ions within a fluid where the fluid may be a gas or liquid. A popular use of wideband gas ion sensors includes using oxygen sensors to determine on oxygen concentration within a gas mixture. Other examples of gas ion sensors include nitrogen sensors that sense gaseous oxides of nitrogen. Many conventional combustion engines utilize oxygen sensors for determining the air to fuel mixture of the exhaust of the combustion engine. Conventional internal combustion engines typically incorporate electronic fueling control using computing devices, such as Electronic Control Units (ECU), that meter fuel into the engine intake depending on engine intake airflow. Typically, the volume of fuel is regulated such that emissions are minimized and all of the fuel is completely burned. The theoretical ratio of air to fuel for complete combustion is 14.7 by weight for gasoline, called the stoichiometric ratio. Theoretically, all available fuel combines with all the intake air at the stoichiometric ratio. The unit Lambda ($\lambda$) is often used to represent the quotient of actual air to fuel ratio over the region near the stoichiometric ratio. Conventional electronic fueling systems typically include an oxygen sensor in the exhaust that measures the oxygen concentration of the exhaust. These oxygen sensors act as fuel cells that create an output voltage by combining unburned hydrocarbons in the exhaust with atmospheric oxygen. This results in a lambda/output transfer curve where a $\lambda$ of 1.0 corresponds to an output voltage of 0.45V. Using the oxygen sensor, the fueling control system regulates the fueling such that the resulting lambda is 1.0 at medium load conditions using a feedback loop. The transfer curve of a typical oxygen sensor is very steep where $\lambda$ is equal to 1.0, however, and significant variations in output voltage occurs for slight variations in $\lambda$. Accordingly, the measured voltage cannot be used to measure other $\lambda$ values. At high load conditions, a typical internal combustion engine produces maximum power at lambda values <one (0.75 to 0.85). Conventional ECU systems operate in an 'open loop' mode under these conditions where the volume of injected fuel is derived solely from pre-stored maps that relate intake air mass to fuel mass without feedback. Because engine aging and production variations change the actual air fuel ratio of the engine, these pre-stored conditions are not always correct for the particular engine. As a result, conventional systems are limited in that severe inefficiencies can occur at high load conditions. Many other wideband ions sensors experience similar drawbacks.

Some recent developments in engine technology have resulted in 'lean-burn' systems that operate at lambda ratios greater than 1 (up to 1.1) to minimize fuel consumption and further minimize emissions using special catalytic converters. Because ordinary lambda sensors are not usable in these lambda regimens, a 'wide-band' or Universal Exhaust Gas Oxygen (UEGO) sensor has been developed. UEGO sensors combine a small measuring chamber having an orifice open to the exhaust stream, a standard oxygen sensor (Nernst cell), and a pump cell. The pump cell is a solid-state device of porous ceramic that allows oxygen to move between the atmosphere and the measuring chamber. The direction and magnitude of the current through the pump cell (often referred to as the pump current) determines the direction and flow rate of oxygen ions. In conventional systems, an active feedback loop is incorporated such that the voltage at the oxygen sensor portion of the device is held at the stoichiometric voltage. The pump current can then be used to determine the $\lambda$ value over a wide range of ratios up to the ratio for free air.

FIG. 1A is graphical illustration of a typical relationship between the pump current and Lambda ($\lambda$). As shown in FIG. 1A, the resulting curve of pump current vs. lambda value ($\lambda$) is non-linear. Although the curve shape does not vary, manufacturing tolerances in the sensors result in different magnitudes of pump current vs. lambda ($\lambda$) (i.e. the curve shifts). Attempts to compensate for the variations include incorporating a calibration resistor in the connector to the measuring cell sensor. Unfortunately, this attempted solution does not address all of the variations. Barometric air pressure and exhaust pressure also influence the lambda/pump current relationship. Accordingly, the outputs of these sensors are not accurate. It is therefore desirable to have a measurement method for oxygen sensors that is self-calibrating and self-compensating for all the above variations.

The pump current vs. lambda curve is also highly temperature dependent. Typical UEGOs contain a heater element that maintains the sensor at the desired operating temperature. The temperature coefficient of the heater element is the quotient of change in resistance ($\Delta R$) to the change in temperature ($\Delta T$). Conventional techniques use the positive temperature coefficient of the heater element to regulate input by operating the element at a constant voltage. Because the temperature coefficient, $\Delta R/\Delta T$, is fairly small at the operating temperature, the resulting temperature regulation is not very precise. Depending on the sensor, the pump cell impedance, the Nernst cell impedance, or both have a much bigger temperature coefficient, $\Delta R/\Delta T$, and would, therefore, allow more precise temperature control. It would be more advantageous to control the temperature of the pump cell. Unfortunately, at lambda values near 1, the pump current is very small or equal to zero and the pump cell impedance can not be accurately measured on a low current. The Nernst cell is typically physically bonded to the pump cell and, therefore, the temperature of the Nernst cell and the pump cell differ by a small amount. In order to measure the Nernst cell impedance, a known fixed current or known fixed voltage have to be impressed on the Nernst cell and the resulting voltage or current then measured. Alternatively, a small alternating current (AC) voltage or current can be impressed on the Nernst cell and the resulting AC impedance measured. The first method requires stopping the lambda measurement for a period of time and also requires impressing the reverse charge on the Nernst cell to speed up recovery. The second method does not interfere with the measurement but requires low pass filters to remove the AC voltage or current from the measured signal. The filters also remove the higher signal frequencies which results in an inability to detect short transient responses. Both methods measure the temperature of the Nernst cell, not the pump cell. During operation, a temperature gradient between the pump cell and the Nernst cell may occur and some temperature control errors may result. Therefore there is a need for precise pump cell temperature control while measuring lambda without resorting to complicated circuitry to remove measurement artifacts.

Further, conventional fuel metering techniques result in significant pollution during the warm up period of the oxygen sensor. In conventional systems where UEGO sensors are used, a precise operating temperature must be attained before the UEGO output value is reliable. This increases the time the fuel injection system runs in 'open loop' without knowledge of actual air-fuel ratio. As a result, the time the engine creates uncontrolled warm-up pollution is dependent on the sensor warm-up time. Therefore, there also exists a need for an apparatus, system and method for measuring an oxygen concentration which minimizes the time before a reliable value is produced by the sensor.

Current wideband ion sensors such as wideband oxygen sensors (WBO2 sensors) combine a Nernst cell reference sensor and a pump cell in single package. A Nernst cell is an electrochemical cell that produces a voltage that is nonlinearly proportional to the difference in partial pressure of a measured gas between electrodes of the cell. In a typical oxygen sensor application, the electrodes are exposed to atmospheric air on an electrode on one side of a measuring chamber and to an exhaust gas of an internal combustion engine on the other electrode. A voltage is created by oxygen ions migrating through the solid electrolyte material of the cell. The pump cell is a Nernst cell where oxygen ion flow through the cell is forced by an electrical current. If the current flows in one direction, oxygen ions are transported from the outside air into the sensor. If the current is reversed to the other direction, oxygen ions are transported out of the sensor to the outside air. The magnitude of the current determines the number of oxygen ions that are transported each second.

The Nernst voltage is a voltage created as result of electrochemical reaction in the cell. The cell acts basically as a fuel cell. The Nernst voltage is created by the difference in oxygen partial pressure between the two electrodes of the cell. The Nernst equation describes it:

$$V\text{output} = (R^*)(T)/(n)(F) * \ln\left[(P_o,\text{air})/(P_o,\text{exh})\right]$$

where,

Voutput=O2 sensor's output voltage (0 to 1.0 volt is a typical range)

$R^*$=Universal Gas Constant=8.3143 [Joule/gram-mole*K]

T=Temperature of the exhaust gas [Deg K]

n=number of electrons involved in the reaction=4 in the NBO2 case

F=Faraday constant=96,480 [Coulomb/gram-mole]

Po, air=Partial pressure of O2 in the atmosphere [Pascals]

Po, exh=Partial pressure of O2 in the exhaust gas at temp [Pascals].

In conventional systems, both the Nernst cell and the pump cell are mounted in a very small measuring chamber open with an orifice (diffusion gap) to the exhaust gas. During a rich condition, there is little or no oxygen and relatively high levels of oxidizable combustion products within the measuring chamber. In rich conditions, the WBO2 controller regulates the pump cell current such that just enough oxygen ions are pumped into the chamber to consume all oxidizable combustion products. This action basically produces a stoichiometric condition in the measuring chamber. In the stoichiometric condition, the Nernst reference cell produces 0.45V. In a lean condition where there is excess oxygen, the controller reverses the pump current so that all oxygen ions are pumped out of the measuring chamber and a stoichiometric condition returns. The pump cell is strong enough to pump all oxygen out of the measuring chamber even if the chamber is filled with free air.

The task of the WB controller in conventional systems, therefore, is to regulate the pump current such that there is never any oxygen nor oxidizable combustion products in the measuring chamber. The required pump current is a measure of the Air/Fuel ratio. Conventional wideband sensors, however, are difficult to produce because multiple cells are combined in a small package. Also, the small orifice to exhaust gas is susceptible to contamination or blockage by exhaust particles limiting performance of the sensor. In addition, conventional wideband sensors exhibit a delay between Nernst reference cell output and changing pump cell current because of the physical separation between the two devices. Accordingly, an improved ion sensor is needed.

In addition, conventional oxides of Nitrogen (NOx) sensors are implemented using with a Zirconium oxide ($ZrO_2$) sensor. Conventional $ZrO_2$ sensors use Platinum (Pt) electrodes to detect the $O_2$ content of the gas to be measured. Pt electrodes do not have the capacity to measure NOx, because Nitrous oxide compounds are not disassociated by Platinum (Pt) alone. Alloys of Rhodium and Platinum, however, can be used to disassociate the nitrous oxide compounds. A sensor with an Yttrium stabilized zirconium-oxide electrolyte will produce an output voltage that is proportional to the difference in partial oxygen (O2) pressure between the electrodes if the sensor is operating at the appropriate temperature. When one electrode is exposed to air and the other electrode exposed to exhaust gas, the output voltage follows the Nernst relationship. When an electrical current is passed through a cell formed in this way, the cell acts as oxygen pump, where the oxygen current (in moles/second) is proportional to the electrical current. Sensors where the exhaust side electrode is constructed from a Pt—Rh alloy can also disassociate nitrous oxide compounds. Accordingly, the Nernst Voltage can be represented by:

$$V\text{output} = (R^*)(T)/(n)(F) * \ln\left[(P_o,\text{air})/((P_o,\text{exh}) + (P_n,\text{exh}))\right]$$

where,

Voutput=O2 sensor's output voltage (0 to 1.0 volt is normal range)

$R^*$=Universal Gas Constant=8.3143 [Joule/gram-mole*K]

T=Temperature of the exhaust gas [Deg K]

n=number of electrons involved in the reaction=4 in the NBO2 case

F=Faraday constant=96,480 [Coulomb/gram-mole]
Po, air=Partial pressure of $O_2$ in the atmosphere [Pascals]
Po, exh=Partial pressure of $O_2$ in the exhaust [Pascals]
Pn, exh=Partial pressure of NOx compounds in the exhaust [Pascals]

The NOx is decomposed at the Pt—Rh alloy electrode into N2 and O2 which causes a local increase in the O2 concentration at the Pt—Rh electrode. The local increase is represented by Pn. Accordingly, the partial pressure from NOx contributes to the relationship. Conventional NOx sensors, however, are limited in that when used in lean burn engines, such as diesel engines, the leftover partial pressure of $O_2$ in the exhaust is very high compared to the partial pressure of NOx compounds. For example, the leftover partial pressure of $O_2$ in the exhaust is typically in the single digit to multi digit percentage range while the partial pressure of NOx compounds is in the parts per million (ppm) range. Therefore, there is also a need for an ion sensor that extracts the NOx content of the exhaust independently to the $O_2$ content.

FIG. 1B is a block diagram of a conventional NOx sensor. The gas to be measured (measured gas) 102 is received through a primary diffusion gap 104 into a first measuring chamber 106. A first pump cell 108 pumps oxygen ions from the first measuring chamber 106 either to atmospheric air or to the surrounding exhaust gas until the remaining gas in the first measuring chamber 106 has a relatively low oxygen concentration. A portion of this oxygen-reduced gas diffuses through a secondary diffusion gap 110 into a secondary measuring chamber 112. A second pump cell 114 in the secondary measuring chamber 112 includes an electrode 116 consisting of a Platinum (Pt) and Rhodium (Rh) alloy exposed to the gas in the second measuring chamber 112. The Rhodium in this alloy has catalytic properties that disassociate the Nitrous Oxides (NOx) in the measurement gas within the second measuring chamber 112 into Nitrogen ($N_2$) and oxygen ($O_2$). As a result, the oxygen ($O_2$) concentration in the second measuring chamber 112 increases slightly. A constant voltage is applied to the secondary pump cell 114 and the current through that pump cell 114 is measured. The $NO_2$ content measurement is based on the current through the secondary pump cell 114. An oxygen measuring cell 120 provides the feedback for the pump cell to regulate the pump current in order to maintain a very low O2 concentration, while not allowing the concentration to decrease to the point where the voltage across the pump cell leads to electrolytic decomposition of the ZrO2 solid electrolyte destroys the pump cell. This conventional method, however, is limited in several ways. The measured current is relatively small (within the nano-Ampere range) and, as a result, is extremely susceptible to electromagnetic noise contamination. Further, such conventional sensors are difficult to manufacture due, at least partially, to multiple diffusion gaps. Also, the gas concentration differences between the first measuring chamber 106 and second measuring chamber 112 are very small. Accordingly, the diffusion flow through the second diffusion gap 110 is significantly delayed resulting in a very slow response time of the sensor.

Therefore, in addition to the needs described above for wideband and NOx sensors, there is a need for a NOx sensor that is easier to manufacture with increased performance.

BRIEF DESCRIPTION OF THE DRAWINGS

FIG. 1A is graphical representation of a relationship between pump current and an air to fuel ratio, Lambda (λ), for a typical Universal Exhaust Gas Oxygen (UEGO) sensor.

FIG. 1B is a block diagram of a conventional NOx sensor.

DETAILED DESCRIPTION

Figure 2A:
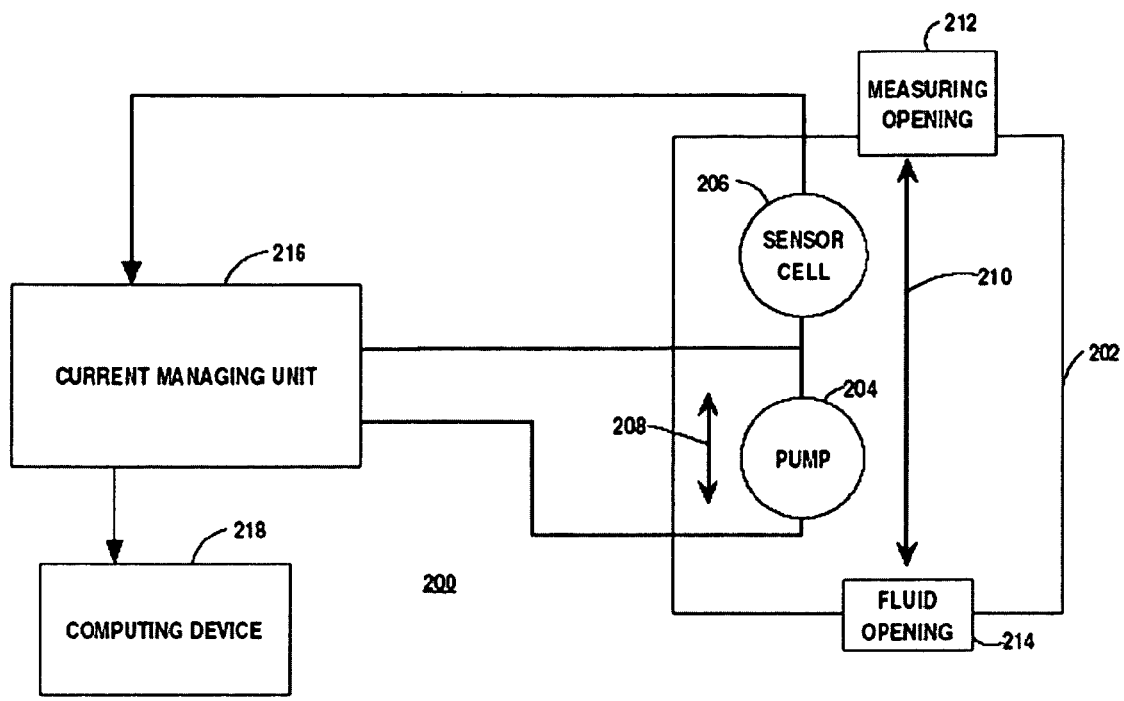
FIG. 2A is a block diagram of the oxygen monitoring device.

As explained above, conventional sensor systems are limited in several ways. These limitations are overcome in the exemplary embodiment which provides an efficient, low cost, accurate method for measuring an ion concentration of a fluid. An ion concentration of a fluid is measured by varying a pump current through a measuring cell based on an output of the measuring cell and observing the pulse width ratio of the resulting square wave representing the pump current. Further, in some circumstances, the method described herein allows the sensor to be used earlier in the warm-up period because the measurement method allows the application of a correction factor that compensates for the fact that the sensor has not yet achieved its desired operating temperature. Also, the embodiments allow precise pump cell temperature control while measuring lambda without resorting to complicated circuitry to remove measurement artifacts. In addition to determining oxygen ion concentrations, the embodiments can be used to determine other gas ion concentrations. For example, nitrogen sensors such as sensors that sense gaseous oxides of nitrogen (NOx) can be connected to a current managing device and a computer device to measure ion concentrations of gaseous oxides of nitrogen such as NO and $NO_2$ ion levels.

For some implementations, the functions of the pump cell and the sensor cell are performed by a measuring cell including a single electrochemical cell. A resistance voltage ($V_R$) resulting from the pump current and internal resistance of the cell is subtracted from the total voltage across the cell to determine the Nernst voltage of the cell. The Nernst voltage indicates an ion concentration of the measured fluid. Where the measuring cell is used to determine an oxygen concentration, thresholds for switching the pump current through the measuring cell are derived from the Nernst voltage. Where the measuring cell is used as part of a primary electrochemical system of a NOx measuring system, the Nernst voltage of the measuring cell is used as a reference to evaluate an output from a nitrogen sensitive cell and determine NOx.

In another NOX system embodiment, a pump cell and oxygen measuring cell form a primary electrochemical system that pumps oxygen into and out of a measuring chamber and provides a reference voltage that is compared to the output signal of a nitrogen sensitive electrochemical cell. A sensor managing device directs a primary pump current through the pump cell at a first constant primary pump current and a second constant primary pump current. The sensor managing device uses the difference between the first output signal from the measuring cell and the second output signal of the nitrogen sensitive cell to direct a secondary pump current through the nitrogen sensitive electrochemical cell at a first constant secondary pump current and a second constant secondary pump current. As described below, the nitrogen sensitive electrochemical cell reduces NOx to nitrogen and oxygen to create a local concentration of oxygen near the nitrogen sensitive electrochemical cell. The duty cycles of the direction of the secondary pump current or other related signals indicate the local concentration of oxygen and, therefore, the concentration of NOx.

In a sealed sensor embodiment, a measuring cell and compensation cell are positioned adjacent to a sealed chamber. The measuring cell and the compensation cell are electrically connected in series with opposite polarity such that ions pumped into sealed chamber by the measuring cell are pumped output of the sealed chamber at, or nearly at, the same rate.

As discussed herein, oxides of nitrogen (NOx) include compounds formed with nitrogen and oxygen. The compounds can be reduced into oxygen ions and nitrogen ions. Accordingly, NOx are examples of compounds formed from elements and that can be reduced into ions of the elements. For combustion engines, NOx primarily includes NO and $NO_2$ although other compounds may be present in some situations.

FIG. 2A is a block diagram of the ion monitoring device 200. The ion monitoring device 200 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

A measuring cell 202 includes at least a pump cell 204 and an ion sensor cell 206 where a magnitude and direction of a pump current 208 through the pump cell 204 is correlated to a flow of ions 210 within the measuring cell 202. A measuring opening 212 of the measuring cell 202 is positioned to receive a measured fluid while a fluid opening 214 faces an ambient fluid. The measured fluid and ambient fluid may be a gases or liquids. As discussed below, for example, the measured fluid is a measured gas and the ambient fluid is ambient air. The ion sensor cell 206 provides an output signal based on the number of ions within the measuring cell 202. In response to the output signal, a current managing unit 216 varies the pump current between two constant current levels. A first pump current is maintained by the current managing unit 216 until the output signal reaches a first threshold. When the first threshold is reached, the current managing unit 216 directs the pump current 208 in the opposite direction until the output signal reaches a second threshold level. A computing device 218 monitors the current fluctuation to determine an ion concentration of the measured fluid. As discussed below, a suitable application of the ion monitoring device 200 includes a gas ion monitoring device for monitoring exhaust gas from a combustion engine to determine oxygen concentrations for adjusting an air-fuel mixture. The ion monitoring device, method, and system may be implemented as part of any of several types of applications and systems and may be used to measure any of numerous types of ions within a fluid medium. Some examples include measuring ion concentrations of gaseous oxides of nitrogen such as NO and NO.sub.2 ion levels, measuring carbon dioxide levels, measuring gas ion concentrations in liquids such as oxygen and carbon dioxide concentrations in water. Further, ion concentrations of salts and elements such as lead within liquids or gases may be measured in some situations. Accordingly, any of numerous types of ion concentrations may be measured where the ion sensor and current pump are responsive to the particular ions that are measured. Further, as discussed below with reference to FIG. 20, FIG. 21 and FIG. 22, the measuring cell may be used as a primary electrochemical system of a NOx measuring system where the primary electrochemical system provides a first output signal that is used as a reference and compared to a second output signal of a nitrogen sensitive electrochemical cell to determine NOx concentrations.

After a calibration procedure is performed, the current managing unit 216 varies the current 208 through the pump cell 204 between a constant positive current (Ip) and a constant negative current (−Ip) based on the output signal of the ion measuring cell 206. When a negative current (−Ip) flows through the pump cell 204, ambient fluid is received through the fluid opening 214 into the measuring cell 202 through the pump circuit which results in an increase of the ion concentration within the measuring cell 202. At a high ion concentration of oxygen within the measuring cell 202, the ion measuring cell 206 provides a low voltage signal output. When an output signal lower threshold is reached, the current managing unit 216, directs a positive current (Ip) through the pump cell 204. When a positive current (Ip) flows through the pump cell 204, the ions in the measuring cell 202 flow out to the ambient fluid. As the positive pump current 208 (Ip) continues to flow, ions continue to flow out of the fluid opening 214. As a result, the ion concentration continues to decrease. The output signal continues to increase until an upper threshold is reached. In response to detecting that the upper threshold has been reached, the current managing unit 216 changes the direction of the pump current 208. Examples of suitable values for the threshold include values that maintain the ion measuring sensor 206 within a linear range or substantially linear range. Also, the threshold values may be the same value in some circumstances to sample the concentration with no hysteresis.

A square wave is formed between the positive and negative current levels. The duration of the pump current 208 at positive flow (Ip) and negative flow (−Ip) depends on the composition of the measured fluid. Accordingly, the computing device 218 compares the pulse width ratio ($PWM_{RATIO}$) of the resulting square wave to a known pulse width ratio function to determine the ion concentration of the measured fluid.

Figure 2B:
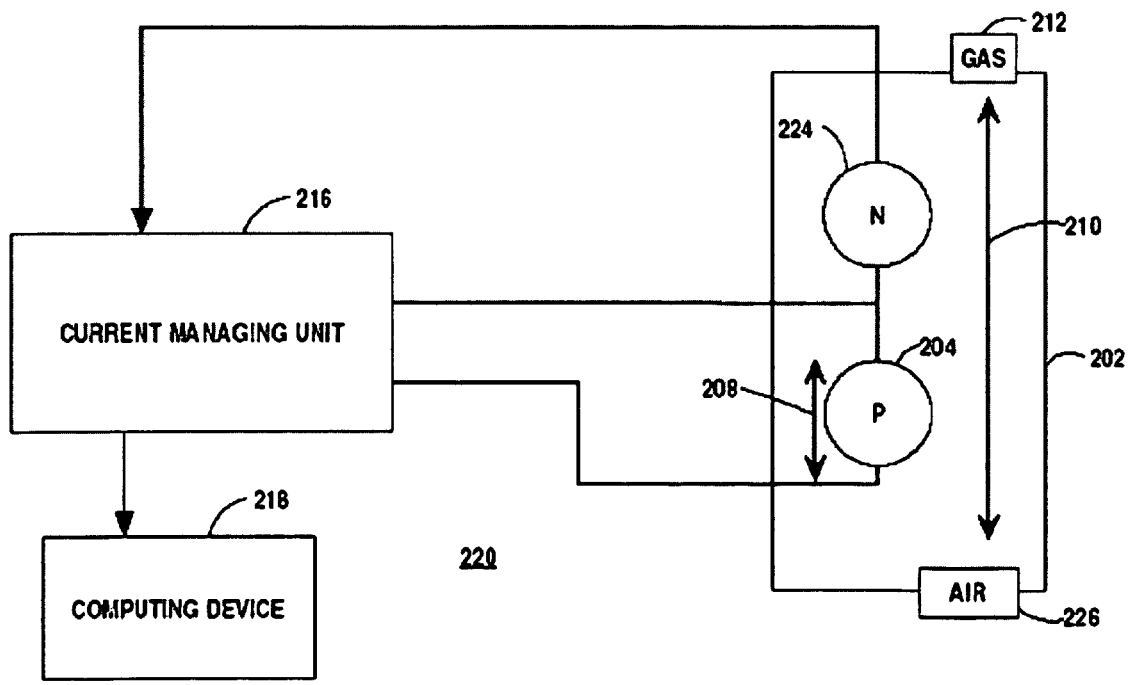
FIG. 2B is a block diagram of an ion monitoring device where the ion measuring device is a gas ion measuring device configured to measure an oxygen ion concentration within a measured gas.

FIG. 2B is a block diagram of an ion monitoring device 200 where the ion measuring device is a gas ion measuring device configured to measure oxygen ion concentration within a measured gas. The oxygen monitoring device 222 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

In the oxygen monitoring device 222, the pump cell 204 and the ion measuring cell 206 are responsive to oxygen ions. The ion measuring cell 206 is an oxygen measuring cell 224. The measuring cell 202 in the oxygen monitoring device 222, therefore, includes at least the pump cell 204 and an oxygen sensor cell 224 where a magnitude and direction of a pump current 208 through the pump cell 204 is correlated to a flow of oxygen ions 210 within the measuring cell 202. The measuring opening 212 of the measuring cell 202 is positioned to receive a measured gas while the fluid opening 214 is an air opening 226 that faces ambient air. The oxygen sensor cell 224 provides an output signal based on the number of oxygen ions within the measuring cell 202. In response to the output signal, the current managing unit 216 varies the pump current between two constant current levels. A first pump current is maintained by the current managing unit 216 until the output signal reaches a first threshold. When the first threshold is reached, the current managing unit 216 directs the pump current 208 in the opposite direction until the output signal reaches a second threshold level. The computing device 218 monitors the current fluctuation to determine an oxygen concentration of the measured gas. A suitable application of the oxygen monitoring device 222 includes monitoring exhaust gas from a combustion engine to determine oxygen concentrations for adjusting an air-fuel mixture. The oxygen monitoring device, method, and system may be implemented as part of any of several types of applications and systems. As discussed below, for example, the oxygen monitoring device 222 may be implemented as a hand-held diagnostic device, as an original equipment manufacturer (OEM) device within a vehicle, or as an aftermarket device for permanent installation in a vehicle. In addition to measuring oxygen, the oxygen measuring device and method may be used to measure the oxygen concentration of exhaled gases from a living being to determine the number of calories that are being expended. Accordingly, the device and method discussed with reference to FIG. 2B is only one example of the numerous applications of the measuring system.

For the embodiment described with reference to FIG. 2B, the oxygen sensor cell 224 is a Nernst cell (224) that is positioned adjacent to a pump cell 204 in accordance with known techniques. It is understood by those skilled in the art that although the following description refers to a Nernst cell (224), the invention may be implemented with other types of oxygen sensor cells 224 capable of providing an output signal based on the oxygen level in a measured gas. After a calibration procedure is performed in accordance with the procedure described below, the current managing unit 216 varies the current 208 through the pump cell 204 between a constant positive current (Ip) and a constant negative current (−Ip) based on the output signal of the Nernst cell (224). When a negative current (−Ip) flows through the pump cell 204, ambient air is received through the air opening 226 into the measuring cell 202 through the pump circuit which results in an increase of the concentration of oxygen within the measuring cell 202. At a high concentration of oxygen within the measuring cell 202, the Nernst cell (224) provides a low voltage signal output. When an output signal lower threshold is reached, the current managing unit 216, directs a positive current (Ip) through the pump cell 204. When a positive current (Ip) flows through the pump cell 204, the oxygen ions in the measuring cell 202 flow out to ambient air. Any unburned carbons or fuel within the measuring cell 202 combine with any remaining oxygen. As a result, the mixture of air and unburned carbons within the measuring cell 202 decreases in oxygen concentration and increases in fuel concentration. The output signal increases through the transition point where no unburned fuel and no excess oxygen are present in the measuring cell 202. At this transition point, lambda is equal to 1.0 and the Nernst cell (224) provides an output signal of approximately 450 mV. As the positive pump current 208 (Ip) continues to flow, oxygen ions continue to flow out of the air opening 214. As a result, the concentration of oxygen continues to decrease and the concentration of fuel increases in the measuring cell 202. The output signal continues to increase until an upper threshold is reached. In response to detecting that the upper threshold has been reached, the current managing unit 216 changes the direction of the pump current 208. For the embodiment of FIG. 2B, the upper threshold is 455 mV and the lower threshold is 445 mV. Other thresholds, however, can be used where some suitable values include values providing a range that includes the output signal for gas of ambient air and which maintain the Nernst cell (224) within a relatively linear potion of the lambda to voltage relationship. For example, another suitable pair of values includes 440 mV and 460 mV. In some cases, the lower and upper thresholds may be the same value.

As discussed above, a square wave is formed between the positive and negative current levels. The duration of the pump current 208 at positive flow (Ip) and negative flow (−Ip) depends on the composition of the measured gas. Accordingly, the computing device 218 compares the pulse width ratio ($PWM_{RATIO}$) of the resulting square wave to a known pulse width ratio function to determine the oxygen concentration of the measured gas.

Figure 3:
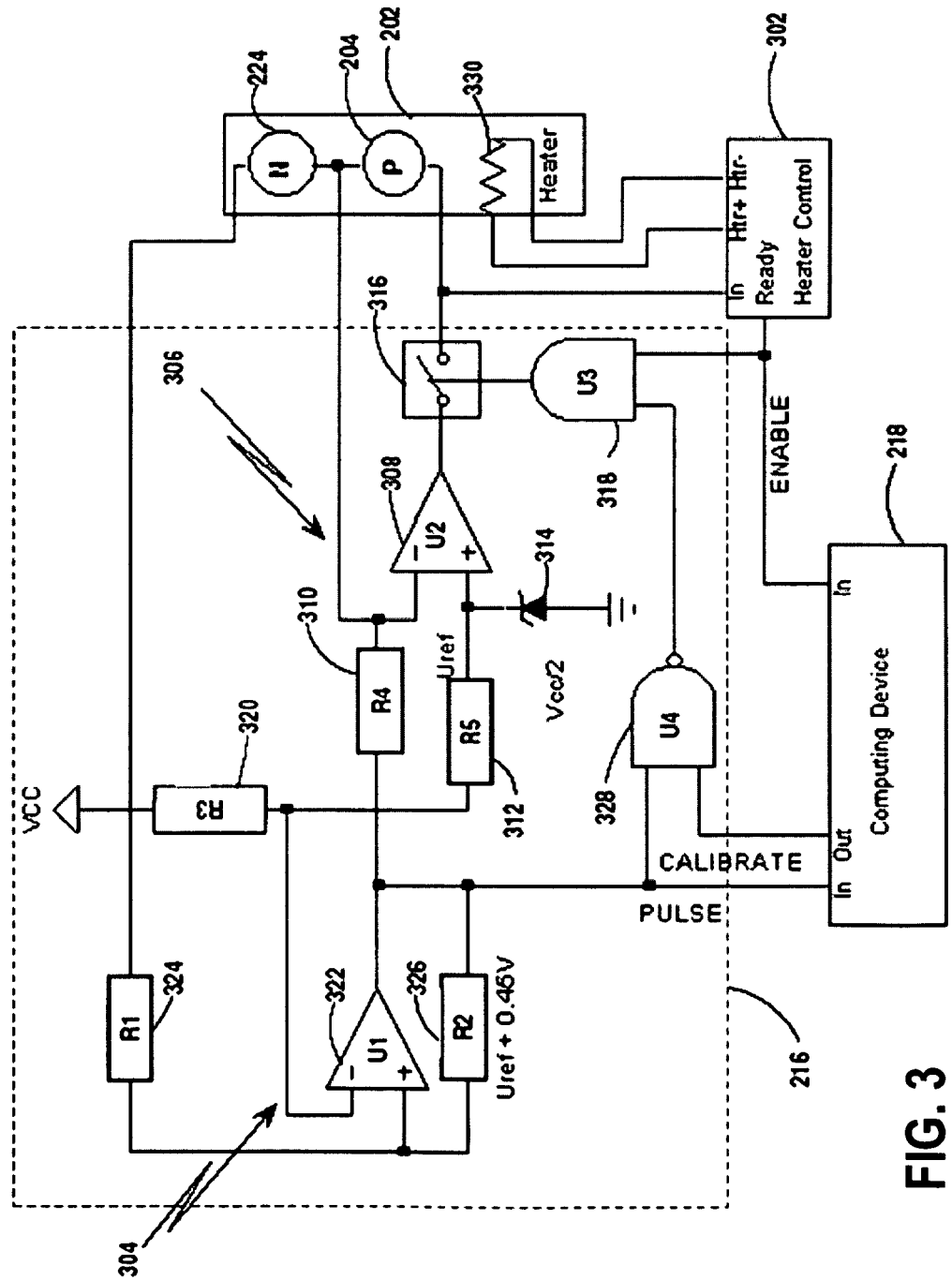
FIG. 3 is a schematic representation of the oxygen monitoring device where the current managing unit is implemented using an analog comparator circuit and an inverting amplifier circuit.

FIG. 3 is a schematic representation of the oxygen monitoring device 222 where the current managing unit 216 is implemented using an analog comparator circuit 304 and an inverting amplifier circuit 306. The current managing device 216 may be implemented using any combination and arrangement of hardware, software and firmware. For the example of FIG. 3, the current managing device 216 includes several hardware components including resistors, operational amplifiers, analog switches, Zener diodes, logic gates and other circuits. Those skilled in the art will recognize the various substitutions that can be made for one or more circuits or circuit elements by applying the teachings herein in accordance with known techniques. Further, the operating values may differ depending on the particular implementation of the current managing device 216. Although the discussion with reference to FIG. 3 is directed to oxygen sensors, the teachings can be applied to other types of wideband sensors.

The inverting amplifier circuit 306 at least includes an operational amplifier ($U_2$) 308, an inverting input resistor ($R_4$) 310, and a non-inverting input resistor ($R_5$) 312. The voltage at the non-inverting input of the operational amplifier ($U_2$) 308 is maintained at voltage of $U_{REF}$ by a Zener diode 314. $U_{REF}$ is equal to Vcc/2 which is approximately 2.5 volts for this example. The pump cell 204 in the measuring cell 202 is connected through an analog switch 316 between the output of the operational amplifier ($U_2$) 308 and the inverting input of the operational amplifier ($U_2$). The operational amplifier ($U_2$) 308, inverting input resistor ($R_4$) 310 and the pump cell 204 impedance ($R_{pump}$) form the inverting amplifier 306 with a gain of $-R_{pump}/R_4$. The output of the operational amplifier ($U_2$) 308 is connected to the analog switch 316 that connects the output of the operational amplifier 308 to the pump cell 204 in response to the output level of an AND gate ($U_3$) 318. Since the AND gate 318 provides an active "high" output when the heater control unit 302 presents a "high" enable signal, the analog switch 316 prevents current from flowing through measuring cell 202 during warm up. Further, as explained below, during the calibrate procedure, the analog switch 316 is opened during the negative pump current 208 cycle resulting in a pump current 208 that alternates between a positive pump current (IP) and zero.

The inverting input of the operational amplifier ($U_2$) 308 is connected to the output of the analog comparator circuit 304 through the inverting input resistor ($R_4$) 310. The non-inverting input resistor ($R_5$) 312, a supply resistor ($R_3$) 320 and the Zener diode 314 form a voltage divider and present a reference voltage of (Vcc/2+0.45V) to the inverting input of an operational amplifier ($U_1$) 322 of the analog comparator circuit 304. For the example described with reference FIG. 3, the reference voltage is 2.95 Volts since Vcc is 5 Volts. The positive input of the operational amplifier 322 is connected to the output of the Nernst cell (224) through a sensing resistor ($R_1$) 324. A feedback resistor ($R_2$) 326 provides a voltage equal to $U_{REF}$+0.45V to the positive input of the operational amplifier 322. Therefore, the operational amplifier ($U_1$) 322, the resistor ($R_1$) 324, and the feedback resistor ($R_2$) 326 form the analog comparator circuit 304 operating with a hysteresis voltage of approximately 10 mV.

The analog comparator circuit 304, the inverting amplifier circuit 306 and the measuring cell 202 form an oscillator with a variable pulse width modulation (PWM) ratio and a frequency that is dependent on the response time of the measuring cell 202. The pump current 208 alternates between +Vcc/(2*R4) and −Vcc/(2*R4). The computing device 218 measures the times the output of U2 spends above ($t_1$) and below Vcc/2 ($t_2$) and from that calculates the $PWM_{RATIO}$ and λ according to the function described below. Lambda (λ) is calculated at every transition of the output of the comparator for the examples, herein. The Nernst cell (224) provides an output signal approximately between 0.1 V and 0.7 V and the resulting (λ) measurement frequency is about 7 octaves higher than the 3 dB point of the response frequency of the oxygen sensor cell 206. Accordingly, the oxygen sensor cell 224 response frequency is well above the Nyquist frequency for the examples discussed herein.

For the example of FIG. 3, the heater control unit 302 increases the temperature of the measuring cell 202 using a sensor specific method and ramp-up schedule. After the measuring cell 202 has achieved its operating temperature, the "Ready" output of the heater control unit 302 goes active providing a high ENABLE signal to the AND gate ($U_3$) which closes the analog switch 304. The enable signal is also connected to an input of the computing device 218 and indicates to the computing device 218 that the measuring cell 202 is ready for operation. The heater control unit 302 then maintains a constant predetermined voltage over the heater element or uses other (sensor specific) methods for temperature regulation. For the example discussed with reference to FIG. 3, the pump cell impedance is measured when the heater element 330 impedance is at the minimum value. The pump cell impedance is maintained at the measured value by continually monitoring the pump cell impedance and adjusting the temperature with the heater element 330.

As described below with reference to FIG. 6, the computing device 218 stores values in non-volatile memory corresponding to the PWM ratio at the stoichiometric ratio ($PWM_{ST}$) and the pulse width ratio for air ($PWM_{AIR}$). In the examples described below with reference to FIGS. 4-8, a nominal lambda value having an error on the order of +/−5% is calculated based on the calibration values and the measured $PWM_{RATIO}$. Because $PWM_{ST}$ is dependent on the characteristics and age of the sensor much more than on environmental conditions, the calibration process does not need to be performed very often in most circumstances.

Based on these teachings, those skilled in the art will recognize the various components, devices, and circuits elements that can be used in the measuring device. An example of suitable device that can be used for the operational amplifiers 308, 322 include the TLV2463 operational amplifier available from the Texas Instruments company. Values for the inverting resistor ($R_4$) 310 and the non-inverting ($R_5$) resistor 312 are on the order of a few hundred ohms. An example of suitable computing device 218 includes an 850 Family RISC 8-Bit Microcontroller. In some circumstances, some or all of the functional blocks described above may be implemented as an application specific integrated circuit (ASIC). For example, heater control and current managing unit 216 and computing device 218 can be easily integrated into a mixed signal ASIC with very few external parts.

Figure 4:
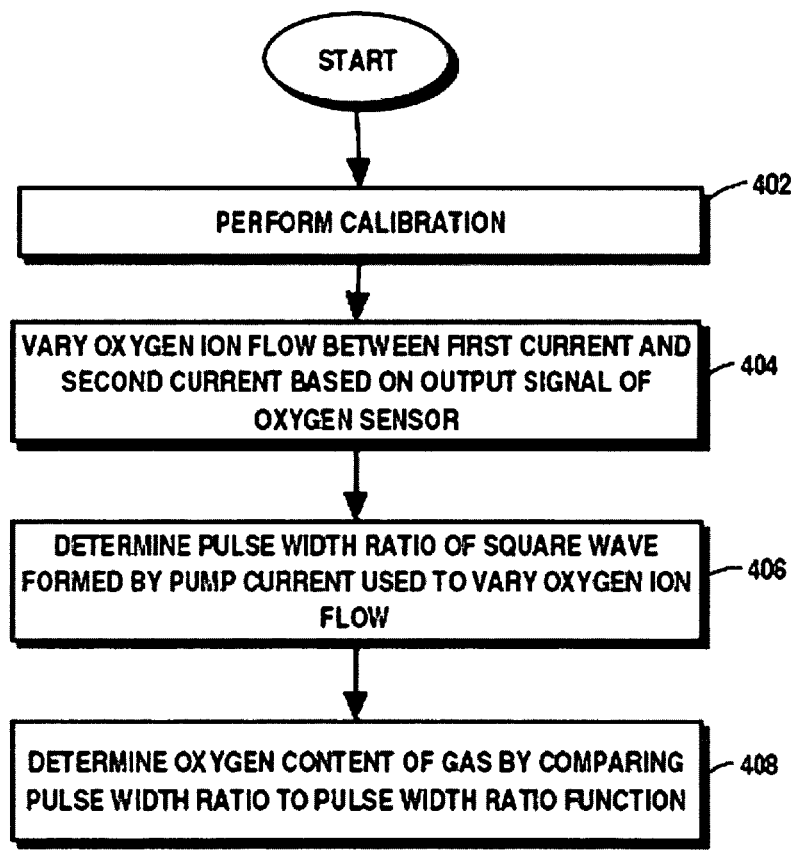
FIG. 4 is a flow chart of a method of measuring an oxygen concentration of a gas.

FIG. 4 is a flow chart of a method of measuring an oxygen concentration of a gas. The method may be performed with any combination of hardware, software or firmware. For this example, the method is performed in the oxygen measuring device 222. Although the discussion with reference to FIG. 4 is directed to oxygen sensors, the teachings can be applied to other types of wideband sensors.

At step 402, a calibration procedure is performed. The calibration procedure obtains the calibration values for initializing the oxygen measuring device and may include values related to the characteristics of the particular measuring cell 202 or related to environmental conditions. As explained below with reference to the example of FIG. 6, values are obtained for maintaining the pump cell 204 impedance, for establishing the pulse width ratio function for calculating lambda, and for adjusting the lambda value when the PWM ratio for a stoichiometric ratio ($PWM_{ST}$) is not zero. Other calibration values may include parameters related to the frequency of a square wave of the pump current 208 reflecting oxygen sensor characteristics.

At step 404, the oxygen ion flow is varied between a first pump current and a second pump current based on the output signal of the oxygen sensor cell 224. In this example, the ion flow is varied by alternating the pump current 208 between a positive constant current (IP+) and a negative constant current (IP−). The analog switch 316 remains closed during the measurement procedure.

At step 406, the pulse width ratio ($PWM_{RATIO}$) of the square wave formed by the pump current 208 is determined by the computing device 218. In this example, the pulse widths ($t_1$ and $t_2$) of the square wave formed by the varying pump current 208 are measured using a crystal clock in the computing device 218. Although individual values of a single pulse can be measured and stored, the duration of the pulses resulting from the varying current are averaged over a time period.

At step 408, the pulse width ratio ($PWM_{RATIO}$) is compared to the pulse width ratio function to determine the oxygen concentration of the measured gas. In this example, the computing device 218 applies the measured values to equations that utilize the calibrated values.

Figure 5:
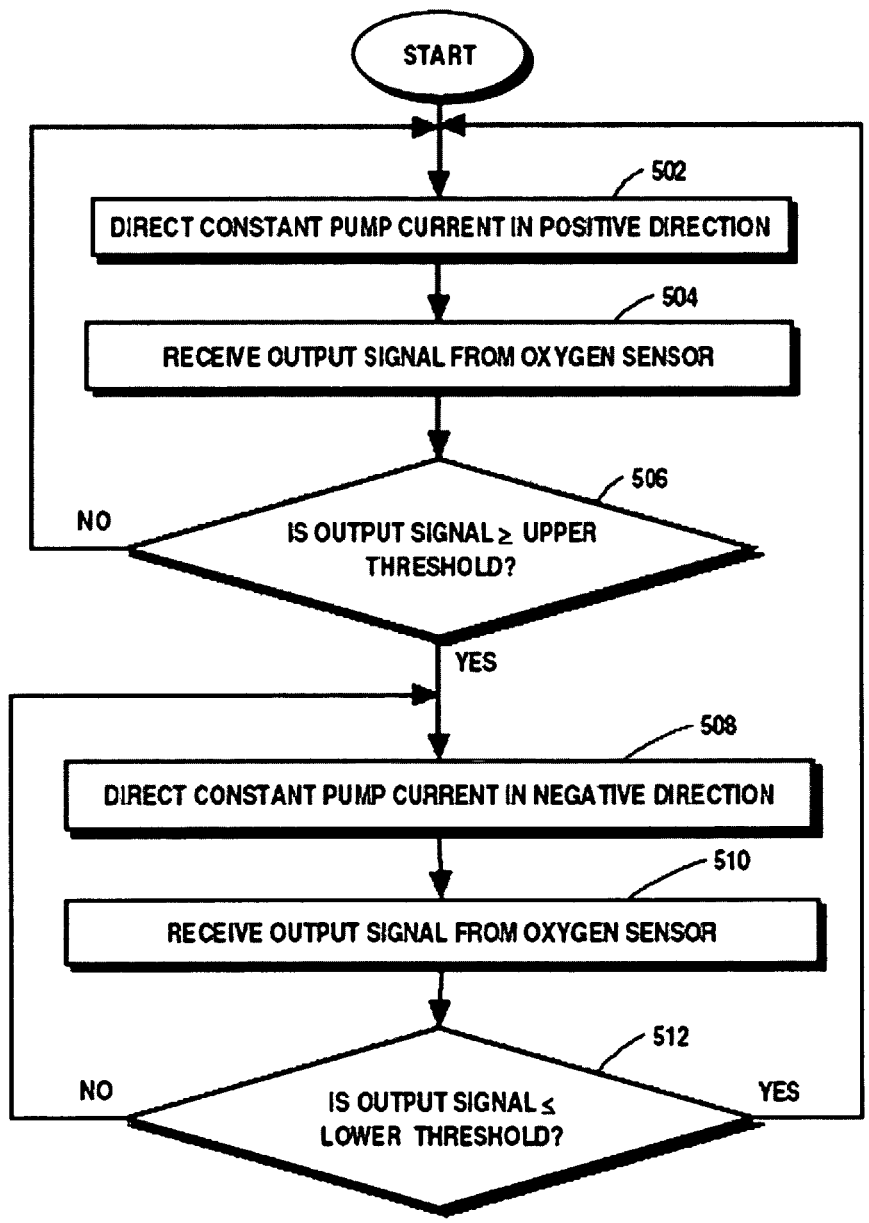
FIG. 5 is a flow chart of a method of varying the oxygen ion flow within the measuring cell.

FIG. 5 is a flow chart of a method of varying the oxygen ion flow within the measuring cell 202. The flow chart of FIG. 5, therefore, illustrates an exemplary method of performing step 404 of FIG. 4. Although the discussion with reference to FIG. 5 is directed to oxygen sensors, the teachings can be applied to other types of wideband sensors.

At step 502, the pump current 208 is directed in a positive direction through the pump cell 204 at a constant magnitude. In the oxygen monitoring device 200 described with reference to FIG. 3, the analog switch 316 remains closed as positive voltage is applied across the pump cell 204. The positive voltage is maintained until the analog comparator circuit 304 triggers the inverting amplifier 308 to applying a negative voltage across the pump cell 204.

At step 504, the output signal from the oxygen sensor cell 224 is received. In the exemplary oxygen monitoring device 200, the output of the oxygen sensor cell 224 is received through the resistor ($R_1$) 324 at the positive input of the operational amplifier 322 of the analog comparator circuit 304.

At step 506, it is determined whether the output signal is greater than or equal to the upper threshold. If the upper threshold has not been reached, the method returns to step 502 where the constant positive pump current is directed through the pump cell 204. If the upper threshold has been reached, the method continues at step 508 where the current is reversed and a constant pump current 208 is directed in the negative direction. As discussed above with reference to example of FIG. 3, the current managing device 216 includes an analog comparator circuit 304 and an inverting amplifier circuit 306 to provide the constant current until the thresholds are reached. The analog comparator circuit 304 triggers the reverse of the pump current 208 in response to the detection that the thresholds have been reached. Therefore, the positive pump current (IP+) is maintained until the output of the oxygen sensor cell 224 reaches an upper threshold that causes the output of the analog comparator circuit 304 to switch to a high output changing the output of the inverting amplifier circuit 306.

At step 508, the pump current 208 is directed in a negative direction. In response to the reversed voltage output of the inverting amplifier circuit 306 the pump current 208 reverses direction and becomes negative (−Ip).

At step 510, the current managing unit 216 receives the output signal from the oxygen sensor cell 224. In the exemplary oxygen monitoring device 222, the output of the oxygen sensor cell 224 is received through the resistor ($R_1$) 324 at the positive input of the operational amplifier 322 of the analog comparator circuit 304.

At step 512, it is determined if the output signal is less than or equal to the lower threshold. Of the lower threshold has not yet been reached, the method returns to step 508 where the current managing unit 218 continues to direct the pump current 208 in a negative direction through the pump cell 204. Otherwise, the procedure returns to step 502, where the current is reversed to the positive direction. Accordingly, in this example, the current managing device 216 varies the current between 0.445 volts and 455 volts based on the output of the oxygen sensor cell 224. As the pump current 208 is varied, characteristics of the resulting square wave are measured and stored.

For the examples discussed herein, the computing device 218 monitors the time periods ($t_1$ and $t_2$) and if either of the time periods exceeds an operating threshold, the computing device 218 overwrites the ENABLE signal and disconnects the pump cell 204 to prevent damage to the sensor. A diagnostic procedure is performed to determine the fault condition.

Figure 6:
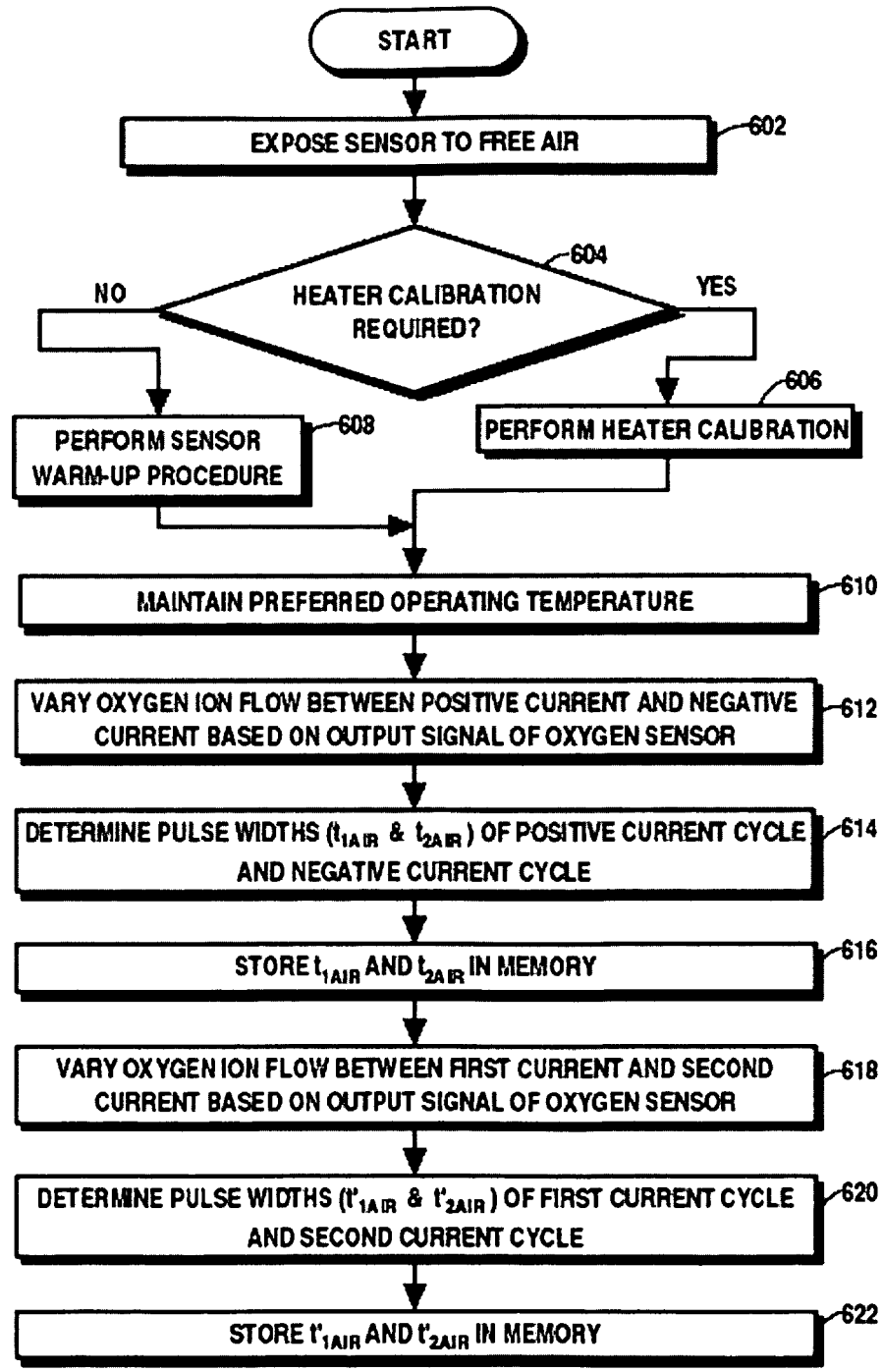
FIG. 6 is a flow chart of a method of calibrating an oxygen measuring device.

FIG. 6 is a flow chart of a method of calibrating the oxygen monitoring device 222. The method described with reference to FIG. 6 provides an example of a method of performing the calibration step 402 of FIG. 4. The oxygen monitoring device 222 may be calibrated in any number of ways and the particular calibration method used may depend on a variety of factors such as the characteristics of the particular sensor 202 and the data that will be collected using the oxygen monitoring device 222. In this example, the calibration procedure includes calibrating the heater control unit 302 and determining the pulse widths of the varying pump current 208 when the oxygen sensor cell 224 is exposed to free air. Although the discussion with reference to FIG. 6 is directed to oxygen sensors, the teachings can be applied to other types of wideband sensors.

At step 602, the oxygen sensor cell 224 is exposed to free air. In this example, the measuring cell 202 is placed in an area where exposure to exhaust gases or other air borne impurities is minimized. In some circumstances where the oxygen measuring device 222 is operating in a functioning vehicle, the computing unit determines that the engine is in a coast down mode when the resulting lambda value is above the lean burn limit for gasoline and not changing over some period of time. When it is determined that the vehicle is in a coast down mode, the computing device 218 performs the calibration procedure. If the computing device 218 is the ECU itself, the coast down condition is already known and the ECU, after the predetermined purge time of the exhaust system, performs the calibration procedure for free air.

At step 604, it is determined whether the heater control unit 302 should be calibrated. In this example, the heater control unit 302 is calibrated during the powering up sequence. Examples of other suitable situations that require the heater calibration procedure to be performed include the replacement or reconnection of the measuring cell 202 and the detection of certain measurement errors. If heater calibration is required, the procedure continues at step 606. Otherwise, the proceeds directly to step 608.

At step 606, the heater control unit 302 is calibrated. In this example, a preferred heater impedance and a preferred pump cell impedance corresponding to a preferred operating temperature of the Nernst cell (224) are stored in memory. As discussed with reference to FIG. 8, the Nernst cell impedance is maintained at a target Nernst cell impedance for a suitable time period before the preferred heater impedance and the preferred pump cell impedance are measured and recorded.

At step 608, a sensor warm-up procedure is performed. In the monitoring device described with reference to FIG. 3, the analog switch 316 is initially opened during the sensor warm-up procedure. In accordance with the appropriate heating timetable, power is applied to the heater element 330 to increase the temperature. The heater control unit 302 monitors the current and voltage across the heating element 330 and determines the impedance of the heater element 330. The heater impedance is compared to the preferred heater impedance that was measured and stored during the heater calibration procedure. When the heater control unit detects that the heater impedance is equal to the preferred heater impedance, the heater control unit 302 determines that the minimum operating temperature of the oxygen sensor cell 206 has been reached. In response to a determination that the desired operating temperature is reached, the heater control unit 302 presents a "high" enable signal at the "Ready" output. The AND gate (U3) 318 closes the analog switch 316 when the ENABLE signal goes "high".

At step 610, the preferred operating temperature of the Nernst cell is maintained. The preferred operating temperature is maintained during the remainder of the oxygen sensor calibration procedure as well as during operation of the oxygen monitoring device 222. For the examples discussed herein, the pump cell 204 impedance $R_{PUMP}$ is constantly monitored during operation and the heater control unit 302 is controlled to maintain a constant, or nearly constant, preferred pump cell impedance. The preferred pump cell impedance is retrieved from memory where it was stored during the heater calibration procedure. An example of a suitable method of controlling the heater control unit 302 includes using pulse width modulation to increase or decrease the amount of power dissipated by the heater element 330.

When the oxygen measuring device 222 is in an oscillating mode and the current is varied, the voltage at the pump cell 204 (output of $U_2$) is determined by Vcc, $R_{PUMP}$, the resistor $R_4$ 310, and the back-EMF of the pump cell 204. The output of the operational amplifier ($U_1$) 322 of the analog comparator circuit 304 switches between 0V and Vcc. The heater control unit 302 samples the output of the operational amplifier ($U_2$) 308 before and after each transition of the output of the operational amplifier ($U_1$) 322. The absolute value of the difference between the voltage measured before and after each transition is $U_{DIFF}$. In some circumstances, the output of the operational amplifier ($U_2$) 308 is passed through a high pass filter (not shown) of sufficiently high cut-off frequency. The filter output is sampled immediately after the transition point and the absolute value of resulting output voltage is equal to $U_{DIFF}$.

The heater control unit 302 calculates the pump cell 204 impedance $R_{PUMP}$ in accordance with the following relationship:

$$R_{PUMP}=R_4(U_{DIFF}/Vcc) \qquad (1)$$

In some circumstances, the Nernst cell (224) impedance ($R_N$) is monitored as an alternative or in addition to monitoring the pump cell 204 impedance. In order to monitor the Nernst cell (224) impedance, the output voltage signal of the Nernst cell (224) is passed through a high pass filter and amplifier (not shown). The resulting filtered and amplified signal is then sampled at the comparator transition point. The peak-peak voltage, $U_{NPP}$, is then calculated as the difference between the sample voltage at low-high and high-low transition.

The voltage $U_{NPP}$ follows the equation:

$$U_{NPP}=Vcc(R_1+2R_N)/R_2 \qquad (2)$$

$U_{NPP}$, therefore, linearly follows the Nernst cell (224) impedance, $R_N$, and is a convenient measurement for the Nernst cell (224) impedance without the use of any filtering in the signal path to influence the measured lambda signal. The resistors, $R_1$ and $R_2$, are chosen such that the current through $R_N$ is small enough to not influence the function of the Nernst cell (224) and such that the $U_{NPP}$ at the Nernst operating temperature and impedance is approximately 10 mV.

At step 612, the oxygen ion flow 210 is varied between a positive current (Ip) and the negative current (−Ip) based on the output signal of the oxygen sensor cell 224. An example of suitable method of varying the current 208 is described above with reference to FIG. 5.

At step 614, the pulse width ratio for air ($PWM_{AIR}$) is determined. For these examples, the pulse widths ($t_{1AIR}$ and $t_{2AIR}$) are determined for the positive current cycle and the negative current cycle. The transition times of the square wave are timed by a crystal clock within the computing device 218 to measure the pulse widths. The values for the pulse widths are measure and averaged over a sufficient time period such as one second, for example, to calculate an average $PWM_{AIR}$.

If the pulse width ratio for air is calculated during a coast down condition, the computing device 218 determines when the condition is reached before measuring the pulse widths of the pump current 208. If the computing device 218 is an ECU in the system, the ECU detects the condition based on parameters directly available to the ECU such as throttle position and engine speed.

At step 616, $PWM_{AIR}$ is stored in memory. Various techniques may be used to store and retrieve calibration information. For example, the pulse widths ($t_{1AIR}$ and $t_{2AIR}$) may be stored directly into memory and used for calculating $PWM_{AIR}$ at a later time. Such a procedure may be desired where the frequency of the square wave is used to further compensate for pressure and temperature variations. By storing the pulse width timing, frequency information is stored in addition to the average pulse width ratio for air ($PWM_{AIR}$).

At step 618, the oxygen ion flow 210 is varied between a first current and second current based on the output signal of the oxygen sensor cell 206. For the examples discussed herein, the current 208 is varied between (IP) and zero. In a manner similar to the method described above, the current 208 is varied from a first current to a second current except that a zero current is used in place of the negative current (IP−).

At step 620, the pulse width ratio for air when the second current is zero ($PWM'_{AIR}$) is determined. For the examples discussed herein, the pulse widths ($t'_{1AIR}$ and $t'_{2AIR}$) are determined for the positive current cycle and the zero current cycle. The transition times of the square wave are timed by a crystal clock within the computing device 218 to measure the pulse widths. The values for the pulse widths are measure and averaged over a sufficient time period such as one second for example to calculate an average PWM'$_{AIR}$. To measure PWM$_{AIR}$', the computing device 218 sets the signal CALIBRATE high. The NAND-Gate (U$_4$) 328 together with AND-Gate (U$_3$) 318 thus cause the analog switch 316 to switch on only during the high phase of the pump current 208. During the low phase, the analog switch 316 is off and no pump current can flow.

At step 622, PWM'$_{AIR}$ is stored in memory. Various techniques may be used to store and retrieve calibration information. For example, the pulse widths (t'$_{1AIR}$ and t'$_{2AIR}$) may be stored directly into memory and used for calculating PWM'AIR at a later time.

Other calibration procedures may be performed in some situations. Calibration procedures for pressure and temperature compensation, for example, may be performed by measuring and storing frequency information corresponding to the pump current 208 at certain calibration conditions.

Figure 7:
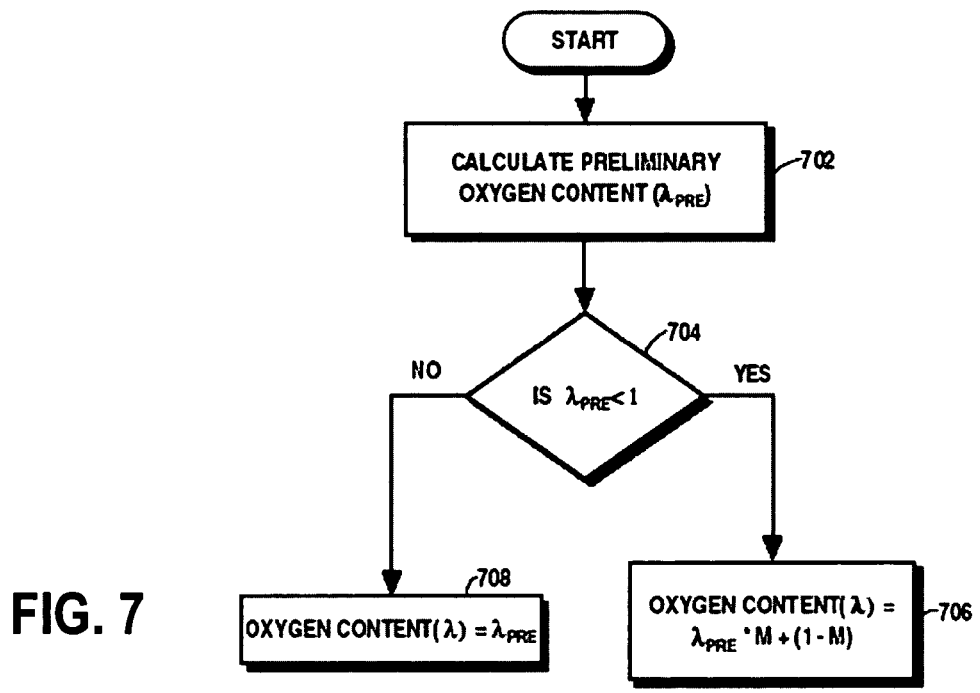
FIG. 7 is a flow chart of a method of determining the oxygen concentration of a gas by comparing the measured pulse width ratio ($PWM_{RATIO}$), to the pulse width ratio function.

FIG. 7 is a flow chart of a method of determining the oxygen concentration of a gas by comparing the measured pulse width ratio, PWM$_{RATIO}$, to the pulse width ratio function. The method described with reference to FIG. 7 is an example of a method of performing step 408 of FIG. 4. Although the discussion with reference to FIG. 7 is directed to oxygen sensors, the teachings can be applied to other types of wideband sensors.

At step 702, a preliminary oxygen concentration, ($\lambda_{PRE}$) is calculated. For the examples discussed herein, the preliminary oxygen concentration ($\lambda_{PRE}$) is determined by the following equation:

$$\lambda_{PRE}=P/(PWM_{AIR}-PWM_{RATIO}) \quad (3)$$

$$\text{where } P=(1+PWM'_{AIR})(1-PWM_{AIR})/(1-PWM'_{AIR}) \quad (4)$$

The computing device 218 retrieves from memory the values for PWM$_{AIR}$, PWM$_{RATIO}$, and PWM'$_{AIR}$ and applies the above equations to calculate the preliminary oxygen concentration, $\lambda_{PRE}$. As explained below, P is equal to PWM$_{AIR}$ where the pulse width ratio at the stoichiometric ratio (PWM$_{ST}$) is zero. Therefore, $\lambda_{PRE}$ is equal to PWM$_{AIR}$/(PWM$_{AIR}$-PWM$_{RATIO}$) where the PWM$_{ST}$ for the particular sensor is zero.

At step 704, it is determined whether $\lambda_{PRE}$ is less than one. If $\lambda_{PRE}$ is less than one, the procedure continues at step 706. Otherwise, the procedure continues at step 708, where the oxygen concentration ($\lambda$) of the gas is determined to be equal to the preliminary oxygen concentration, $\lambda_{PRE}$.

At step 706, the oxygen concentration ($\lambda$) of the gas is determined to be equal to the sum of the preliminary oxygen concentration ($\lambda_{PRE}$) multiplied by a calibration factor (M) and 1 minus the calibration factor ($\lambda=(\lambda_{PRE})*M+(1-M)$). For the examples discussed herein, a calibration factor, M, for the brand and model of the particular measuring cell 202 is derived through statistical analysis of the measuring cell's 202 performance when exposed to a gas with a known oxygen concentration. In some circumstances, a calibration factor for each of several measuring cells is stored in memory and applied to the particular model that is connected within the oxygen measuring device 222. An example of typical value of M is 0.71428.

Figure 8:
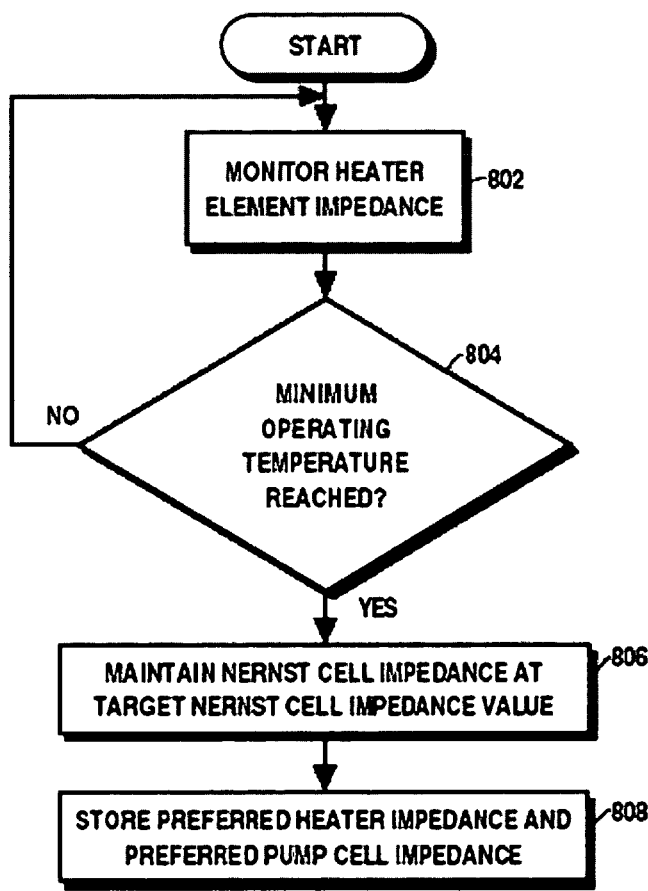
FIG. 8 is a flow chart of a method of calibrating the heater control unit.

FIG. 8 is flow chart of a method of calibrating the heater control unit 302. The method discussed with reference to FIG. 8, therefore, provides an example of a method for performing step 606 of FIG. 6. Although the discussion with reference to FIG. 8 is directed to oxygen sensors, the teachings can be applied to other types of wideband sensors.

At step 802, the heater element 330 impedance is monitored as the temperature of the heater element 330 is increased. In the monitoring device described with reference to FIG. 3, the analog switch 316 is initially opened during the heater unit calibration procedure. In accordance with the appropriate heating timetable, power is applied to the heater element 330 to increase the temperature. The heater control unit 302 monitors the current and voltage across the heating element and determines the impedance of the heater element. Based on stored information relating the heater element impedance to the temperature of the heater element 330, the heater control unit determines when the minimum operating temperature of the oxygen sensor cell 224 is reached. In response to a determination that the desired minimum operating temperature is reached, the heater control unit 302 presents a "high" enable signal at the "Ready" output. The AND gate (U3) 318 closes the analog switch 316 when the ENABLE signal goes "high".

At step 804 it is determined whether the minimum operating temperature has been reached. The procedure proceeds to step 806 when the minimum operating temperature is reached. Otherwise, the heater temperature continues to be monitored at step 802 with the analog switch 316 opened.

At step 806, the Nernst cell impedance is maintained at the target Nernst cell impedance. The heater control unit 302 is controlled such that the temperature is varied to maintain the Nernst cell impedance at the target value. The target Nernst cell impedance is a predetermined value that depends on the type and brand of the measuring cell (sensor) 202 and is provided by the sensor manufacturer. The Nernst cell impedance is held constant or nearly constant for a minimum time to allow fluctuations in temperatures and impedances to settle. An example of a suitable settling time is ten seconds.

As described above, the Nernst cell (224) impedance is monitored by passing the output voltage signal of the Nernst cell (224) through a high pass filter and amplifier (not shown). The resulting filtered and amplified signal is sampled at the comparator transition point. The peak-peak voltage, U$_{NPP}$, is calculated as the difference between the sample voltage at low-high and high-low transition in accordance with Equation 2.

At step 808, the preferred heater impedance and the preferred pump cell impedance are measured and stored. For the examples discussed herein, the pump cell impedance is calculated based on Equation 1. As discussed above, the voltage at the pump cell 204 (output of U$_2$) is determined by Vcc, R$_{PUMP}$, the resistor R$_4$, and the back-EMF of the pump cell 204 when the oxygen measuring device 222 is in an oscillating mode. The output of the operational amplifier (U$_1$) 322 of the comparator 304 switches between 0V and Vcc. The heater control unit 302 samples the output of the operational amplifier (U$_2$) 308 before and after each transition of the output of the operational amplifier (U$_1$) 322. The absolute value of the difference between the voltage measured before and after each transition is U$_{DIFF}$. In some circumstances, the output of the operational amplifier (U$_2$) 322 is passed through a high pass filter (not shown) of sufficiently high cut-off frequency. The filter output is sampled immediately after the transition point and the absolute value of resulting output voltage is equal to U$_{DIFF}$.

Although various calibration factors and equations may be used depending on the particular implementation of the oxygen measuring device, the above equations are derived based on the following analysis and assumptions for the examples discussed herein. Those skilled in the art will recognize the modifications based on the teachings herein.

The relationships between the various parameters are described below with reference to equations 5-26 where the following is assumed:

$Q_f$ is the required oxygen flow in and out of the measuring cell 202 to maintain the Nernst cell (206) at the transition point;

$Q_1$ is an oxygen flow value out of the Nernst cell (224) at the fixed constant current (Ip);

$Q_2$ is an oxygen flow value into the Nernst cell (224) at the fixed constant current (−Ip);

$t_1$ is the oxygen pump time ($Q_1$ flow) required to switch the Nernst cell (224) from 0.445V to 0.455V; and $t_2$ is the oxygen pump time ($Q_2$ flow) required to switch the Nernst cell (224) from 0.455V to 0.445V.

For the forgoing assumptions, therefore, the Nernst cell (206) voltage is 0.45V with an alternating current (AC) component of 10 mVpp. The resulting $Q_f$ is:

$$Q_f = (Q_1 * t_1 - Q_2 * t_2)/(t_1 + t_2) \quad (5)$$

The timing relationships can be expressed as $$PWM_{RATIO} = (t_1 - t_2)/(t_1 + t_2) \quad (6)$$

Using 1 and 2, equation 1 can be rewritten as:

$$Q_f = [(Q_1 + Q_2) * PWM_{RATIO} + Q_1 - Q_2]/2 \quad (7)$$

Pump flow ratio ($Q_{RAT}$) can be expressed as:

$$Q_{RAT} = (Q_1 - Q_2)/(Q_1 + Q_2) \quad (8)$$

At changing air pressure, $Q_1$ and $Q_2$ change approximately proportionally and, therefore, $Q_{RAT}$ stays nearly constant. The same holds true for temperature changes. Accordingly, $Q_{RAT}$ is independent of temperature.

In some circumstances, $Q_{RAT}$ may change when the sensor ages and, therefore, the sensor may need to be periodically calibrated to maintain optimal performance.

If $Q_1$ and $Q_2$ are known and are constants, the oxygen flow rate and Lambda, (λ) is determined from the timing relationship, $PWM_{RATIO}$, which is measured. $Q_1$ and $Q_2$ are constant if the pump current 208, temperature, exhaust pressure, barometric pressure and oxygen concentration in air are constant. For the examples discussed herein, the pump current 208 and temperature are held constant through careful circuit design. For the analysis described herein, the atmospheric oxygen concentration is assumed to be constant at 20.9%. Barometric pressure effects are compensated through calibration. The effect of exhaust pressure tends to modify both, $Q_1$ and Q2 by an equal factor and also modifies the response time of the oxygen sensor cell 206 because more or less oxygen ions are present at the oxygen sensor cell 206 surface depending on pressure.

As described above, the oxygen monitoring device 222 measures oxygen flow by switching the pump current 208 between a constant positive and negative value. The absolute value for this constant pump current value is chosen such that it is greater than the absolute value of the pump current 208 required for free air.

The above equation is linear and can be determined with two known points. The time values $t_1$ and $t_2$ are measured by a crystal controlled microprocessor or timer circuit which allows the accurate determination of Lambda, (λ), once the two calibration points are known.

A stoichiometric exhaust mixture does not require any corrective oxygen flow and the steady state pump current 208 is, therefore, equal to zero. This condition is used to determine one of the calibration points, the stoichiometric pulse width ratio, $PWM_{ST}$.

As described above, a second calibration point is obtained by measuring the pulse width ratio when the measured gas is air. The measuring cell 202 is exposed to free air. If the measuring cell 202 is not installed in a vehicle, the measuring cell is placed in an area exposed to free air. If the measuring cell 202 is installed in a vehicle, the calibration for free air is performed when the vehicle has not been in operation for an adequate time and all the exhaust gases have dissipated or when the vehicle is in a cost-down mode. During the coast-down mode, the throttle on the engine is completely closed and engine speed is above a predetermined value. In this case, a typical ECU will not inject any fuel because no power output is required from the engine and further fuel can be saved. The pump cell 204 is then driven with a total flow value $Q_F$ that is high enough to pump all oxygen from the air in the measuring chamber.

From equations 5 through 8 follows:

$$PWM_{ST} = -Q_{RAT}. \quad (9)$$

The lambda value, λ, calculated from exhaust oxygen concentration can be expressed as:

$$\lambda = \text{Air Oxygen content}/(\text{Air Oxygen content} - \text{Excess Oxygen}) \quad (10)$$

Note that the value Excess Oxygen in Equation 10 can have negative values if all oxygen is consumed but unburned or partially burned fuel is still present.

To examine the oxygen flow rate instead of volume, t is eliminated by division:

$$\lambda = Q_{f(AIR)}/(Q_{f(AIR)} - Q_f); \quad (11)$$

applying equations 7, 8, 9, and 11:

$$\lambda = (PWM_{AIR} - PWM_{ST})/(PWM_{AIR} - PWM_{RATIO}) \quad (12)$$

As described above, a second free air PWM ratio ($PWM'_{AIR}$) is measured by switching the pump cell 204 between $Q_1$ and no current ($Q_2$=0) during free air calibration.

$PWM_{ST}$ is calculated during calibration from $PWM_{AIR}$ and $PWM'_{AIR}$ according to the following formulas:

From equation 7, $$2 * Q_f = (Q_1 + Q_2) * PWM_{AIR} + Q_1 - Q_2 \quad (13)$$

$$2 * Q_f = Q_1 * PWM'_{AIR} + Q_1 \quad (14)$$

Where $PWM'_{AIR}$ is measured when switching between $Q_1$ and no current instead of $Q_1$ and $Q_2$.

$$P = PWM_{AIR} - PWM_{ST}. \quad (15)$$

From equations 13 and 14:

$$P = (1 + PWM'_{AIR}) * (1 - PWM_{AIR})/(1 - PWM'_{AIR}) \quad (16)$$

$$PWM_{ST} = PWM_{AIR} - P \quad (17)$$

Applying equation (12):

$$\lambda = P/(PWM_{AIR} - PWM_{RATIO}) \quad (18)$$

As explained above, $PWM_{AIR}$ is measured by exposing the sensor to free air at the appropriate operating temperature and, in some circumstances, frequency information is used for determining compensation factors. The following analysis demonstrates the relationship between frequency and other parameters.

Returning to equation 8, if $Q_1 = Q_2$, $Q_{RAT}$ (and therefore $PWM_{ST}$) becomes zero. The actual sampling frequency is dependent on the full flow ratio, $Q_F$.

Equation 8 then changes to:

$$Q_f = Q_F * PWM_{RATIO}. \quad (19)$$

Equation 12 becomes $$\lambda = PWM_{AIR}/(PWM_{AIR} - PWM_{RATIO}) \quad (20)$$

$Q_F$ is a function of the pump current 208, Ip, and, therefore, QF=f(Ip). If $Q_F$ for a constant Ip changes because of exhaust pressure changes, the measured $PWM_{RATIO}$ becomes $PWM'_{RATIO}$ for the same corrective flow, $Q_f$.

With exhaust gas pressure or temperature changes $Q_1$ and $Q_2$ change by a factor K in a first approximation.

Equation 8 then becomes:

$$Q_f = K[(Q_1+Q_2)*PWM'_{AIR}+Q_1-Q_2)]/2 \quad (21)$$

where $$Q_1*t_1 = K*Q_1*t_1' \quad (22)$$

$$Q_2*t_2 = K*Q_2*t_2' \quad (23)$$

The measurement frequency f is determined by:

$$f = 1/(t_1+t_2) \quad (24)$$

$$f' = 1/(t_1'+t_2') \quad (25)$$

From equations 20, 21, 22 and 23 follows:

$$K = f'/f \quad (26)$$

Because f is constant when all other environmental conditions are constant, this calculation can be used to correct for temperature and/or pressure changes. Equation 8 then becomes:

$$\lambda = (PWM_{AIR}-PWM_{ST})/(PWM_{AIR}-(1-K)*PWM_{ST}-K*PWM'_{RATIO}) \quad (27)$$

and equation 18 becomes:

$$\lambda = PWM_{AIR}/(PWM_{AIR}-K*PWM'_{RATIO}) \quad (28)$$

These equations, therefore, allow the application of a pressure compensation factor, K to compensate for pressure or temperature changes. Under extreme circumstances, $Q_1$ and $Q_2$ do not change equally by the same factor K. In some situations, therefore, the normalized frequency deviation f''/f is used as an index into an experimentally derived lookup table to extract the accurate deviation factor K':

$$K' = \text{func}(f'/f). \quad (29)$$

The calculated Lambda value can thus be corrected for exhaust pressure changes without the use of separate sensors to measure exhaust pressure once a normalized frequency/lambda table is experimentally determined for a given sensor type.

Conventional commercially available packaged measuring cells 202 often have temperature dependent parasitic resistances to the virtual ground of the pump cell 204 and Nernst cell (224). This parasitic resistance must be addressed through software or circuitry in order to apply pressure compensation methods described above with many commercially available measuring cells 202.

The forgoing equations and analysis may be applied to other implementations of the invention in ways other than described above and the teachings described herein may be applied to a variety of formats, implementations and configurations. As explained above, the hardware and software may be modified to accommodate a variety of factors. For example, the analog switch 316 can be eliminated where the operational amplifier ($U_2$) 308 provides a tri-state output. Also, the analog switch 316 can be connected within the oxygen measuring device 222 before the inverting resistor ($R_4$) 310 instead of connecting to the output of the operational amplifier ($U_2$) 308. The operational amplifier ($U_2$) 308 may also provide a tri-state output. In addition, the heater controlling unit 302 may be integrated as part of the computing device 218.

Further, the Zener diode 314 may be replaced with a digital to analog (D/A) converter or a potentiometer in some circumstances. The references voltage $U_{REF}$ could thereby be set such that the pulse width ratio at the stoichiometric ratio, $PWM_{ST}$ is exactly zero. In such a circumstance, the equation used to calculate A is:

$$\lambda = PWM_{AIR}/(PWM_{AIR}-K*PWM') \quad (30)$$

In some circumstances, frequency information is analyzed to provide other useful information or data in accordance with the analysis above. For example, because the response time of a measuring cell 202 changes with aging, the oscillating frequency is used directly as a measurement to determine the need for replacement. When a lower threshold frequency is reached, the computing device 218 may provide a warning that the sensor should be replaced. The frequency analysis is preferably performed when the free-air value is recalibrated because the environmental conditions are comparable (f' and f in equation 27 are equal) and the frequency change is due to aging of the sensor.

Figure 9:
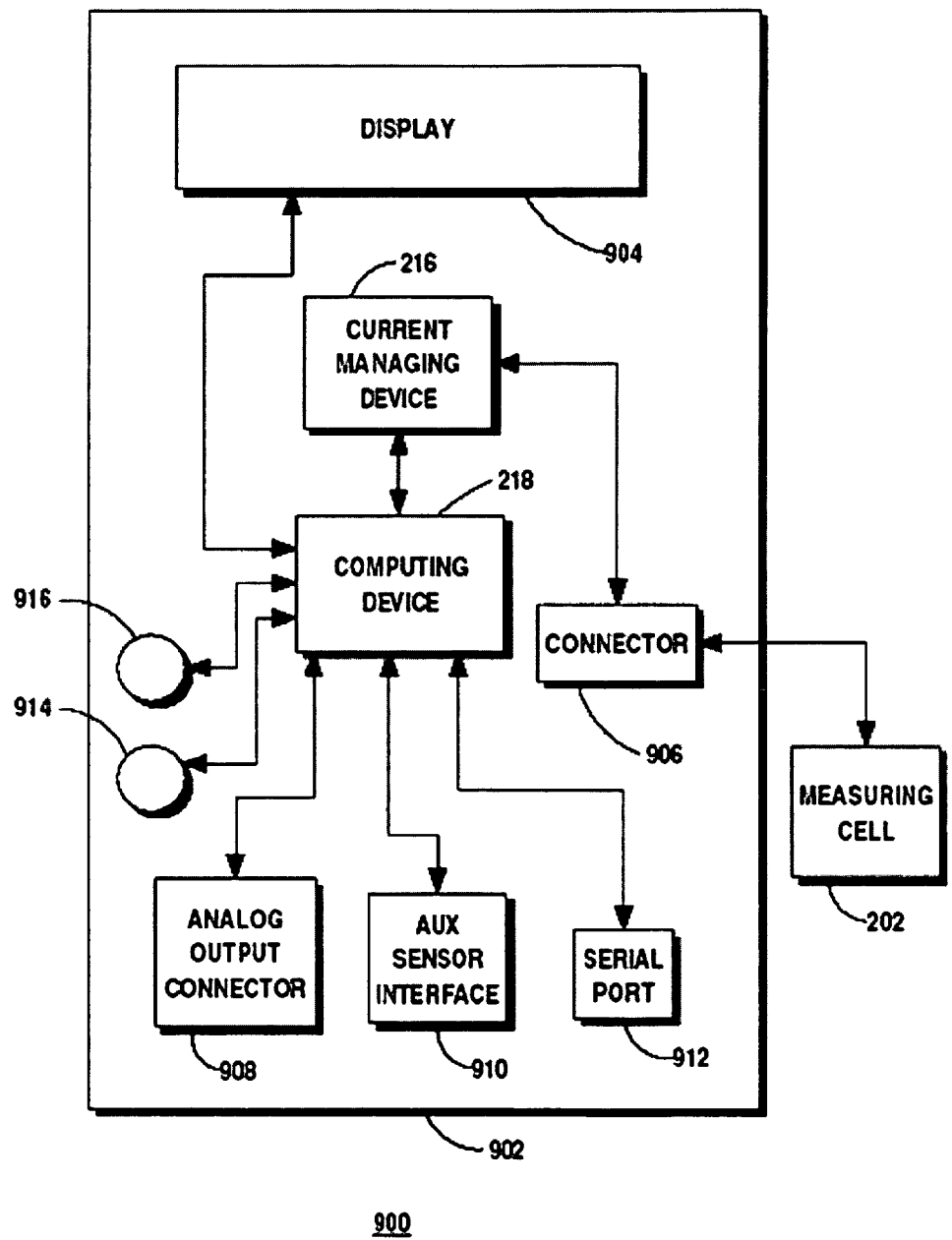
FIG. 9 is a block diagram of a hand-held diagnostic device suitable for embodying the oxygen measuring device.

FIG. 9 is a block diagram of a hand-held diagnostic device suitable for embodying the oxygen measuring device 222. As mentioned above, the oxygen measuring device 222 may be implemented as any of several configuration and devices. The oxygen measuring device 222, for example, may be integrated as an OEM device in a vehicle fuel system. Further, the oxygen measuring device 222 may be part of an in-vehicle aftermarket fueling system or diagnostic system. Other devices and uses will be readily apparent to those skilled in the art based on the teachings herein.

The hand-held diagnostic device 900 includes a housing 902, a display 904, connectors 906-912, and buttons (or other type of switches) 912, 914 that provide interfaces to the computing device 218 and the current managing device 216. The display allows the user to view information regarding the status to the hand-held diagnostic device 900. In the hand held device 900, the connectors 906-912 include a serial port 912 for connecting to an external computer, analog output connector 908 for supplying an analog signal corresponding to the measured A, an auxiliary sensor interface 919, and a sensor connector 906. Other connectors such as a power connector for receiving DC supply power, for example, are also included in some circumstances. A calibrate button 908 connected to the computing device 218 provides a user interface for initiating the calibration procedure. A record button 914 provides a user interface for initiating a record procedure that allows several seconds of data to be stored in memory. An example of another button or switch that may be used includes an on-off switch (not shown). The buttons and connectors are connected to the computing device 218 and other circuitry and provide interfaces between the user, the measuring device 222, the measuring cell 202 and other external equipment.

Therefore, the system, apparatus and method for measuring the oxygen concentration of gas provides a cost effective, efficient and accurate way to monitor a gas having several advantages over conventional systems. The techniques described herein provide a simplified design since no analog to digital (A/D) conversion is required for an oxygen concentration (λ) measurement. Further, no calibration resistor is required in the measuring cell sensor to compensate for sensor tolerances which results in simplified production and lower production costs. Wide tolerances of the measuring cell 202 itself are acceptable, resulting in higher possible production yield. Because no precision resistors or other precision parts are required, circuit cost is minimized. The oxygen monitoring device 222 self-compensates for pressure and temperature variations. The measurement process is converted to the time-domain, instead of an analog current/voltage domain. By using standard crystal time bases, as is typical in digital designs, temperature and age-related drifts are eliminated because crystal time bases have tolerances of $<10^{-6}$ compared to $<10^{-2}$ for typical resistors. Measurement results are linear to 1/Lambda and independent of the Ip/Lambda curve of the sensor. Calibration is convenient and uses only air as a reference gas.

Although the discussion with reference to FIG. 9 is directed to a hand-held diagnostic device suitable for embodying the oxygen measuring device 222, the teachings can be applied to implement a handheld device for use with other types of wideband sensors. For example, the device 900 may be configured to connect to measuring cell that is responsive to nitrogen or to gaseous oxides of nitrogen.

Figure 10:
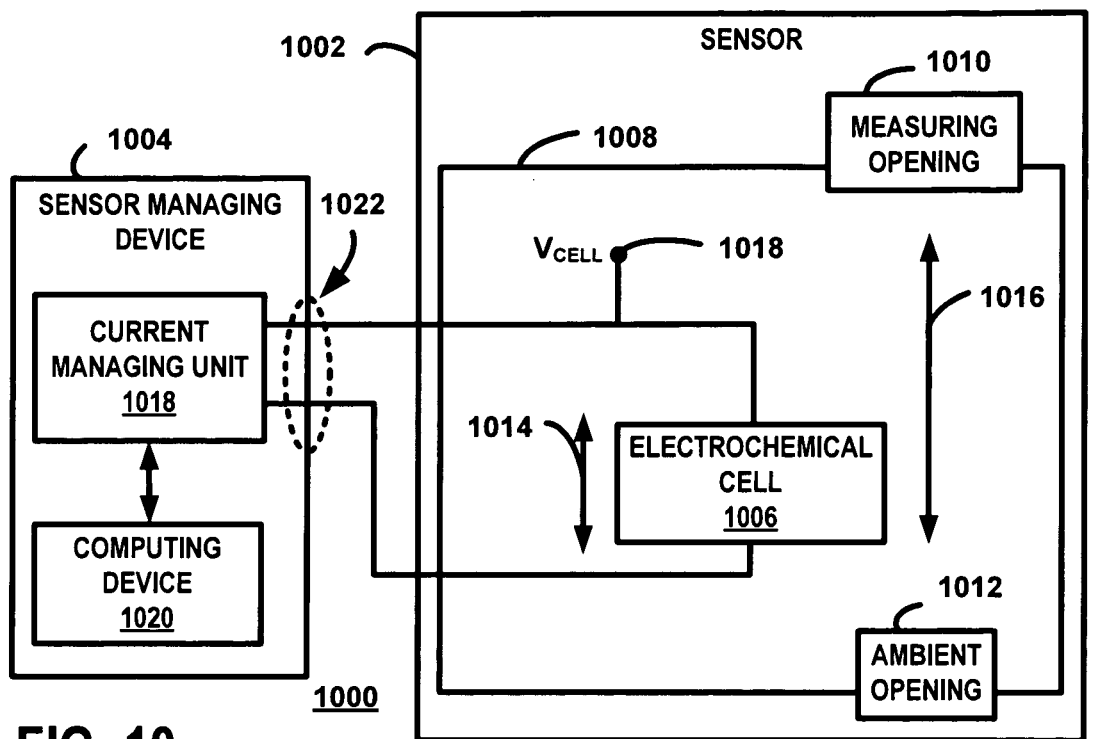
FIG. 10 is a block diagram of a sensor system including a sensor managing device connected to a wideband sensor where a single electrochemical cell performs the functions of the sensor cell and measuring cell.

FIG. 10 is a block diagram of a sensor system 1000 including a sensor managing device 1004 connected to a wideband sensor 1002 in accordance with an example where a single electrochemical cell 1006 performs the functions of the sensor cell and the pump cell. The ion concentration measuring system 1000 includes a sensor that has a measuring cell (formed by a single electrochemical cell) and a sensor managing device that varies a pump current through the electrochemical cell between a first constant current and a second constant current in accordance with a cell voltage at the electrochemical cell. A measured fluid is received through a measuring opening 1010 into a measuring chamber 1008 of the sensor. The electrochemical cell 1006 moves ions between the measuring chamber 1008 and an ambient opening 1012 exposed to an ambient fluid, such as air, based on a pump current flowing through the electrochemical cell 1006. The sensor measuring device 1004 determines the ion concentration of the measured fluid based on a cell voltage ($V_{CELL}$) 1018 at the electrochemical cell 1006. The internal resistance of the electrochemical cell 1006 is determined and the corresponding resistance voltage is subtracted from the cell voltage 1018 to obtain the Nernst voltage of the electrochemical cell 1006 which indicates the ion concentration of the measured fluid.

The sensor system 1000 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

The sensor 1002 includes an electrochemical cell 1006 connected within a measuring chamber 1008 having a measuring opening 1010 and an ambient opening 1012. A magnitude and direction of a pump current 1014 through the electrochemical cell 1006 dictates a flow of ions 1016 within the electrochemical cell 1006. The measuring opening 1010 of the measuring chamber 1008 is positioned to receive a measured fluid while an ambient opening 1012 faces an ambient fluid. The measured fluid and ambient fluid may be a gases or liquids. For the example presented herein, the measured fluid is a measured gas and the ambient fluid is ambient air where the measured gas is oxygen. The electrochemical cell 1006 is any device, component, or element that changes the ion concentrations within the measuring chamber 1008 based on the pump current 1014 flowing through the electrochemical cell 1006 and presents a voltage ($V_{CELL}$) 1018 that is correlated to the ion concentration. The electrochemical cell 1006 is similar to a pump cell in conventional sensors. For this example, the electrochemical cell 1006 is a Nernst cell responsive to oxygen ions. The electrochemical cell 1006, however, may be responsive to other gases in some circumstances such as gaseous oxides of nitrogen (NOx), for example.

When a constant electrical current is forced through the electrochemical cell 1006, a voltage is created at the cell which is the sum of the Nernst voltage and the voltage drop (resistance voltage) created by internal resistance of the electrochemical cell 1006. The internal resistance is the real impedance of the cell sometimes referred to as the Ohmish impedance. The resistance voltage ($V_R$) results from the pump current flowing through the internal resistance. A Nernst voltage indicates the oxygen concentration in the measuring chamber and is equal to the difference between the total electrochemical cell voltage ($V_{CELL}$) and the resistance voltage ($V_R$). The Nernst voltage, therefore, can be calculated by subtracting the resistance voltage ($V_R$) from the electrochemical cell voltage ($V_{CELL}$). For this example, the sensor managing device 1004 continually switches the pump current 1014 between positive and negative constant currents, measures the electrochemical cell voltage ($V_{CELL}$), and determines the oxygen concentration based on the Nernst voltage by subtracting the resistance voltage ($V_R$) from the electrochemical cell voltage ($V_{CELL}$). The sensor managing device 1004 includes a current managing unit 216 and a computing device 218 where the current managing unit controls 216 the current flow and measures the cell voltage. Accordingly, operation in the example discussed with reference to FIG. 10 is similar to the operation of the example described with reference to FIG. 2A, FIG. 2B, and FIG. 3 except that the pump cell and the measuring cell are replaced with a single electrochemical cell. The pump cell in the example of FIG. 10, therefore, also acts as the measuring cell.

The electrochemical cell 1006 provides an output signal based on the number of ions within the measuring chamber 1008. In response to the output signal, the sensor managing device 1004 varies the pump current between two constant current levels. A first pump current is maintained by the current managing unit until the output signal reaches a first threshold. When the first threshold is reached, the current managing unit 1004 directs the pump current 1014 in the opposite direction until the output signal reaches a second threshold level. A computing device monitors the current fluctuation to determine an ion concentration of the measured fluid (gas). The pulse width ratio (duty cycle) of the resulting oscillation is used as an indicator of oxygen flow through the pump cell. Evaluations of the pulse width ratio of the current signal and other related waveforms and signals may be used to determine the oxygen concentration. As discussed above, a suitable application of the sensor system 1000 includes a gas ion monitoring device for monitoring exhaust gas from a combustion engine to determine oxygen concentrations for adjusting an air-fuel mixture. The ion monitoring device, method, and system may be implemented as part of any of several types of applications and systems and may be used to measure any of numerous types of ions within a fluid medium. Some examples include measuring ion concentrations of gaseous oxides of nitrogen such as NO and $NO_2$ ion levels, measuring carbon dioxide levels, measuring gas ion concentrations in liquids such as oxygen and carbon dioxide concentrations in water. Further, ion concentrations of salts and elements such as lead within liquids or gases may be measured in some situations. Accordingly, any of numerous types of ion concentrations may be measured where the ion sensor and current pump are responsive to the particular ions that are measured. Further, as discussed below with reference to FIG. 20, FIG. 21 and FIG. 22, the measuring cell may be used as a primary electrochemical system of a NOx measuring system where the primary electrochemical system provides a first output signal that used as a reference and compared to a second output signal of a nitrogen sensitive electrochemical cell to determine NOx concentrations.

An example of suitable sensor managing device 1004 includes an apparatus that is configured to connect to the measuring cell (electrochemical cell 1006) through an interface 1022 and includes circuitry forming a current managing unit 1018 and a computing device 1020. The interface 1022 may include an electrical connector, direct cable connection, or other electrical contact arrangement for conveying signals between the sensor 1002 and the sensor managing device 1004. The current managing unit 1018 is configured to receive the output signal 1018 based on the ion concentration within the measured fluid within the measuring chamber. The current managing unit 1018 is further configured to adjust an ion flow between the electrochemical cell 1006 and ambient fluid by varying, in accordance with the output signal 1018, the pump current 1014 flowing through the pump cell of the electrochemical cell 1006 between a first constant current and a second constant current. The computing device 1020 is configured to determine the ion concentration of the measured fluid in accordance with the pulse width ratio of a square wave of the pump current. Accordingly, depending on the particular implementation, the computing device 1020 may evaluate any of numerous signals or waveforms related to or derived from the pump current 1014.

Therefore, the measured voltage is used to trigger the reversal of pump current. For example, if during a positive pump current ($I_P$) the Nernst voltage ($|V_{CELL}|-|R*I_P|$)>=0.5 Volt, then the pump current ($I_P$) is reversed, R (internal resistance) is calculated as described below, and the process continues with a negative constant pump current until the Nernst Voltage is <=0.4V. Then the pump current ($I_P$) is polarized back to positive and so on. In this example, the Hysteresis voltage is 0.1V (0.5V-0.4V). Different Hysteresis Voltages can be used. In some cases, the same value may be used for both thresholds.

For this example, the internal resistance (R) of the electrochemical cell is determined by measuring the voltage change at the cell at the transition point between positive and negative current and/or between negative and positive current through the cell. Since the pump current is switched between constant positive and negative currents, the resistance is calculated based on Ohms law.

The internal resistance is dependent on the temperature of the electrochemical cell. At a polarity reversal of the pump current, the cell has not had time to react and has not pumped any oxygen in the new direction. So the oxygen concentration difference, which determines the Nernst voltage, has not yet changed by a significant amount. Accordingly, the voltage change at the cell is at least mostly caused by the change in current. Based on the difference in current and difference in voltage, the internal resistance is determined based on the relationship $R_{CELL} = \Delta V_{CELL}/\Delta I_P$, where $\Delta V_{CELL}$ is the difference in voltage at the cell and $\Delta I_P$ is the difference in pump current. The internal resistance $R_{CELL}$ is used to determine the voltage drop ($V_R$) due to the internal resistance $R_{CELL}$ based on the Ohms Law, $V_R = R_{CELL}*I_P$. The resistance voltage ($V_R$) is subtracted from the actual voltage ($V_{CELL}$) at the electrochemical cell for the remainder of the cycle in subsequent calculations to determine the Nernst voltage and consequently the ion concentration. In most applications, the voltage change $\Delta V_{CELL}$ can be measured up to a few microseconds before and after the current transition. The difference between the voltage immediately before the polarity reversal and immediately after is the $\Delta V_{CELL}$ voltage change. A suitable technique for measuring the $\Delta V_{CELL}$ voltage includes using a sample and hold circuit.

The above discussion can be applied to an example as follows. If the absolute value of the pump current is 5 mA, and measured $\Delta V_{CELL}$ is 0.8 Volts (Ip jumps from +5 mA to −5 mA. As delta Ip is 10 mA (+5 mA−(−5 mA)), $R_{CELL}$ is 80 Ohms. If the measuring chamber is slightly richer than stoichiometric (Nernst voltage is 0.5V), then the actual measured cell voltage at a jump from +5 mA to −5 mA jumps from 0.9V to 0.1 V. Now the pump current is negative (−5 mA) and the pump cell pumps oxygen ions into the measuring chamber(s). This makes that chamber gradually leaner and the pump cell voltage decays. At the lower threshold of 0V (with a 0.1V hysteresis) the polarity of the current is reversed again and the voltage on the cell jumps to 0.8V (0.4V Nernst+$V_R$ of 0.4V). Now oxygen ions are pumped again out of the chamber and the voltage across the pump cell rises again until it reaches the upper threshold of 0.9V (0.5V Nernst+$V_R$ of 0.4V) and so on.

Figure 11:
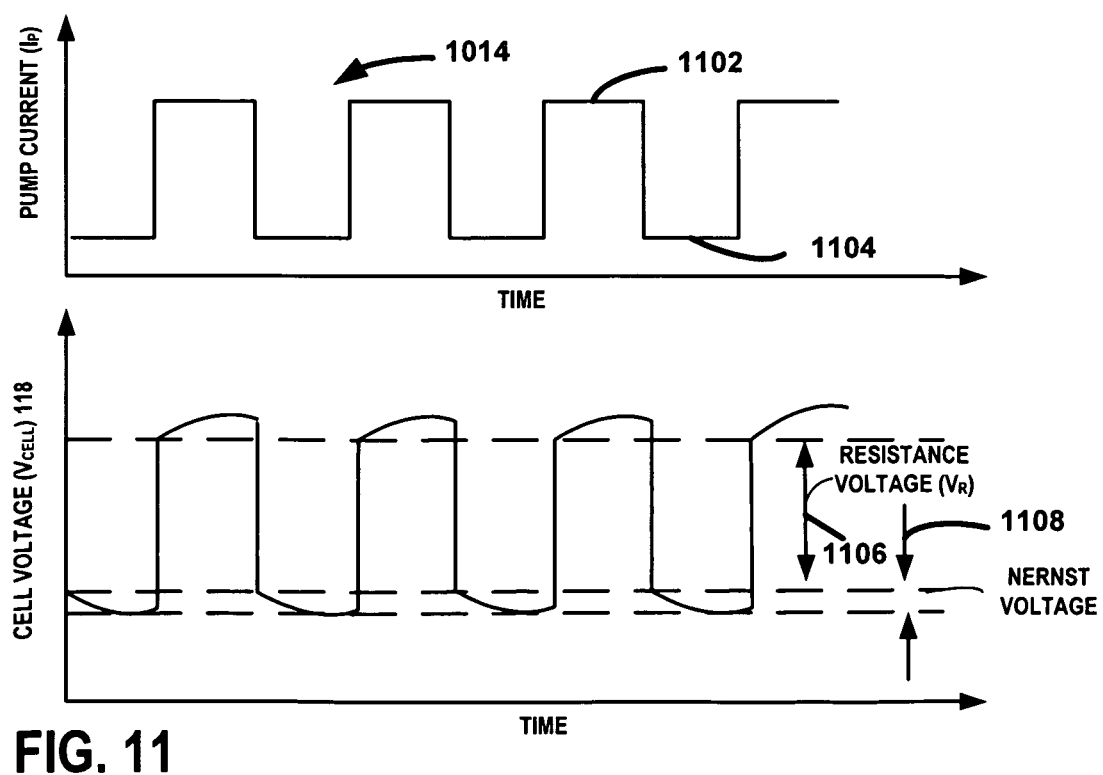
FIG. 11 is a graphical representation of an exemplary pump current and a corresponding cell voltage ($V_{CELL}$).

FIG. 11 is a graphical representation of an example of a pump current 114 and a corresponding cell voltage ($V_{CELL}$) 1018. As the pump current 1014 is switched between a constant positive current 1102 and a constant negative current 1004, the voltage ($V_{CELL}$) across the electrochemical cell (pump cell) also oscillates between negative and positive voltage. As discussed above, a portion ($V_R$) 1106 of the total voltage ($V_{CELL}$) is due to the internal resistance (R) and is referred to as the resistance voltage ($V_R$) 1106. After the pump current is reversed, the opposite resistance voltage appears at the cell and begins to approach a threshold at the total cell voltage. The sum of the resistance voltage and the Nernst voltage 1108 is equal to the total cell voltage ($V_{CELL}$).

Figure 12:
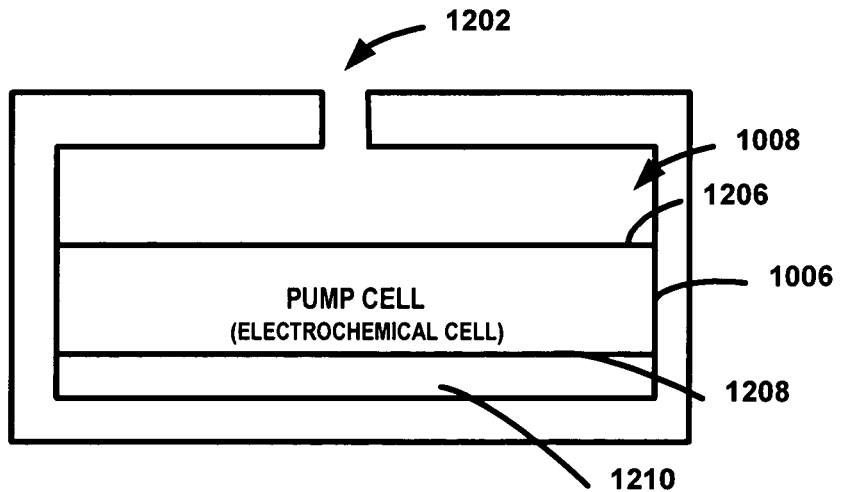
FIG. 12 is a block diagram of a cross sectional view of a sensor including a single electrochemical cell and a diffusion gap for use as the measuring opening.

FIG. 12 is a block diagram of a cross sectional view of a sensor 1200 where the sensor 1200 includes a single electrochemical cell and a diffusion gap 1202 for use as the measuring opening 1010. A measuring side electrode is exposed to the measuring chamber 1008 and an atmospheric electrode is exposed to the atmospheric fluid 1210 such as air. As explained above, conventional wideband sensors exhibit a delay between Nernst reference cell output and changing pump cell current because of the physical separation between the two components. The delay is not applicable in the example of FIG. 12 because the active electrode surface of the pump cell also reacts directly without delay on the measured gas. This further increases the measurement speed. Accordingly, the embodiment illustrated in FIG. 12 is an example of a wideband sensor constructed without a separate sensor reference cell but otherwise in accordance with conventional techniques.

Figure 13:
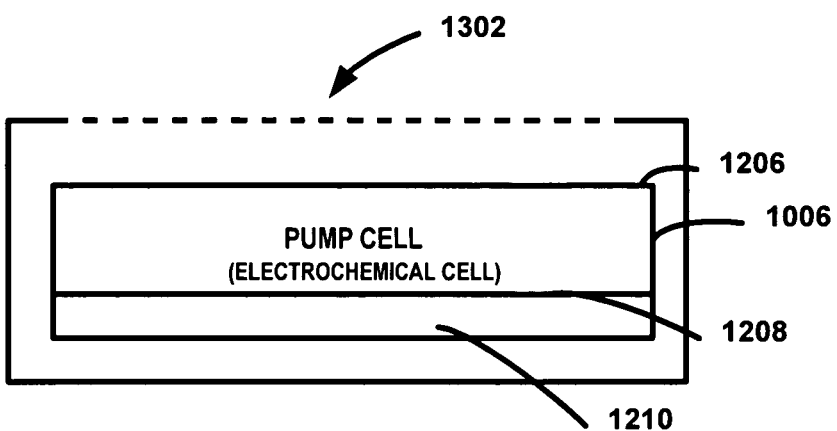
FIG. 13 is a block diagram of a cross sectional view of a sensor that includes a single electrochemical cell and a porous membrane for the measuring opening.

FIG. 13 is a block diagram of a cross sectional view of a sensor 1300 where the sensor 1300 includes a single electrochemical cell and a porous membrane 1302 for the measuring opening 1010. In the implementation shown in FIG. 13, measuring chamber and diffusion gap are omitted. The electrode of the pump cell that is exposed to exhaust gas is covered with an inert porous material that allows weak diffusion of exhaust gas to that sensor electrode. The single diffusion gap and measuring chamber of a conventional sensor is thus replaced with a multitude of diffusion channels. This essentially divides the pump cell surface into a multitude of parallel operating pump cells. This reduces greatly the chance that a single small particle covering the diffusion gap can render the sensor inoperable. Because each pump cell part also has to operate only on a much smaller gas sample compared to a regular wideband sensor, its operating speed can be further increased. The temperature of the sensor, which may be useful to measure because of its effects on diffusion speed and Nernst voltage, can be measured via the internal resistance (Ohmish impedance) of the cell, as the material used for these sensors has a strong negative temperature coefficient. The porous layer may be made of a material that has strong thermal isolating characteristics. It can also serve as protection for the pump cell itself. With appropriate construction, this porous layer by itself can act as protection shield for the sensor, thus eliminating the slowdown in response speed caused by the flow dynamics of metallic shields around conventional wideband sensors.

Accordingly, the apparatus, system, and method discussed with reference to FIGS. 10-13 provide several advantages over conventional ion concentration measuring systems. The elimination of two devices provides for more easily manufactured sensors and reduced delays within the sensors during use. More accurate results are obtained due to the PWM scheme as compared to control loop implementation. Since the internal resistance of the cell is temperature dependent, the calculated internal resistance $R_{CELL}$ value can then be used to measure temperature and to regulate the temperature electrochemical cell (pump cell) by controlling the pump cell heater.

Figure 14:
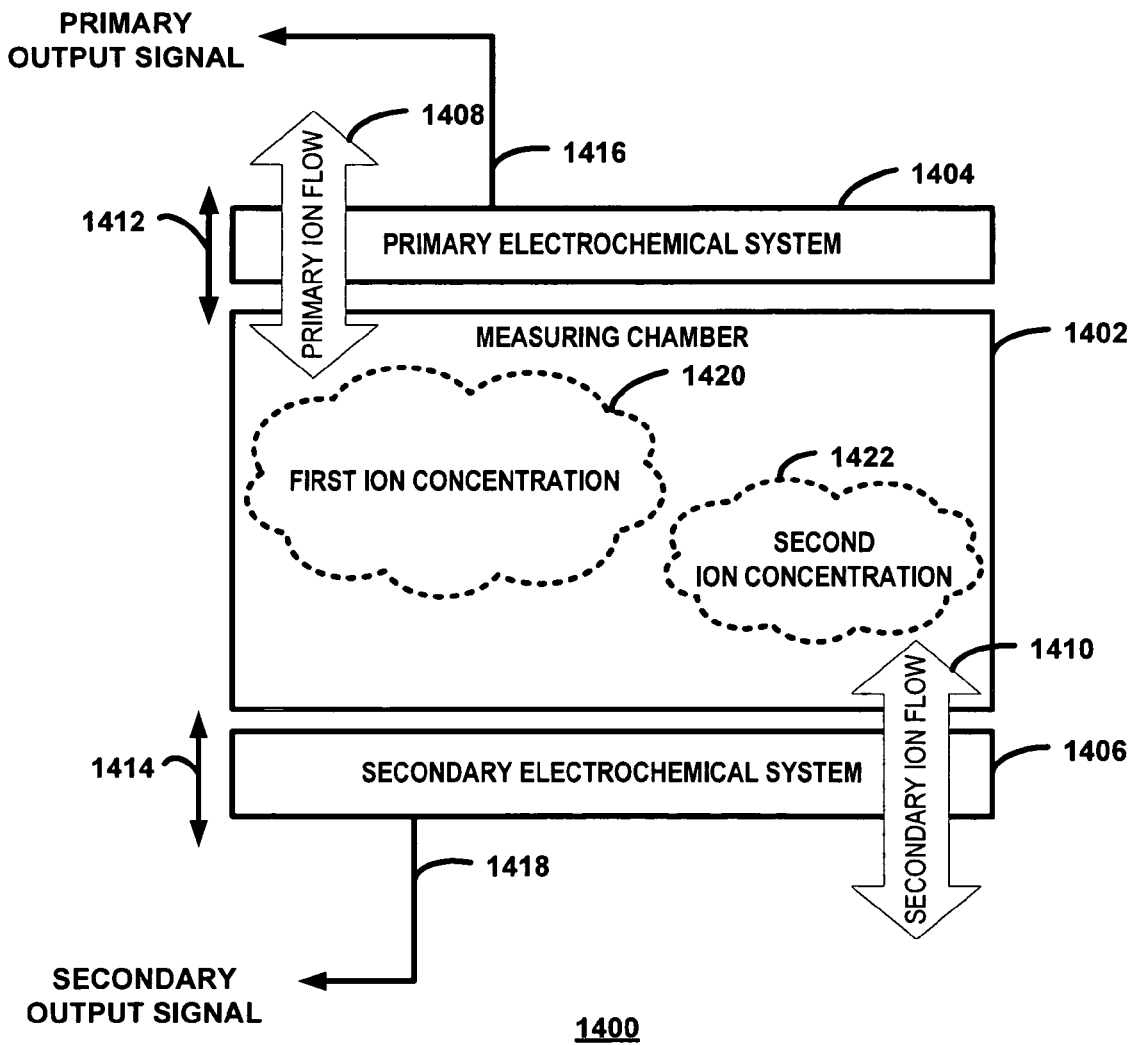
FIG. 14 is a block diagram of an ion concentration sensor including a measuring chamber, a primary electrochemical cell system and a secondary electrochemical cell system.

FIG. 14 is a block diagram of an ion concentration sensor 1400 including a measuring chamber 1402, a primary electrochemical cell system 1404 and a secondary electrochemical cell system 1406. The ion concentration sensor 1400 may be used within various systems and embodiments to measure the ion concentration of fluids such as liquids and gases. As discussed below, the ion concentration sensor 1400 may include pump cells, measuring cells, and electrochemical cells to implement a nitrogen ion sensor.

The primary electrochemical system 1404 and the secondary electrochemical system 1406 each include at least one electrochemical cell and are configured to vary a flow of ions 1408, 1410 into the measuring chamber 1402 and out from the measuring chamber 1402 in response to a corresponding pump current 1412, 1414 and to generate an output signal 1416, 1418 that is based on ion concentrations 1420, 1422 within the measuring chamber 1402. Accordingly, the primary electrochemical system 1404 varies a primary ion flow 1408 into the measuring chamber 1402 and out from the measuring chamber 1402 in response to a primary pump current 1412. A first output signal 1416 is generated in accordance with the first ion concentration 1420 within the measuring chamber 1402. The secondary electrochemical system 1406 varies a secondary ion flow 1410 into the measuring chamber 1402 and out from the measuring chamber 1402 in response to a secondary pump current 1414. A second output signal 1418 is generated in accordance with the second ion concentration 1422 within the measuring chamber. Although the ion concentrations 1420, 1422 may be ion concentrations of different elements, the ion concentrations 1420, 1422 are of the same element in the examples discussed herein. Examples of output signals 1416, 1418 include electrochemical cell voltages generated by an electrochemical cell or measuring cell. For the examples discussed below, the second ion concentration 1422 is a local oxygen ion concentration near a catalytic electrode of the secondary electrochemical system 1406 and the first ion concentration 1420 is a substantially uniform oxygen ion concentration throughout the measuring chamber other than near the catalytic electrode (general oxygen ion concentration). For the examples, therefore, the first ion concentration 1420 is within a first region and the second ion concentration 1422 is within a second region where the second region is closer to the secondary electrochemical system than the primary electrochemical system. The first and second ion concentrations 1420, 1422, however, may be ion concentrations of different elements or have different distributions within the measuring chamber 1402 depending on the particular implementation.

During operation of the ion concentration sensor 1402, the primary pump current 1412 is varied between a first constant primary pump current and a second constant primary pump current to vary the primary ion flow 1408. The varying ion flow increases and decreases the first ion concentration 1420 resulting in a varying first output signal 1426. The primary pump current 1412 is adjusted in accordance with the first output signal 1416. For the implementations below, the primary pump current 1412 is reversed when the first output signal 1416 reaches an upper threshold and when it reaches a lower threshold. The first constant primary pump current has an opposite polarity from the second constant primary pump current.

The secondary pump current 1414 is varied between a first constant secondary pump current and a second constant secondary pump current based on a relationship between the first output signal 1416 and the second output signal 1418. For the implementations below, the secondary pump current 1414 is reversed when a difference between the first output signal 1416 and the second output signal 1418 reaches an upper difference threshold and when the difference reaches a lower difference threshold. Accordingly, the second output signal 1418 indicates a relative ion concentration between the first ion concentration 1420 and the second ion concentration 1422 and the relationship between the second output signal 1418 and the first output signal 1416 indicates an ion concentration. For the implementations below, for example, the duty cycle of a control signal for controlling the secondary pump current indicates an Oxides of Nitrogen (NOx) concentration where the first output signal 1416 indicates oxygen concentration and the second output signal 1418 indicates oxygen concentration resulting from catalytically reducing NOx to oxygen and nitrogen. Any signal or waveform related or derived from the secondary pump current or the control signal for controlling the current can be evaluated to determine the NOx concentration where the evaluated waveform or signal depends on the particular implementation. Also, a hysteresis function is formed that is dependent on the thresholds and which can be adjusted by selecting the thresholds.

Figure 15:
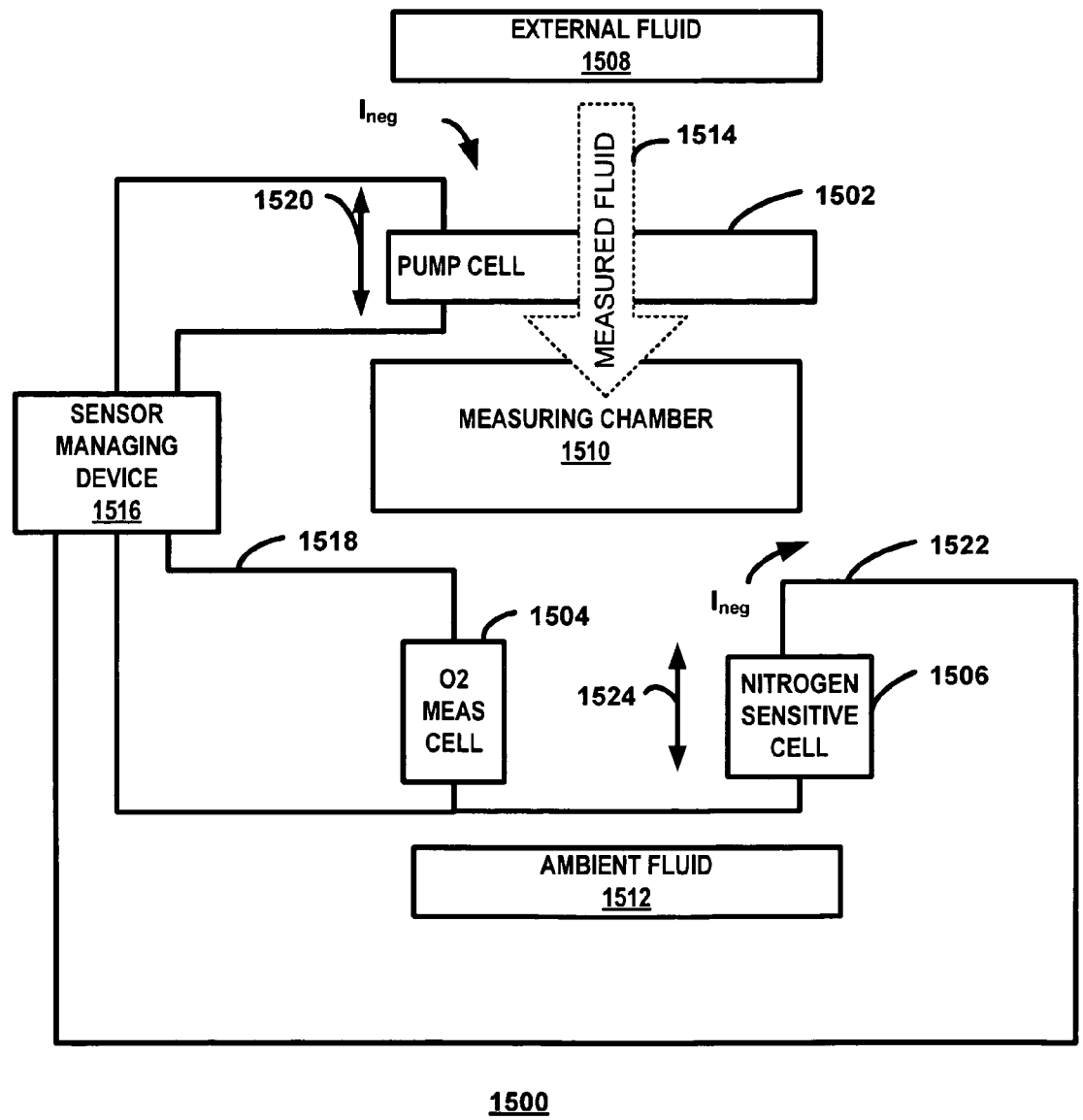
FIG. 15 is a block diagram of an Oxides of Nitrogen (NOx) sensor system including a NOx sensor having a pump cell, an oxygen measuring cell, and a nitrogen sensitive electrochemical cell.

FIG. 15 is a block diagram of an Oxides of Nitrogen (NOx) sensor system 1500 including a NOx sensor 1501 having a pump cell 1502, an oxygen measuring cell 1504, and a nitrogen sensitive electrochemical cell 1506. Accordingly, the NOx sensor 1501 is an implementation of the ion sensor 1400 where the primary electrochemical system 1404 includes the pump cell 1502 and the oxygen measuring cell 1504 and where the secondary electrochemical system 1406 includes the nitrogen sensitive electrochemical cell 1506. The pump cell 1502 is exposed to an external fluid 1508 that is to be measured and a measuring chamber 1510. The oxygen measuring cell 1504 and the nitrogen sensitive cell 1506 are exposed to ambient fluid 1512 and the measuring chamber 1510. Although the sensor 1501 may be designed to work with a variety of fluids including gases and liquids, typical implementations include configurations for measuring gas concentrations. An example of a suitable implementation includes installing the NOx sensor 1501 within an exhaust system of a combustion engine in order to measure the NOx concentration of exhaust gas. In such systems, therefore, the external fluid 1508 is exhaust gas and the ambient fluid 1512 is ambient air.

A measured fluid 1514, such as a measured exhaust gas, is received through a measuring opening such as diffusion gap or other opening to the measuring chamber 1510. As described below with reference to FIG. 16, the measured fluid 1514 is received through a diffusion gap through the pump cell 1502. A sensor managing device 1516 manages the sensor 1501 by controlling cell currents and detecting output signals. The oxygen measuring cell 1504 provides an oxygen cell output signal 1518 that indicates the oxygen ion concentration within the measuring chamber 1510. The oxygen ion concentration, therefore, is an example of the first ion concentration 1420 of the example of FIG. 14. The oxygen measuring cell output signal 1518 is an example of the first output signal 1416.

During operation, the sensor managing device 1516 varies the pump cell current 1520 through the pump cell 1502 between a first constant pump current and a second constant pump current. The oxygen measuring cell output signal 1518 is monitored by the sensor managing device 1516 and used to determine when to switch the direction of the pump current 1520. When the oxygen measuring cell output signal 1518 reaches an upper threshold, the pump current 1520 is reversed from a positive constant pump current that pumps oxygen ions into the measuring chamber 1510 to a negative constant pump current that pumps oxygen ions out from the measuring chamber 1510. When the oxygen measuring cell output signal 1518 reaches a lower threshold, the pump current 1520 is switched back to the positive pump current. The lines illustrating the connections between the sensor managing device and the sensor are functional representations of signals and the actual number of physical connections depends on the particular implementation. Some of the connections may be to ground or other voltage potential. As discussed with reference to FIG. 17, for example, an electrode from each of the cells is connected to ground and only two electrical connections (other than ground) are made between the sensor and the sensor managing device.

The nitrogen sensitive electrochemical cell 1506 is any electrochemical cell that reduces oxide of nitrogen (NOx) into nitrogen and oxygen and that generates a nitrogen cell output signal 1522 that indicates a local oxygen ion concentration at the cell 1506. For the example discussed with reference to FIG. 16 below, the nitrogen sensitive electrochemical cell 1506 includes a platinum and rhodium (Pt/Rh) electrode exposed to the measuring chamber 1510 and that catalytically reduces the NOx to $N_2$ and $O_2$. Where NOx is present, the local oxygen concentration at the NOx cell electrode is higher than the oxygen concentration within the rest of the measuring chamber 1510. This local oxygen concentration, therefore, is an example of the second ion concentration 1422 of FIG. 14. The sensor managing device 1516 compares the nitrogen cell output signal 1522 to the oxygen measuring cell output signal 1518 and applies a nitrogen cell pump current 1524 through the nitrogen sensitive electrochemical cell 1506. The nitrogen cell pump current 1524 pumps oxygen ions out from the measuring chamber to the ambient air 1512 when the nitrogen cell pump current 1524 is negative and pumps oxygen into the measuring chamber 1510 from the ambient air 1512 when the nitrogen cell pump current 1524 is positive. The nitrogen cell pump current 1524 is reversed when the difference between the oxygen cell output signal and the nitrogen cell output signal 1522 reaches an upper threshold and when it reaches a lower threshold. Accordingly, the function (wave form) of the control signal for switching the nitrogen cell pump current 1524 indicates the NOx concentration of the measured fluid 1514. The concentration may be determined by observing other values or signals. The duty cycle of the nitrogen cell pump current 1524 may be analyzed to determine nitrogen concentration, for example. Accordingly, other values derived or related to the difference between the oxygen measuring cell output signal 1518 (first output signal 1416) and the nitrogen sensitive cell output signal 1522 (second output signal 1418) may be used to determine oxides of nitrogen concentration.

Figure 16:
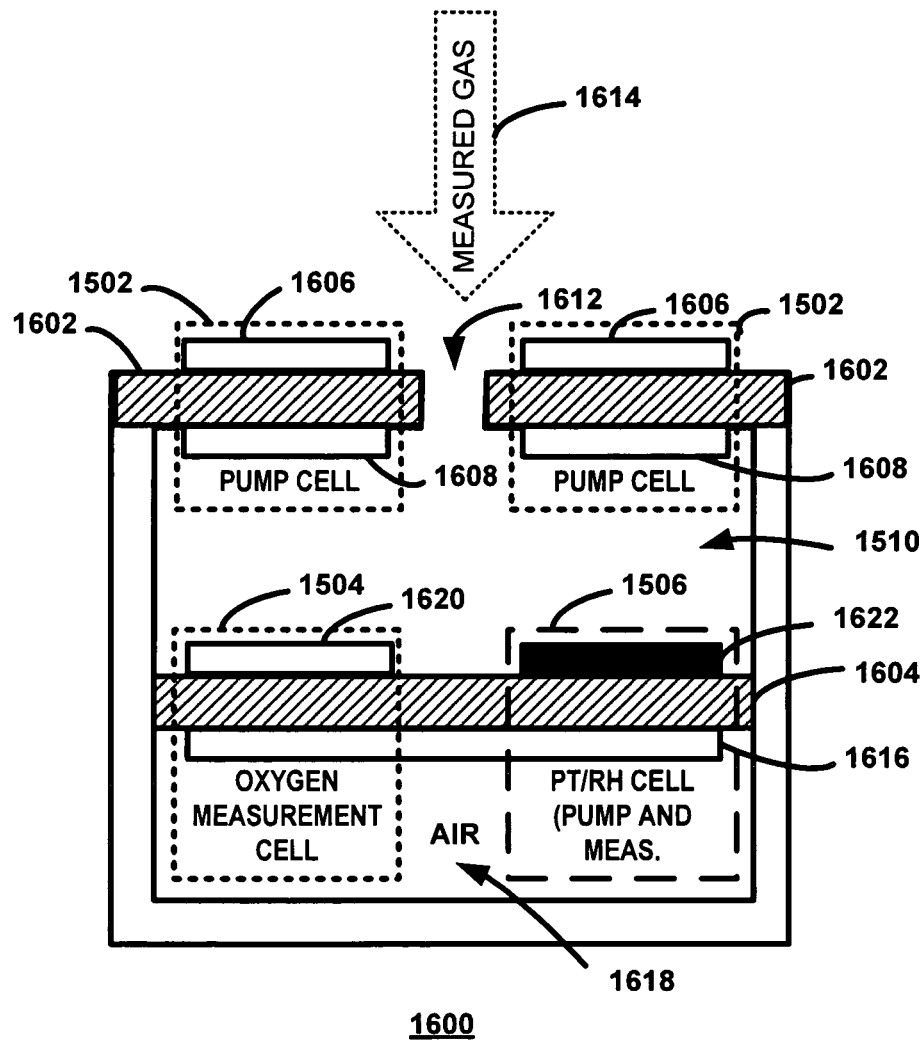
FIG. 16 is a block diagram of a cross section of a NOx sensor for measuring ion concentrations in gases which is an example of an implementation of the NOx sensor of FIG. 15

FIG. 16 is a block diagram of a cross section of a NOx sensor 1600 for measuring ion concentrations in gases which is an example of an implementation of the NOx sensor 1501 of FIG. 15. Accordingly, the NOx sensor 1600 is an example of the NOx sensor 1501 where the NOx sensor 1600 can be used within the exhaust system of a combustion engine. The sensor 1600 may also be used within other systems and for other uses. Other uses may include detection alarms and medical devices.

The NOx sensor 1600 includes two laminated zirconium dioxide (ZrO2) ceramic layers 1602, 1604. A sealed spaced between the layers 1602, 1604 forms the measuring chamber 1510. Platinum electrodes 1606, 1608 are disposed on each side of a first layer 1602 such that an exhaust electrode 1606 is exposed to the exhaust gas 1610 (external fluid 1508) and a measurement electrode 1608 is exposed to the gases in the measuring chamber 1510. A hole 1612 within the first layer forms a diffusion gap for receiving a measured gas 1614 (measured fluid 1514). Other types of diffusion gaps and diffusion layers may be used in some circumstances.

A single platinum electrode (air electrode) 1616 is disposed on a second ZrO2 layer 1604 such that the air electrode 1616 is opposite the measuring chamber 1510 and exposed to ambient air 1618 (ambient fluid 1512). Another platinum electrode (oxygen measuring electrode) 1620 is disposed on the second layer 1604 opposite the air electrode 1616 to form the oxygen measuring cell 1504 with the air electrode 1616 and the second layer 1604. A platinum/rhodium (Pt/Rh) electrode 1622 forms the nitrogen sensitive electrochemical cell 1506 with the air electrode 1616 and the second layer 1604. Accordingly, the first layer 1602 with the platinum electrodes 1606, 1608 form the pump cell 1502 and the second layer 1604 with the platinum layers 1616, 1620 and the Pt/Rh electrode 1622 form the oxygen measuring cell 1504 and the nitrogen sensitive cell 1506. An electrical current 1520 through the pump cell 1502 transports oxygen ions in an opposite direction to the direction of the electrical current. The voltage across the oxygen measuring cell 1504, pump cell 1502, and the nitrogen sensitive cell 1506 is governed by the Nernst equation:

$$Voutn = (R*T/4*F)*\ln(Po1/Po2)$$

where R is the universal gas constant, T is the temperature in degrees Kelvin, F is the Faraday constant, Po1 is the partial Oxygen pressure of one electrode (air for the Oxygen measuring cell and Pt/Rh cell, and exhaust gas for the pump cell), and Po2 is the partial Oxygen pressure of the other electrode (electrodes inside the measuring chamber). Air oxygen partial pressure is approximately 20000 Pascals.

The nitrogen sensitive cell 1506 is responsive to nitrogen and oxygen. The Pt/Rh electrode 1622 catalytically reduces oxides of nitrogen (NOx) into Nitrogen (N2) and oxygen (O2). This mechanism causes a local enrichment of oxygen content (partial pressure) at the surface of the Pt/Rh electrode 1622. Accordingly, the local concentration of oxygen near the Pt/Rh electrode increases when NOx are present. The Nernst voltage between the air electrode and the Pt/Rh electrode is lower than the oxygen measuring cell output voltage (first output signal 1416). The local oxygen concentration near the Pt/Rh electrode 1622 is an example of the second ion concentration 1422 of FIG. 14.

Figure 17:
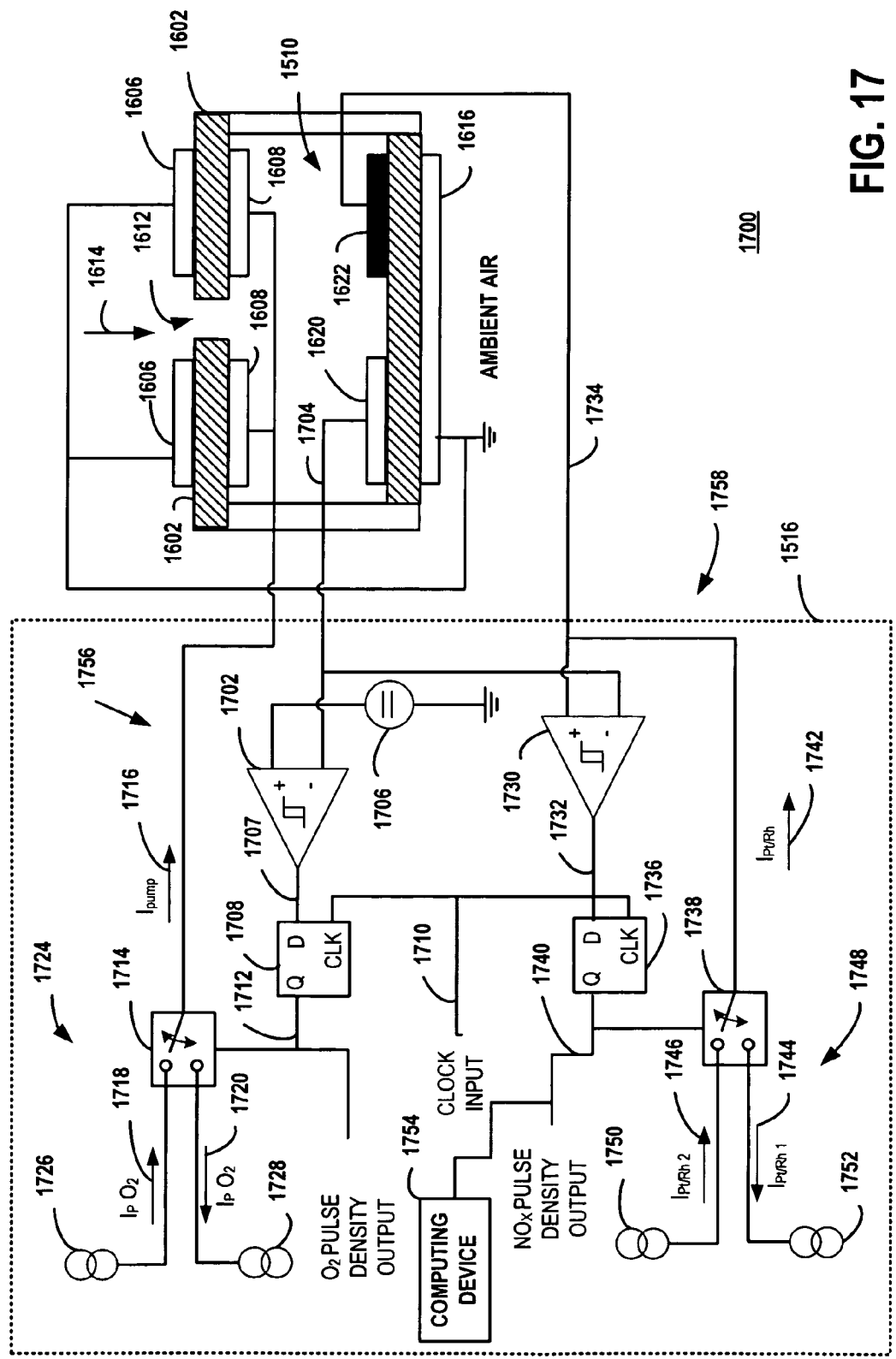
FIG. 17 is a schematic function diagram of a NOx measuring system including the sensor managing device connected to the NOx sensor of FIG. 16.

FIG. 17 is a schematic function diagram of a NOx measuring system 1700 including the sensor managing device 1516 connected to the NOx sensor 1600 of FIG. 16. The NOx measuring system 1700 may be implemented using any combination of hardware, software and firmware. Various functions and operations of the functional blocks described with reference to FIG. 17 may be implemented in any number of devices, circuits or elements. Any of the functional blocks may be integrated in a single device and the functions of the blocks may be distributed over several devices, circuits and elements. Some of the functional blocks may be omitted in some instances. For example, the flip-flops may be omitted since the operation of these devices is inherent in the counting of output pulses by counters. FIG. 17, therefore, is a diagram of an example of an implementation of the sensor 1600 as connected within a measurement system. The various elements, devices, values, signals, and functions described with reference to FIG. 17 may differ for other measurement systems using other implementations of the sensors 1400, 1501, 1600, depending on the particular structure, use, environment and requirements of the particular measurement system and sensor.

A first comparator 1702 with hysteresis continuously compares the oxygen measuring cell voltage 1704 (first output signal 1416) across the oxygen measuring cell 1504 to a reference voltage 1706. For this example, the reference voltage 1706 is −450 mV. When the oxygen measuring cell voltage 1704 (first output signal 1416) drops below a lower threshold, the first comparator output is a logic high signal and when the oxygen measuring cell voltage 1704 (first output signal 1416) rises above an upper threshold, the first comparator output is a logic low signal. The upper and lower thresholds are determined by the hysteresis of the comparator 1702 and are selected to correspond to oxygen concentration thresholds within the measuring chamber 1510. The first comparator output 1707 is processed by a first flip-flop (FF1) 1708 such that a clock input 1710 gates a FF1 output 1712 of the first flip-flop 1708. The FF1 output 1712 controls a first current switch 1714 which directs a pump cell current 1716 through the pump cell 1502 between a first constant pump current 1718 and a second constant pump current 1720. For this example, the first and second constant pump currents are equal in magnitude but have an opposite polarity. Therefore, after the first comparator output 1707 drops below the lower threshold (−½ hysteresis), the first flip flop output 1712 is set to high at the next clock cycle. The resulting high FF1 output sets the first current switch 1714 to direct a constant positive pump current 1718 through pump cell 1502. In this state, the pump cell 1502 pumps oxygen from the exhaust side electrode 1610 through the pump cell 1502 and into the measuring chamber 1510. The first current switch 1714 remains in this position until switched by the FF1 output 1712. When the oxygen measuring cell voltage 1704 reaches the upper threshold (+½ hysteresis), the first comparator 1702 generates a first comparator output signal that is a logic low. At the next clock cycle, the first flip-flop 1708 out changes to a logic low signal to switch the first current switch 1714 to the negative constant pump current 1720. FIG. 17 illustrates a switching current source 1724 that includes a positive current source 1726 and a negative current source 1728 that are directed by the first switch 1714. Accordingly, the switching current source 1724 provides the primary pump current 1412 referred to in FIG. 14. Any of numerous techniques and circuits can be used to achieve the functionality of the switching current source 1724 that switches from the first constant pump current 1718 to the second constant pump current 1720. An example of a suitable technique includes using an output of an operational amplifier as an input to provide a feedback loop as described above. Another example includes using a transistor circuit as a current source and using an electronic switch to switch between the current source and current sink.

The second comparator 1730 with hysteresis generates an output 1732 based on a relationship between the oxygen measuring cell voltage 1704 (first output signal 1416) and the Pt/Rh cell output voltage 1734 (second output signal 1418). As described above, the PT/Rh electrode 1622 reduces NOx into N2 and O2 and generates and output 1734 based on the local oxygen concentration near the Pt/Rh electrode 1622. When NOx are present, the local oxygen concentration increases and the Nernst voltage between the air electrode 1616 and the Pt/Rh electrode 1622 is lower than the Nernst voltage between the air electrode 1622 and the measurement electrode 1620 of the oxygen measuring cell 1504. The second comparator 1730 continuously compares the Nernst voltage of the oxygen measuring cell 1704 (first output signal) and the Nernst voltage of the Pt/Rh cell (second output signal). When significant levels of NOx are present and the difference of the PT/Rh cell voltage and the oxygen measuring cell voltage is below a lower threshold (e.g. the difference has magnitude above a threshold magnitude), the second comparator 1730 generates a second comparator output signal 1732 that is a logic low. At the next clock cycle, a second flip-flop 1736 generates a FF2 output 1740 that is also a logic low. The FF2 low signal sets the second current switch 1738 to direct the Pt/Rh cell current 1742 (secondary pump current 1414) through the Pt/Rh cell 1506 at a first constant Pt/Rh cell current 1744 (first constant secondary pump current). The first constant secondary pump current, therefore, is a relatively small negative pump current that flows from the air electrode 1616 to the Pt/Rh electrode 1622 for the example of FIG. 17. When the first constant secondary pump current is applied, the electrochemical cell forming the Pt/Rh cell 1506 functions as a pump cell to pump oxygen from the measuring chamber 1510 through the Pt/Rh cell 1506 to ambient air 1524. Accordingly, oxygen flow through the Pt/Rh cell 1506 is opposite in direction to the current flow 1742. When the oxygen is adequately depleted to establish a local oxygen concentration that is less than a threshold, the second comparator 1730 generates a second comparator signal 1732 that is a logic high value. Accordingly, the comparator 1730 detects that the Pt/Rh cell and the oxygen measuring cell have the same voltage (or nearly the same voltage due to the hysteresis) and generates the high logic signal. At the next clock cycle, the second flip-flop 1736 provides a logic high signal to the second switch 1738 to switch the Pt/Rh cell current 1742 (secondary pump current 1414) from the first constant Pt/Rh cell current 1744 (first constant secondary pump current) to a second constant Pt/Rh cell current 1746 (second constant secondary pump current). The Pt/Rh cell current 1742, therefore, switches from a constant negative Pt/Rh cell current 1744 to a constant positive Pt/Rh cell current 1746 where the currents 1744, 1746 are relatively small compared to the pump cell currents 1718, 1720. The relatively small positive current through the Pt/Rh cell pumps oxygen from the air 1524 into the measuring chamber 1510. The local oxygen concentration near the Pt/Rh electrode continues to increase due to the positive secondary pump current and the contribution of any catalytically reduced NOx until the lower threshold is reached and the process repeats. FIG. 17 illustrates a switching current source 1748 that includes a positive current source 1750 and a negative current source 1752 that are directed by the second switch 1738. Any of numerous techniques and circuits can be used to achieve the functionality of the switching current source 1746 that switches from the first constant Pt/Rh cell current 1744 to the second constant Pt/Rh cell current 1746. Accordingly, the switching current source 1748 provides the secondary pump current 1414 referred to in FIG. 14.

The NOx pulse density output of the second flip-flop output signal 1740 indicates the concentration of NOX in the measuring chamber 1510. Where there is no NOx present, the number of logic highs (1s) and logic lows (0s) of the signal 1740 are equal for a given time period. This occurs since there is no need to pump out any additional oxygen produced by the Pt/Rh electrode 1622. As the NOx concentration increases, more oxygen is catalytically produced and pumped out and the number of 1s increases relative to the number if 0s over a given time period. Accordingly, the duty cycle of the NOx pulse density output 1740 is a measurement of NOx.

A computing device 1754 receives the control signal 1740 and determines the NOx concentration from the duty cycle. The computing device 1754 can be implementation using a processor, a microprocessor, or combination of hardware, software and/or firmware. The computing device may include counters in some situations. In some cases, a table may be used to compare the duty cycles to stored values correlated to concentrations. In other situations, the concentration may be calculated based on a stored equation. The relationship, for example, between the duty cycle and concentration is linear, or nearly linear, in most situations. Therefore, the detected duty cycle may be calculated and applied to a linear equation to determine the concentration.

The various, signal polarities, magnitudes, logic levels and frequencies are selected in accordance with the particular implementation. Some examples of suitable values include the following. An example of a suitable secondary pump current includes a secondary pump current magnitude that is 2 to 3 times orders of magnitude lower than then primary pump current. Such a selection is often suitable since typical NOx content within the measuring chamber is many orders lower than the oxygen content. The hysteresis of the first comparator is chosen such that the oscillation of the circuit controlled by the comparator is on the order of 50 to 100 Hz. The hysteresis of the second comparator is chosen such that the oscillation of the NOx circuit controlled by the second comparator is on the order of one to two kilohertz (1-2 KHz). In many circumstances, the hysteresis of the second comparator 1730 is selected to compensate for the voltage ($V_R$) across the Pt/Rh cell due to the resistance of the cell. The output voltage ($V_{Cell}$) of the Pt/Rh cell 1506 is due to the combination of the Nernst voltage governed by the Nernst Equation and the resistance voltage ($V_R$). ($V_R$) is equal to ($I_{Pump2}$) $R_{Cell}$, where $R_{Cell}$ is the internal resistance (impedance) of the Pt/Rh cell and where ($I_{Pump2}$)$_{is}$ the secondary pump current. Although the $V_R$ switches polarity depending on the current direction, the Nernst voltage does not.

Therefore, the measuring system 1700 measures the NOx content of exhaust gas 1508. A measured gas 1614 is diffused through a single diffusion gap 1612 into the measuring chamber 1510. A primary electrochemical system directs and measures oxygen within the measuring chamber while a secondary electrochemical system operates in parallel to measure NOx. The secondary electrochemical system reduced the NOx into $N_2$ and $O_2$ and manages flow of $O_2$ into and out from the measuring chamber in parallel to the flow of oxygen managed by the primary electrochemical system. As explained above, this mechanism provides several advantages over conventional NOx sensors. For example, conventional NOx sensors have less sensitivity and are more susceptible to errors and noise due to their structure. As discussed above, conventional NOx sensors typically include two diffusion gaps and measuring chambers. A measured gas is received by a wideband oxygen sensor through a first diffusion gap. The wideband oxygen sensor is positioned in series (in terms of gas flow) with a limit current flow sensor. The wideband oxygen sensor is used to deplete the measured gas of oxygen while leaving NOx intact. This oxygen depleted gas is diffused through the second diffusion gap into second measuring chamber. A Pt/Rh cell within the second chamber is oxygen and nitrogen sensitive. A constant voltage imposed on this cell causes an oxygen ion flow. This externally imposed voltage is opposed by the Nernst voltage of the cell and, therefore, a very small current develops. The small current is linear with the NOx content over a small range. The range can be extended by imposing different voltages, at the cost of resolution. Because this current is very small (in the nano-ampere range) and reacts to NOx content very slowly, the sensor follows the NOx content also very slowly. This is aggravated by the need for the NOx to flow through two diffusion gaps and measuring chambers. Because the system relies on a constant low oxygen content, any error in that oxygen content shows up as error in the NOx measurement. This of course limits the maximum sensitivity of the sensor. The very small current is also very sensitive to noise and the measurement is extremely sensitive to electrical noise. These and other limitations are reduced or eliminated with the structures, circuits, and techniques discussed herein.

As mentioned above, the functions and elements described with reference to FIG. 17 may be implemented using any combination of hardware, software and/or firmware. An example of a suitable implementation of the current source 1726 and current sink 1728 includes a current source with switchable polarity. A Schmitt-Trigger circuit consisting of an operation amplifier and resistors is an example of a suitable comparator 1702 with Hysteresis. The voltage source can be realized with a resistor divider network.

During operation, therefore, the comparator 1702 with hysteresis compares the output of $O_2$ measuring cell consisting of the measuring chamber electrode 1620 and air electrode 1616 to a fixed voltage from voltage source 1706. The output of the comparator is synchronized to the clock source with the first flip-flop (D-Flip Flop) 1708. The output of the flip flop 1708 controls the direction of the pump current through switch 1714. The output of the D-Flip Flop 1708 is a pulse-density modulated signal whose pulse density (or duty cycle) is proportional to the $O_2$ concentration of the measured gas. The comparator (with Hysteresis) 1730 compares the output of the $O_2$ reference cell (1620, 1616) to the voltage at the Pt—Rh NOx sensitive cell consisting of Pt—Rh electrode 1622 and air electrode 1616. If no NOx is present, the Nernst voltages at the NOx sensitive electrode and the $O_2$ sensitive only electrode should be the same. Due to the hysteresis of the comparator 1730, however, a small pump current ($I_{Pt/Rh}$) is flowing through the Pt—Rh cell. This pump current, depending on its direction, locally increases or decreases the oxygen content at the Pt—Rh electrode. This changes the voltage at that electrode. When one of the hysteresis points is reached, the output of the comparator switches from 1 to 0 (or from 0 to 1). This switching is clock synchronized by D-Flip-Flop 1736. The output of this D-Flip-Flop in turn causes the polarity of pump current $I_{Pt/Rh}$ to reverse direction via the electronic switch 1738. If no NOx is present, no net $O_2$ flow is needed through the Pt—Rh cell to maintain the same Nernst voltage as the $O_2$ reference cell. In this case, for a given time period, the output of the D-Flip-Flop 1736 is high as often as it is low. As a result, the average duty cycle of the NOx Pulse Density output is 50%. If NOx is present, some of the NOx is decomposed at the Pt—Rh electrode to O2 and N2. This causes a local excess of O2 molecules at the Pt—Rh electrode. In order to maintain the same Nernst voltage between Pt—Rh cell and O2 reference cell, this excess O2 must be removed. When current flows through the Pt—Rh cell from the air electrode 1616 to Pt—Rh electrode 1622, the cell behaves as an oxygen pump cell, pumping O2 ions from the Pt—Rh electrode to the air side. Therefore, for a given time period in this scenario, the electronic switch 1738 spends more time in its active position where it is switched to $I_{Pt/Rh}$. As a result, the average duty cycle is greater than 50%. The duty cycle depends on the NOx concentration and the chosen $I_{Pt/Rh}$ absolute value. In most circumstances, the relationship between the average duty cycle and the NOx concentration of the measurement gas is linear or nearly linear. In some situations, the sensor system is calibrated to accurately correlate the duty cycle to the NOx concentration. An example of a suitable calibration technique includes adjusting one or more external resistors implemented within the sensor unit. Such a technique may be performed at the factory during manufacturing and establishes the slope of the linear relationship. In some situations, calibration may be omitted and determining whether calibration is needed depends on manufacturing tolerances, required accuracy of the NOx concentration measurement, and other factors.

The first comparator 1702 and flip-flop 1708 are an example of a first detection circuit 1756 that is configured to detect a first output signal generated by the primary electrochemical cell system in accordance with a first ion concentration within the measuring chamber and to control the first switching current source. The first switching current source is configured to direct the primary pump current through the primary electrochemical cell system between a first constant primary pump current and a second constant primary pump current to direct a first ion flow into a measuring chamber and out from the measuring chamber. The primary electrochemical system includes a measuring cell and a pump cell in this example. The second comparator 1730 and the second flip flop 1738 are an example of a second detection circuit 1758 configured to detect a second output signal generated by the secondary electrochemical cell system in accordance with the second ion concentration within the measuring chamber. The second detection circuit 1758 is therefore configured to generate a control signal 1740 based on a relationship between the first output signal and the second output signal. The second switching current source 1748 is configured to direct, in response to the control signal 1740, the secondary pump current through the secondary electrochemical cell system between the first constant secondary pump current and the second constant secondary pump current to direct a second ion flow into the measuring chamber and out from the measuring chamber.

Figure 18:
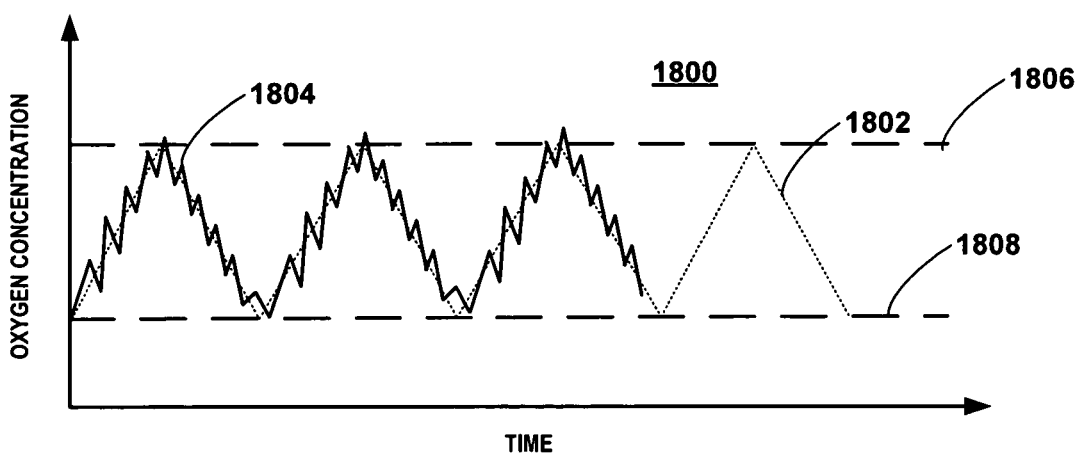
FIG. 18 is a graphical representation of an oxygen concentration within the measuring chamber.

FIG. 18 is a graphical representation 1800 of an oxygen concentration within the measuring chamber 1510. FIG. 18 shows general relationships between values and the depicted amplitudes and frequencies may not necessarily be to scale and may not depict actual measured quantities. A first ion concentration curve 1802 represents a first ion concentration 1420 such as the general oxygen concentration within the measuring chamber 1510. A second ion concentration curve 1804 represents a second ion concentration 1422 such as the local oxygen concentration near the Pt/Rh electrode 1622. In most situations, the curves 1802, 1804 are proportional to the primary and second output signals 1416, 1418 such as the cell voltages of the oxygen measuring cell 1504 and the nitrogen sensing cell 1506. The first ion concentration curve 1802 varies between an oxygen concentration upper threshold 1806 and an oxygen concentration lower threshold 1808 although the thresholds may be exceeded in some circumstances. The oxygen concentration lower threshold 1808 may be equal to, or very near, zero in some situations. The oxygen concentration lower threshold 1808, therefore, corresponds to the lower threshold applied by the first comparator when comparing the oxygen measuring cell voltage 1704 to the reference voltage 1706. The oxygen concentration upper threshold 1806 corresponds to the upper threshold applied by the first comparator 1702.

Figure 19:
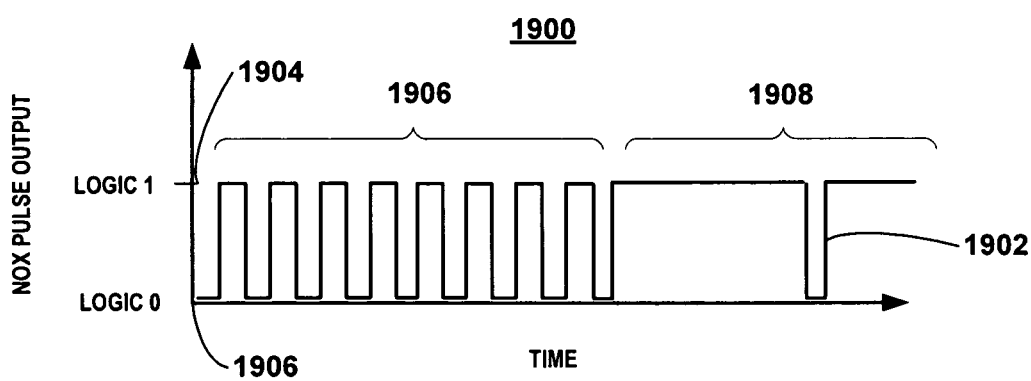
FIG. 19 is a graphical representation of a NOx pulse output curve.

FIG. 19 is a graphical representation 1900 of a NOx pulse output curve 1902. FIG. 19 shows general relationships between values and the depicted amplitudes and frequencies may not necessarily be to scale and may not depict actual measured quantities. The NOx pulse output curve 1902 varies between logic high 1904 and logic low 1906 levels and has a duty cycle dependent on the NOx concentration within the measuring chamber 1510. The second flip-flop output 1740 may provide the NOx pulse output curve 1902. A first portion 1906 of the NOx pulse output curve 1902 represents the output of the second flip flop 1736 when no NOx are present in the measuring chamber. For the first portion 1906 the duty cycle is 50 percent. A second portion 1908 represents the second flip-flop output 1740 when NOx are present. The second portion has a duty cycle that is greater than 50 percent since, at a given clock rate, the number of 1s is greater than the number of 0s within a time period.

Figure 20:
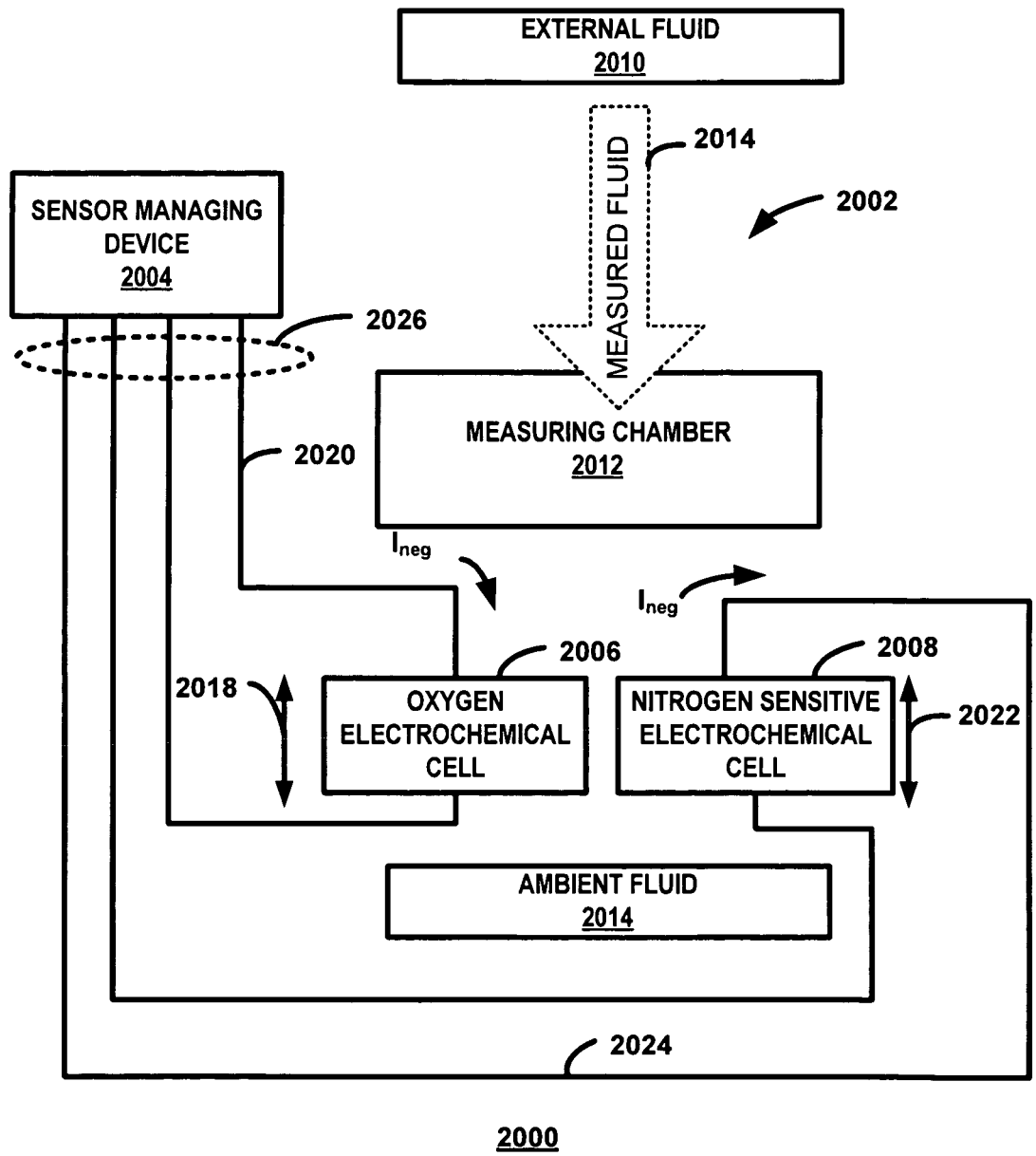
FIG. 20 is a block diagram of a sensor system including a NOx sensor connected to a sensor managing device where the NOx sensor includes a single oxygen electrochemical cell for performing the functions of the oxygen sensor cell and the oxygen measuring cell.

FIG. 20 is a block diagram of a sensor system 2000 including a NOx sensor 2002 connected to a sensor managing device 2004 where the NOx sensor 2002 includes a single oxygen electrochemical cell 2006 for performing the functions of the oxygen sensor cell and the oxygen pump cell. Accordingly, the NOx sensor 2002 is an implementation of the ion sensor 1400 where the primary electrochemical system 1404 includes the oxygen electrochemical cell 2006 and where the secondary electrochemical system 1406 includes the nitrogen sensitive electrochemical cell 2008. An external fluid 2010 is received through a diffusion gap, diffusion layer, or other opening into the measuring chamber 2012 as a measured fluid 2014. The oxygen electrochemical cell 2006 and the nitrogen sensitive electrochemical cell 2008 are exposed to ambient fluid 2016 and the measuring chamber 2012. Although the sensor 2002 may be designed to work with a variety of fluids including gases and liquids, typical implementations include configurations for measuring gas concentrations. An example of a suitable implementation includes installing the NOx sensor 2002 within an exhaust system of a combustion engine in order to measure the NOx concentration of exhaust gas. In such systems, therefore, the external fluid 2010 is an exhaust gas and the ambient fluid 2014 is ambient air. The sensor system 2000 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

A sensor measuring device 2004 varies a pump current 2018 through the oxygen electrochemical cell 2006 between a first constant current and a second constant current in accordance with a cell voltage 2020 at the oxygen electrochemical cell 2006. The oxygen electrochemical cell 2006 moves ions between the measuring chamber 2012 and an ambient fluid 2016, such as air, based on the pump current 2018 flowing through the oxygen electrochemical cell 2006. The sensor measuring device 2004 also varies a pump current 2022 through the nitrogen sensitive electrochemical cell 2008 between a first constant current and a second constant current in accordance with a relationship between the cell voltage 2020 at the oxygen electrochemical cell 2006 and the cell voltage 2024 at the nitrogen sensitive cell 2008. The nitrogen electrochemical cell 2006 reduces NOx into oxygen ions and nitrogen ions and moves the oxygen ions between the measuring chamber 2012 and an ambient fluid 2016, such as air, based on the pump current 2022 flowing through the nitrogen sensitive electrochemical cell 2008.

The sensor measuring device 2004 extracts the Nernst voltage of the oxygen electrochemical cell 2006 from the total cell voltage 2020 in order to provide a reference for comparison to the cell voltage 2024 of the nitrogen sensitive electrochemical cell 2008. The internal resistance of the oxygen electrochemical cell is determined and subtracted from the cell voltage to obtain the Nernst voltage of the oxygen electrochemical cell 2006 which indicates the oxygen ion concentration within the first region of the measured fluid within the measuring chamber. The Nernst voltage of the oxygen electrochemical cell 2006, therefore, is an example of the first output signal 1416 of FIG. 14.

During operation, the sensor managing device 2004 varies the cell current 2012 through the oxygen electrochemical cell 2006 between a first constant pump current and a second constant pump current. The oxygen measuring cell output signal 2020 is monitored by the sensor managing device 2004 and used to determine when to switch the direction of the cell current 2018. When the oxygen measuring cell output signal 2020 reaches an upper threshold, the cell current 2018 is reversed from a positive constant pump current that pumps oxygen ions into the measuring chamber 2012 to a negative constant pump current that pumps oxygen ions out from the measuring chamber 2012. When the oxygen measuring cell output signal 2020 reaches a lower threshold, the cell current 2018 is switched back to the positive pump current. The lines illustrating the connections between the sensor managing device 2004 and the sensor are functional representations of signals and the actual number of physical connections depends on the particular implementation. Some of the connections may be to ground or other voltage potential. As discussed with reference to FIG. 22, for example, the air electrode is connected to ground and only two electrical connections (other than ground) are made between the sensor and the sensor managing device.

The nitrogen sensitive electrochemical cell 2008 is any electrochemical cell that reduces oxide of nitrogen (NOx) into nitrogen and oxygen and that generates a nitrogen cell output signal 2024 that indicates a local oxygen ion concentration at the cell 2008. For the example discussed with reference to FIG. 21 below, the nitrogen sensitive electrochemical cell 2008 includes a platinum and rhodium (Pt/Rh) electrode exposed to the measuring chamber 2012 that catalytically reduces the NOx to $N_2$ and $O_2$. Where NOx is present, the local oxygen concentration at the NOx cell electrode is higher than the oxygen concentration within the rest of the measuring chamber 2012. This local oxygen concentration, therefore, is an example of the second ion concentration 1422 of FIG. 14. The sensor managing device 2004 compares the nitrogen cell output signal 2024 to the Nernst contribution of the oxygen measuring cell output signal 2020 and applies a nitrogen cell pump current 2022 through the nitrogen sensitive electrochemical cell 2008. The nitrogen cell pump current 2022 pumps oxygen ions out from the measuring chamber to the ambient air 2014 when the nitrogen cell pump current 2022 is negative and pumps oxygen into the measuring chamber 2012 from the ambient air 2012 when the nitrogen cell pump current 2022 is positive. The nitrogen cell pump current 2022 is reversed when the difference between the Nernst portion of the oxygen cell output signal and the nitrogen cell output signal 2024 reaches an upper threshold and when it reaches a lower threshold. Accordingly, the function (wave form) of the control signal for switching the nitrogen cell pump current 2022 indicates the NOx concentration of the measured fluid 2014. The concentration may be determined by observing other values or signals. The duty cycle of the nitrogen cell pump current 1524 may be analyzed to determine nitrogen concentration, for example. Accordingly, any value derived or related to the difference between the oxygen measuring cell output signal 2020 (first output signal 1416) and the nitrogen sensitive cell output signal 2024 (second output signal 1418) may be used to determine nitrogen concentration.

As compared to the NOx measuring system of FIG. 15, the NOx measuring system 2000 described with reference to FIG. 20 uses a single electrochemical cell for pumping and measuring ions rather then separate cells. As mentioned above, the Nernst voltage must be extracted from the total cell voltage of the in order to provide a reference for determining the NOx concentration.

As described above, the electrochemical cell has an internal resistance. When a constant electrical current is forced through the oxygen electrochemical cell, a voltage is created at the cell which is the sum of the Nernst voltage and the voltage drop (resistance voltage) created by the internal resistance of the electrochemical cell. The internal resistance is the real impedance of the cell sometimes referred to as the Ohmish impedance. The resistance voltage ($V_R$) results from the pump current flowing through the internal resistance. A Nernst voltage indicates the oxygen concentration in the measuring chamber and is equal to the difference between the total electrochemical cell voltage ($V_{CELL}$) and the resistance voltage ($V_R$). The Nernst voltage, therefore, can be calculated by subtracting the resistance voltage ($V_R$) from the electrochemical voltage ($V_{CELL}$). In the example of FIG. 20, the sensor managing device 2004 continually switches the pump current 2018 between positive and negative constant currents, measures the cell voltage, and determines the oxygen concentration based on the Nernst voltage by subtracting the resistance voltage ($V_R$). The sensor managing device 2004 may include a current managing unit and a computing device where the current managing unit controls the current flow and measures the cell voltage.

Accordingly, the measured voltage of the oxygen electrochemical cell is used to trigger the reversal of pump current through the oxygen electrochemical cell. For example, if during a positive pump current ($I_P$) the Nernst voltage ($|V_{CELL}|-|R*I_P|$)>=0.5 Volt, then the pump current ($I_P$) is reversed, R (internal resistance) is calculated as described below, and the process continues with a negative constant pump current until the Nernst Voltage is <=0.4V. Then the pump current ($I_P$) is polarized back to positive and so on. In this example, the Hysteresis voltage is 0.1V (0.5V–0.4V). Different Hysteresis Voltages can be used.

An example of a suitable technique of determining the internal resistance (R) of the oxygen electrochemical cell includes measuring the voltage change at the cell at the transition point between positive and negative current and/or between negative and positive current through the cell. Since the pump current is switched between constant positive and negative currents, the resistance is calculated based on Ohms law.

The internal resistance is dependent on the temperature of the electrochemical cell. At a polarity reversal of the pump current, the cell has not had time to react and has not pumped any oxygen in the new direction. So the oxygen concentration difference, which determines the Nernst voltage, has not yet changed by a significant amount. Accordingly, the voltage change at the cell is at least mostly caused by the change in current. Based on the difference in current and difference in voltage, the internal resistance is determined based on the relationship $R_{CELL}=\Delta V_{CELL}/\Delta I_P$, where $\Delta V_{CELL}$ is the difference in voltage at the cell and $\Delta IP$ is the difference in pump current. The internal resistance $R_{CELL}$ is used to determine the voltage drop ($V_R$) due to the internal resistance $R_{CELL}$ based on the Ohms Law, $V_R=R_{CELL}*I_P$. The resistance voltage ($V_R$) is subtracted from the actual voltage ($V_{CELL}$) on the oxygen electrochemical cell to provide the reference for comparing to the nitrogen cell output 2024. In most applications, the voltage change $\Delta V_{CELL}$ can be measured up to a few microseconds before and after the current transition. The difference between the voltage immediately before the polarity reversal and immediately after is the $\Delta V_{CELL}$ voltage change. An example of a suitable technique for measuring the $\Delta V_{CELL}$ voltage includes using a sample and hold circuit.

An example of suitable sensor managing device 2004 includes an apparatus that is configured to connect to the measuring cell system (oxygen electrochemical cell 2006 and the nitrogen sensitive electrochemical cell 2008) through an interface 2026 and includes circuitry forming a current managing unit and a computing device. The interface 2026 may include an electrical connector, direct cable connection, or other electrical contact arrangement for conveying signals between the sensor 2002 and the sensor managing device 2004.

Figure 21:
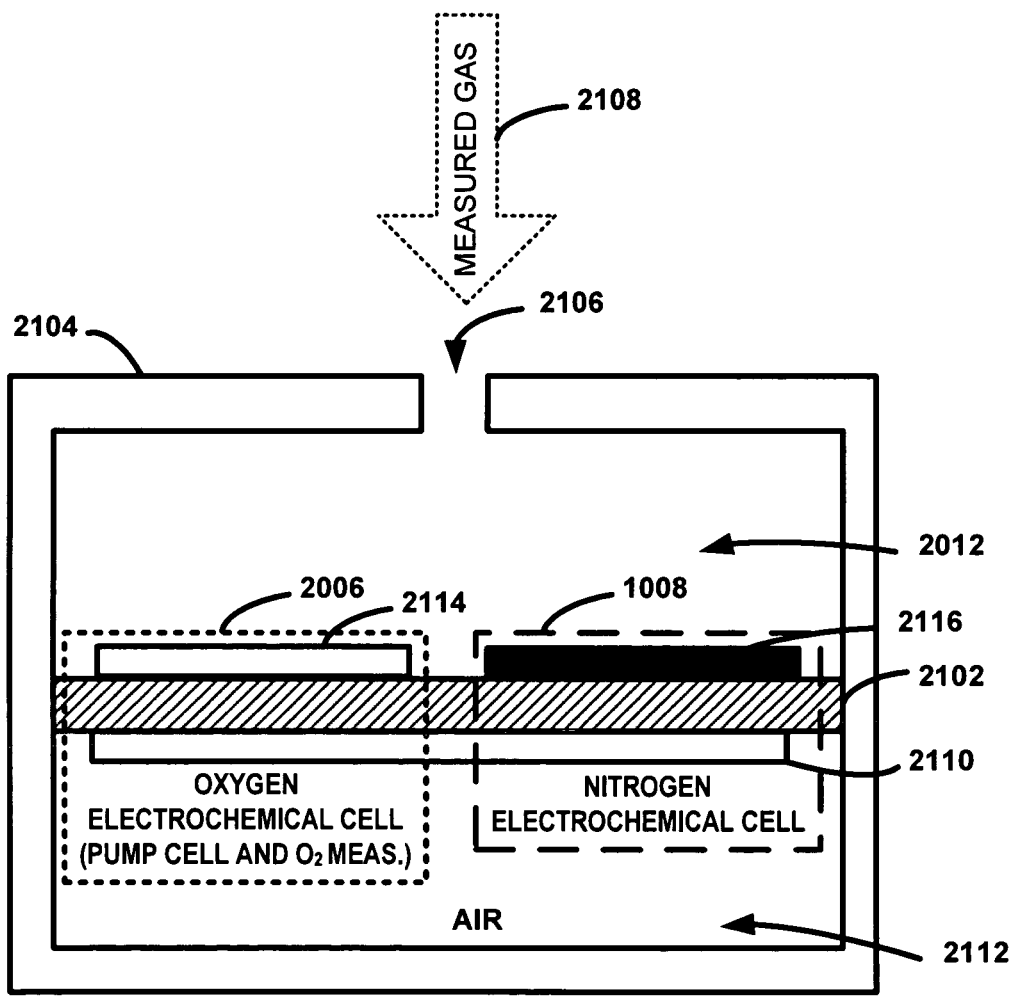
FIG. 21 is a block diagram of a cross section of a NOx sensor for measuring ion concentrations in gases which is an example of an implementation of the NOx sensor of FIG. 20.

FIG. 21 is a block diagram of a cross section of a NOx sensor 2100 for measuring ion concentrations in gases which is an example of an implementation of the NOx sensor 2002 of FIG. 20. Accordingly, the NOx sensor 2100 is an example of the NOx sensor 2002 where the NOx sensor 2100 can be used within the exhaust system of a combustion engine. The sensor 2100 may also be used within other systems and for other uses. Examples of other uses include detection alarms and medical devices.

The NOx sensor 2100 includes a single laminated zirconium dioxide (ZrO2) ceramic layer 2102. A space between the layer 2102 and a chamber housing 2104 forms the measuring chamber 2012. A hole 2106 within the chamber housing 2104 forms a diffusion gap for receiving a measured gas 2108 (measured fluid 2014). The diffusion gap may be a diffusion gap, diffusion layer, or other opening into the measuring chamber.

A single platinum electrode (air electrode) 2110 is disposed on the ZrO2 layer 2102 such that the air electrode 2110 is opposite the measuring chamber 2012 and exposed to ambient air 2112 (ambient fluid 2014). Another platinum electrode (oxygen electrode) 2114 is disposed on the layer 2102 opposite the air electrode 2110 and is exposed to the measured gas 2108 with the measuring chamber to form the oxygen electrochemical cell 2006 with the air electrode 2110 and the ZrO2 layer 2102. A platinum/rhodium (Pt/Rh) electrode 2116 is disposed on the measuring chamber side of the ZrO2 layer 2102 and is also exposed to the measured gas 2108 within the measuring chamber 2012. The platinum/rhodium (Pt/Rh) electrode 2116 forms the nitrogen sensitive electrochemical cell 2008 with the air electrode 2110 and the ZrO2 layer 2102. Accordingly, the oxygen electrode 2114, air electrode 2110, and ZrO2 layer 2102 form the oxygen electrochemical cell 2006 and the Pt/Rh electrode 2116, air electrode 2110, and ZrO2 layer 2102 form the nitrogen sensitive cell 2008.

An electrical current 2018 through the oxygen electrochemical cell 2006 transports oxygen ions in an opposite direction to the direction of the electrical current. The nitrogen sensitive cell 2008 is responsive to nitrogen and oxygen. The Pt/Rh electrode 2116 catalytically reduces oxides of nitrogen (NOx) into Nitrogen (N2) and oxygen (O2). This mechanism causes a local enrichment of oxygen content (partial pressure) at the surface of the Pt/Rh electrode 2116. Accordingly, the local concentration of oxygen near the Pt/Rh electrode 2116 increases when NOx are present. The Nernst voltage between the air electrode 2110 and the Pt/Rh electrode 2116 is lower than the oxygen measuring cell output voltage 2020 (first output signal 1416) when NOx are present. The local oxygen concentration near the Pt/Rh electrode 2116 is an example of the second ion concentration 1422 of FIG. 14.

Figure 22:
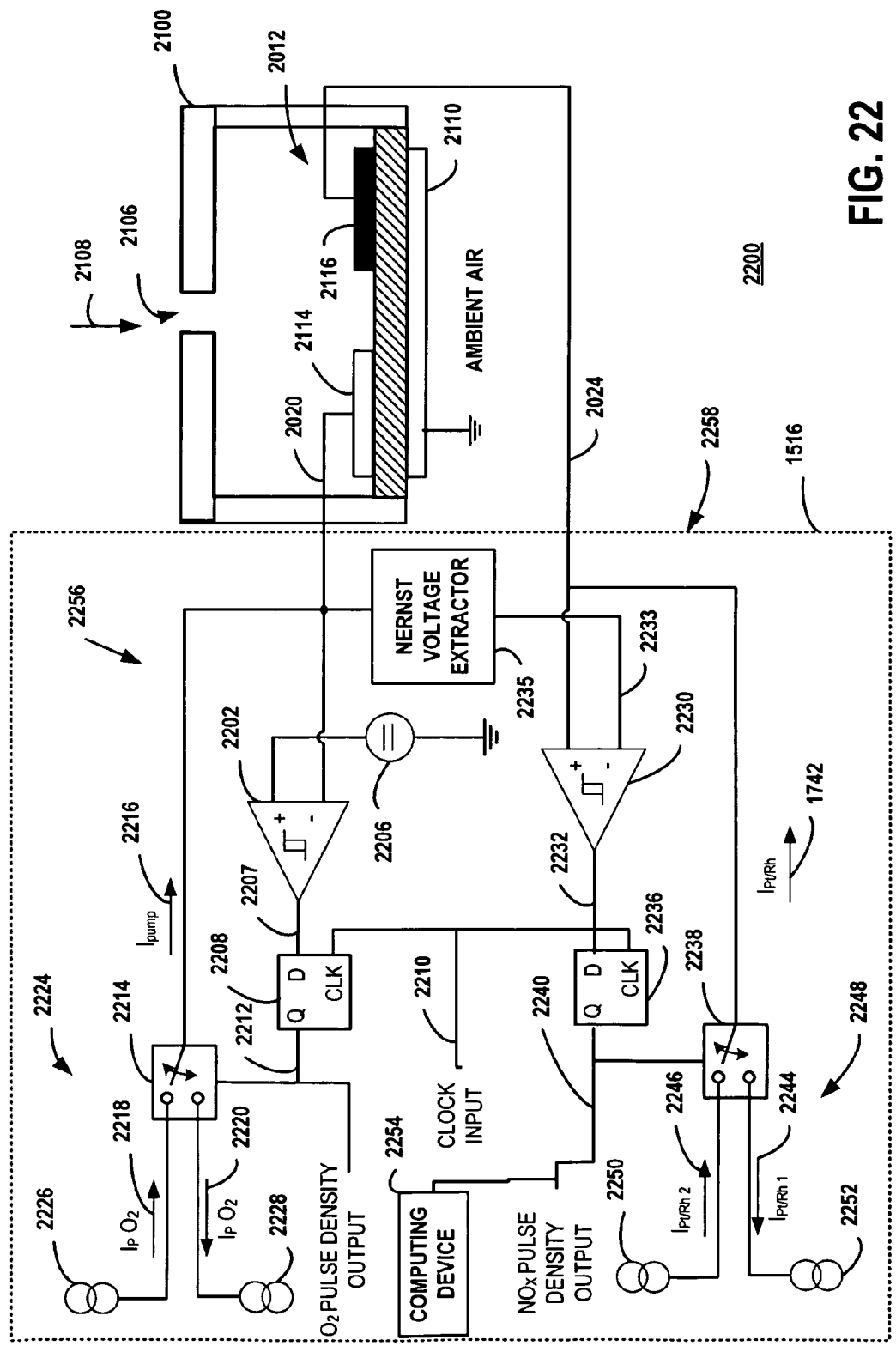
FIG. 22 is a schematic function diagram of a NOx measuring system including the sensor managing device 2004 connected to the NOx sensor of FIG. 21.

FIG. 22 is a schematic function diagram of a NOx measuring system 2200 including the sensor managing device 2004 connected to the NOx sensor 2100 of FIG. 21. The NOx measuring system 2200 may be implemented using any combination of hardware, software and firmware. Various functions and operations of the functional blocks described with reference to FIG. 22 may be implemented in any number of devices, circuits or elements. Any of the functional blocks may be integrated in a single device and the functions of the blocks may be distributed over several devices, circuits and elements. Some of the functional blocks may be omitted in some instances. For example, the flip-flops may be omitted since the operation of these devices is inherent in the counting of output pulses by the counters. FIG. 22, therefore, is a diagram of an example of an implementation of the sensor 2100 as connected within a measurement system. The various elements, devices, values, signals, and functions described with reference to FIG. 22 may differ for other measurement systems using other implementations of the sensors 1400, 2002, 2100, depending on the particular structure, use, environment and requirements of the particular measurement system and sensor.

A first comparator 2202 with hysteresis continuously compares the oxygen measuring cell voltage 2204 across the oxygen electrochemical cell 2006 to a reference voltage 2206. For this example, the reference voltage 2206 is −450 mV. When the oxygen measuring cell voltage 2204 drops below a lower threshold, the first comparator output 2207 is a logic high signal and when the oxygen measuring cell voltage 2020 rises above an upper threshold, the first comparator output is a logic low signal. The upper and lower thresholds are determined by the hysteresis of the comparator and are selected to correspond to oxygen concentration thresholds within the measuring chamber 2012. The thresholds also take into account the contribution of the voltage due to the internal resistance of the oxygen electrochemical cell. Accordingly, the hysteresis of the first comparator 2202 in the system of FIG. 22 is larger than the hysteresis of the first comparator 1702 of the system 1700 discussed with reference to FIG. 17.

The first comparator output 2207 is processed by a first flip-flop (FF1) 2208 such that a clock input 2210 gates a FF1 output 2212 of the first flip-flop 2208. The FF1 output 2212 controls a first current switch 2214 which directs a oxygen cell pump current 2216 through the oxygen electrochemical cell 2006 between a first constant pump current 2218 and a second constant pump current 2220. For this example, the first and second constant pump currents are equal in magnitude but have an opposite polarity.

Therefore, after the first comparator output drops below the lower threshold (−½ hysteresis), the first flip flop output 2212 is set to high at the next clock cycle. The resulting high FF1 output sets the first current switch 2214 to direct a constant positive pump current 2218 through the oxygen electrochemical cell 2006. In this state, the electrochemical cell 2006 pumps oxygen from the oxygen electrode 2114 through the oxygen electrochemical cell 2006 and into the measuring chamber 2012 from the ambient air. The first current switch 2214 remains in this position until switched by the FF1 output 2212. When the oxygen measuring cell voltage 2204 reaches the upper threshold (+½ hysteresis), the first comparator 2202 generates a first comparator output signal that is a logic low. At the next clock cycle, the first flip-flop 2208 output changes to a logic low signal to switch the first current switch 2214 to the negative constant pump current 2220. In this state, oxygen is pump out from the measuring chamber 2012 to ambient air. FIG. 22 illustrates a switching current source 2224 that includes a positive current source 2226 and a negative current source 2228 that are directed by the first switch 2214. Any of numerous techniques and circuits can be used to achieve the functionality of the switching current source 2224 that switches from the first constant pump current 2218 to the second constant pump current 2220. Accordingly, for this example, the switching current source 2224 provides the primary pump current 1412 referred to in FIG. 14.

The second comparator 2230 with hysteresis generates an output 2232 based on a relationship between the Nernst voltage portion 2233 of the oxygen cell voltage 2024 (first output signal 1416) and the Pt/Rh cell output voltage 2234 (second output signal 1418). The second comparator 2230, therefore, compares the Nernst voltage produced by the oxygen electrochemical cell 2006 and not the total voltage across the cell in this example. A Nernst voltage extractor 2235 extracts the Nernst voltage from the total voltage of the oxygen electrochemical cell 2006. Accordingly, the Nernst voltage extracted by the Nernst voltage extractor 2235 is an example of the first output signal 1416 discussed with reference to FIG. 14. An example of suitable implementation of the Nernst voltage extractor 2035 includes a double sample circuit that samples the O2 reference voltage immediately prior to a polarity reversal of the pump current and immediately after a reversal. The difference between the two sample points is twice as large as the voltage caused by the pump current through the internal resistance of the cell.

The Nernst voltage extractor 2235 may be implemented using any of numerous techniques. An example of a suitable implementation includes using a sample-and-hold circuit. Sample-and-Hold circuits are typically implemented as part of analog to digital converter designs and consist of a capacitor, an electronic switch, and a low output impedance amplifier, such as an op-amp. A short sample pulse switches the switch on, which connects the capacitor to the amplifier output. This charges the capacitor to the output voltage. When the pulse disappears, the capacitor holds that charge to be read by the A/D conversion. In the Nernst extractor, the sample-and-hold capacitor is charged (sampled) with a very short pulse after the polarity of the current is reversed. At that time, the Nernst voltage has not had time to change. The total voltage at the cell is the sum of the Nernst Voltage ($V_{nernst}$) and the voltage caused by the pump current ($I_{pump}$) and the internal impedance of the cell ($V_{icell}$). $V_{icell}$ is, by Ohms law, $I_{pump} * R_{icell}$, where $R_{icell}$ is the cells impedance. As an example: if the current switched from positive to negative and, as a result, the total cell output voltage increases to reach an upper threshold voltage. Measuring the difference between upper threshold voltage and the voltage sampled immediately after the switch provides the information to calculate $V_{icell}$ and therefore $R_{icell}$, because the magnitude of $I_{pump}$ is known and fixed. The voltage at the cell before the switch ($V_{upperh}$) is $V_{nernstupper} + I_{pump} * R_{icell}$. The voltage at the capacitor after sampling right after the polarity reversal is $V_{sample} = V_{nernst} - I_{pump} * R_{icell}$ because the Nernst voltage $V_{nernst}$ did not have time to change in the very short time interval (microseconds) between polarity reversal of the current and sampling of the new cell voltage. Therefore, $V_{upperh} - V_{sample} = 2 * I_{pump} * R_{icell}$. This subtraction can be performed by a differential amplifier and does not need to be done digitally, although such an implementation may be preferred in some situations. Dividing this difference by 2, using a voltage divider, for example, yields $V_{icell}$, because $V_{icell} = I_{pump} * R_{icell}$. The new lower threshold for the comparison of the cell voltage is $V_{lowerh} = V_{nernstlower} - V_{icell}$. Because $I_{pump}$ is constant, $V_{icell}$ changes only with the impedance $R_{icell}$, which is temperature dependent. Thus, $V_{icell}$ can also be used for temperature regulation.

$V_{nernstupper}$ and $V_{nernstlower}$ are design parameters that are selected in accordance with the particular implementation and requirements. The parameters may be the same value in some circumstances. The additions and subtractions in these voltage calculations can be done digitally, or simpler with simple analog circuits such as differential and summing amplifiers using op-amps.

As described above, the PT/Rh electrode 2116 reduces NOx into N2 and O2 and generates and output 2024 based on the local oxygen concentration near the Pt/Rh electrode 2116. When NOx are present, the local oxygen concentration increases and the Nernst voltage between the air electrode 2110 and the Pt/Rh electrode 2116 is lower than then the Nernst voltage between the air electrode 2110 and the oxygen electrode 2114 of the oxygen electrochemical cell 2006. The second comparator 2230 continuously compares the Nernst voltage of the oxygen measuring cell 2006 (first output signal) and the nitrogen sensitive cell output 2024 (second output signal). Although there is a small contribution from the internal resistance, the current used in the nitrogen sensitive cell is a few orders of magnitude lower than the main oxygen cell pump current and, therefore, the voltage change is significantly small compared to the Nernst voltage. As a result a Nernst voltage extraction is not necessary for the nitrogen sensitive cell in most circumstances. The nitrogen sensitive cell can operate with fixed upper and lower thresholds that take the $V_{icell}$ into account. Since the temperature (and therefore $R_{icell}$) is typically regulated, $R_{icell}$ does not vary significantly.

When significant levels of NOx are present and the difference of the nitrogen sensitive cell voltage 2024 and the oxygen electrochemical cell voltage 2020 is below a lower threshold (e.g. the difference has magnitude above a threshold magnitude), the second comparator 2230 generates a second comparator output signal 2232 that is a logic low level. At the next clock cycle, a second flip-flop 2236 generates a FF2 output 1740 that is also a logic low level. The FF2 low signal sets the second current switch 2238 to direct the nitrogen sensitive cell current 2022 (secondary pump current 1414) through the nitrogen sensitive cell 2008 at a first constant nitrogen cell current 2244 (first constant secondary pump current). The first constant secondary pump current, therefore, is a relatively small negative pump current that flows from the air electrode 2110 to the Pt/Rh electrode 2116 for the example of FIG. 22. When the first constant secondary pump current is applied, the electrochemical cell forming the nitrogen sensitive cell 2008 functions as a pump cell to pump oxygen from the measuring chamber 2012 through the nitrogen sensitive cell 2008 to ambient air 2014. Accordingly, oxygen flow through the nitrogen sensitive cell 2008 is opposite in direction to the current flow 2042. When the oxygen is adequately depleted to establish a local oxygen concentration that is less than a threshold, the second comparator 2230 generates a second comparator signal 2232 that is a logic high level. Accordingly, the comparator 2230 detects that the nitrogen sensitive cell voltage and the Nernst portion 2233 of voltage across the oxygen measuring cell are the same voltage (or nearly the same voltage due to the hysteresis) and generates the high logic signal. At the next clock cycle, the second flip-flop 2236 provides a logic high signal to the second switch 2238 to switch the nitrogen sensitive cell current 2242 (secondary pump current 1414) from the first constant nitrogen sensitive cell current 2244 (first constant secondary pump current) to a second constant nitrogen sensitive cell current 2246 (second constant secondary pump current). The nitrogen sensitive cell current 2242, therefore, switches from a constant negative nitrogen sensitive cell current 2244 to a constant positive nitrogen sensitive cell current 2246 where the currents 2244, 2246 are relatively small compared to the pump cell currents 2218, 2220 through the oxygen electrochemical cell 2006. The relatively small positive current through the nitrogen sensitive cell 2008 pumps oxygen from the air 2014 into the measuring chamber 2012. The local oxygen concentration near the Pt/Rh electrode 2116 continues to increase due to the positive secondary pump current and the contribution of any catalytically reduced NOx until the lower threshold is reached and the process repeats. FIG. 22 illustrates a switching current source 2248 that includes a positive current source 2250 and a negative current source 2252 that are directed by the second switch 2238. Any of numerous techniques and circuits can be used to achieve the functionality of the switching current source 2246 that switches from the first constant nitrogen sensitive cell current 2244 to the second constant nitrogen sensitive cell current 2246. Accordingly, the switching current source 2248 provides the secondary pump current 1414 referred to in FIG. 14.

The NOx pulse density output of the second flip-flop output signal 2240 indicates the concentration of NOx in the measuring chamber 2012. Where there is no NOx present, the number of logic highs (1s) and logic lows (0s) of the signal 2240 are equal for a given time period. This occurs since there is no need to pump out any additional oxygen produced by the Pt/Rh electrode 2116. As the NOx concentration increases, more oxygen is catalytically produced and pumped out and the number of 1s increases relative to the number if 0s over a given time period. Accordingly, the duty cycle of the NOx pulse density output 2240 is a measurement of NOx.

The various, signal polarities, magnitudes, logic levels and frequencies are selected in accordance with the particular implementation. Some examples of suitable values include the following. An example of a suitable secondary pump current includes a secondary pump current magnitude that is 2 to 3 times orders of magnitude lower than then primary pump current. Such a selection is often suitable since typical NOx content within the measuring chamber 2012 is many orders lower than the oxygen content. The hysteresis of the first comparator 2202 is chosen such that the oscillation of the circuit controlled by the comparator 2202 is on the order of 50 to 100 Hz. The hysteresis of the second comparator 2230 is chosen such that the oscillation of the NOx circuit controlled by the second comparator 2230 is on the order of one to two kilohertz (1-2 KHz). As explained above, the hysteresis of the second comparator 2230 is selected to compensate for the voltage ($V_R$) across the Pt/Rh cell due to the resistance of the cell. Since $I_{pump2}$ is a few orders of magnitude smaller than $I_{pump1}$, $V_R$ is also much smaller. This contribution is small enough that the upper and lower threshold of the Nernst voltage comparison can be adjusted by adding $R_{cell}*I_{pump2}$ to the upper threshold of comparison and subtracting $R_{cell}*I_{pump2}$ from the lower threshold. With typical $R_{cell}$ of about 80 Ohms and $I_{pump2}$ on the order of 10 micro-Amps, the adjustment is approximately 0.8 mV and, therefore, relatively small.

Therefore, the measuring system 2200 measures the NOx content of an exhaust gas 2010. A measured gas 21080 is diffused through a single diffusion gap 2106 into the measuring chamber 2012. A primary electrochemical system directs and measures oxygen within the measuring chamber 2012 while a secondary electrochemical system operates in parallel to measure NOx. The secondary electrochemical system reduces the NOx into N2 and O2 and manages flow of O2 into and out from the measuring chamber 2012 in parallel to the flow of oxygen managed by the primary electrochemical system. This mechanism provides several advantages over conventional NOx sensors as discussed above.

The first comparator 2202 and flip-flop 2208 are an example of a first detection circuit 2256 that is configured to detect a first output signal generated by the primary electrochemical cell system in accordance with a first ion concentration within the measuring chamber and to control the first switching current source 2224. The first switching current source 2224 is configured to direct the primary pump current through the primary electrochemical cell system between a first constant primary pump current and a second constant primary pump current to direct a first ion flow into a measuring chamber and out from the measuring chamber. The primary electrochemical cell system is a single electrochemical cell in this example that produces a single cell output. The second comparator 2230 and the second flip flop 2236 are an example of a second detection circuit 2258 configured to detect a second output signal generated by the secondary electrochemical cell system in accordance with the second ion concentration within the measuring chamber. The second detection circuit 2258 is therefore configured to generate a control signal 2240 based on a relationship between the first output signal and the second output signal. The second switching current source 2248 is configured to direct, in response to the control signal 2240, the secondary pump current through the secondary electrochemical cell system between the first constant secondary pump current and the second constant secondary pump current to direct a second ion flow into the measuring chamber and out from the measuring chamber.

Figure 23:
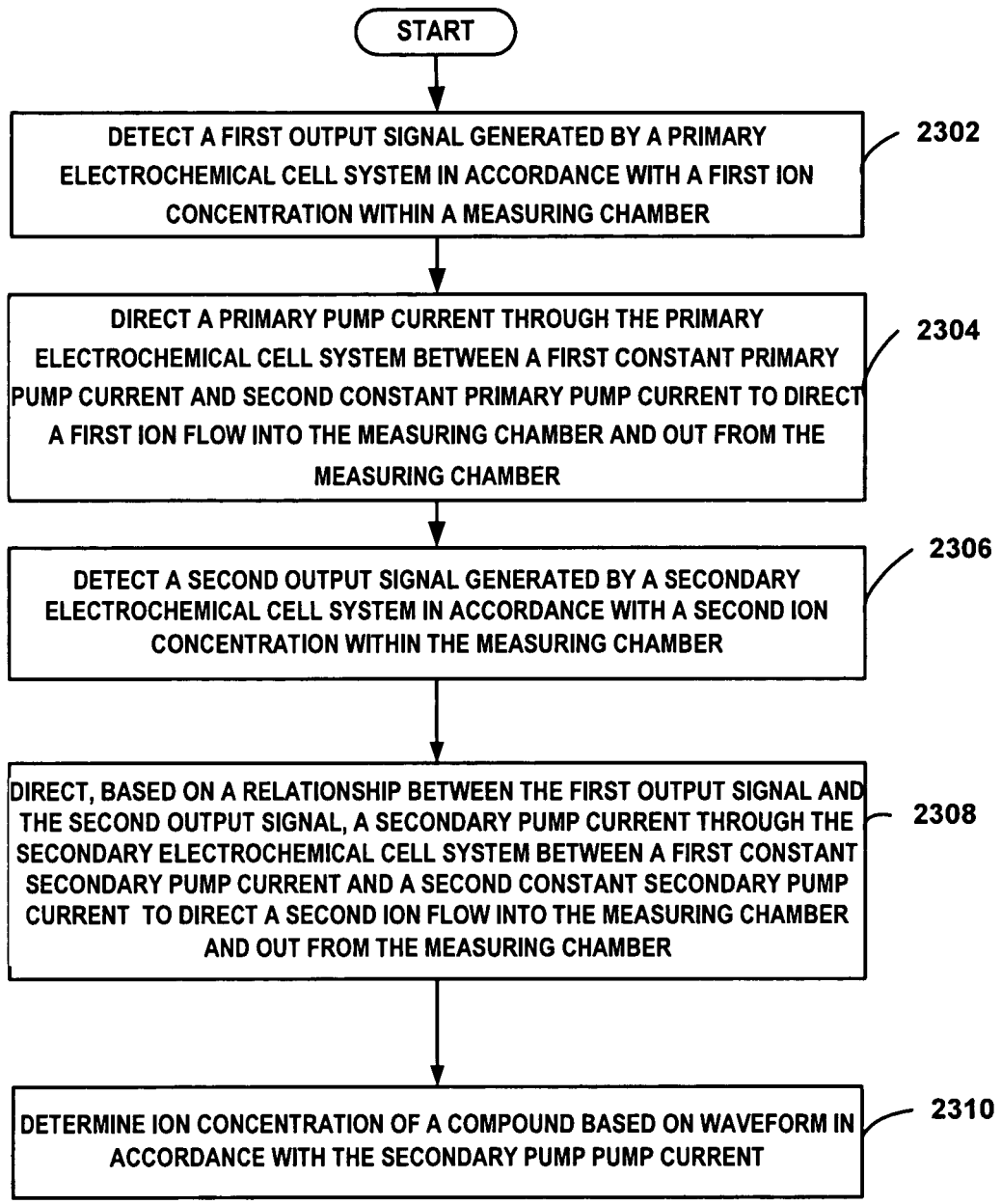
FIG. 23 is flow chart of a method of managing a sensor having a primary electrochemical cell system and a secondary electrochemical cell system.

FIG. 23 is flow chart of a method of managing a sensor having a primary electrochemical cell system and a secondary electrochemical cell system. Although the method may be performed by any combination of hardware, software, and/or firmware, the method is performed in a sensor managing device in this example.

At step 2302, the first output signal is detected. The first output signal is generated by the primary electrochemical cell system in accordance with the first ion concentration within the measuring chamber. The first comparator receives the first output signal and compares it to a reference voltage to generate a control signal for controlling the first switching current source. Where the primary electrochemical cell system includes a separate pump cell and measuring cell, the first output signal is generated by the measuring cell. Where the primary electrochemical cell system includes a single electrochemical cell, the first output signal is single cell output voltage generated by the single electrochemical cell.

At step 2304, the primary pump current is directed through the primary electrochemical cell system between the first constant primary pump current and the second constant primary pump current. The first switching current source directs the current in response to the control signal produced by the first comparator and "clocked" by the first flip flop. The varying current directs a first ion flow into the measuring chamber and out from the measuring chamber. Where the primary electrochemical cell system includes a separate pump cell and measuring cell, the primary pump current is the current through the pump cell. Where the primary electrochemical cell system includes a single electrochemical cell, the primary pump current is the current through the single electrochemical cell.

At step 2306, the second output signal is detected. The second output signal is generated by the secondary electrochemical cell system in accordance with the second ion concentration within the measuring chamber. The second comparator receives the second output signal and compares it to either the first output signal or to Nernst voltage portion of the first output signal to generate a control signal for controlling the second switching current source. Where the primary electrochemical cell system includes a separate pump cell and measuring cell, the second output signal is compared to the first output signal. Where the primary electrochemical cell system includes a single electrochemical cell, the second output signal is compared to the Nernst portion of the first output signal which is provided by the Nernst voltage extractor.

At step 2308, the secondary pump current is directed through the secondary electrochemical cell system based on a relationship between the first output signal and the second output signal. The secondary pump current is varied between the first constant secondary pump current and the second constant secondary pump current. The second switching current source directs the current in response to the control signal produced by the second comparator and "clocked" by the second flip flop. The varying current directs a second ion flow into the measuring chamber and out from the measuring chamber.

At step 2310, the ion concentration of the compound is determined. The computing device evaluates a waveform that is in accordance with the secondary pump current to determine the concentration of one of the ions of the compound. The secondary electrochemical cell system reduces the compound into the ion of the element that is pumped into and out from the measuring chamber and into another ion for which the concentration is to be calculated. For NOx compounds, the PT/Rh electrode reduces the NOx into N and O ions forming a local concentration of O ions near the electrode. Accordingly, the pumped ion (O) has a first concentration in a first region within the measuring chamber and a second concentration within a second region within the measuring chamber where the second region is closer to the electrode than the first region. The local concentration of the ion is determined by evaluating the control signal 1740 for controlling the second switching current source. Any signal, however, that indicates the duty cycle of the control signal (or secondary pump current) can be evaluated to determine concentration. For example, the secondary pump current may be directly evaluated in some cases. Also, the output of the second comparator may be evaluated.

Figure 24:
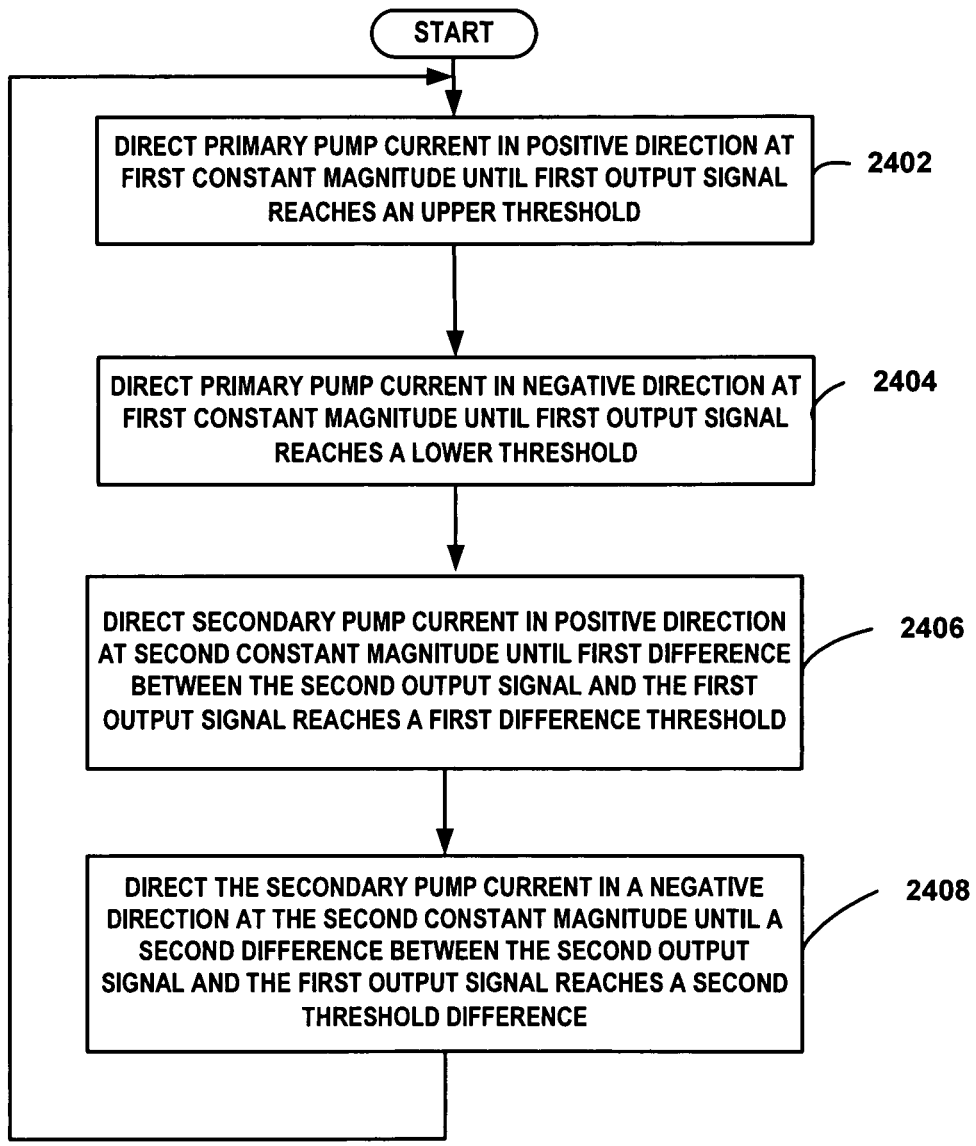
FIG. 24 is flow chart of a method of managing currents in the sensor including a primary electrochemical cell system and a secondary electrochemical cell system

FIG. 24 is flow chart of a method of managing currents in the sensor including a primary electrochemical cell system and a secondary electrochemical cell system.

At step 2402, the primary pump current is directed in a positive direction at a first constant magnitude until the first output signal reaches an upper threshold. For the example, the switching current source maintains a positive primary pump current until the first comparator detects that the first output voltage has reaches the upper threshold at which time the comparator output causes (through the flip-flop) the switching current source to change direction.

At step 2404, the primary pump current is directed in a negative direction at the first constant magnitude until the first output signal reaches a lower threshold. The switching current source maintains a negative primary pump current until the first comparator detects that the first output voltage has reaches the lower threshold at which time the comparator output causes (through the flip-flop) the switching current source to change direction again and pump current in the positive direction and the first magnitude. Steps 2402 and 2404 continue to repeat.

At step 2406, the secondary pump current is directed in a positive direction at a second constant magnitude until a first difference between the second output signal and the first output signal reaches a first difference threshold. The second switching current source maintains a positive secondary pump current until the second comparator detects that the difference between the second output signal and the first output voltage has reached a difference threshold. Where the primary electrochemical cell system includes a single electrochemical cell, the Nernst voltage portion of the first signals is extracted and compared to the second output voltage. When the first difference threshold is reached, the second comparator output causes (through the second flip-flop) the second switching current source to change direction.

At step 2408, the secondary pump current is directed in a negative direction at the second constant magnitude until a second difference between the second output signal and the first output signal reaches a second difference threshold. The second switching current source maintains a negative secondary pump current until the second comparator detects that the difference between the second output signal and the first output voltage has reaches a second difference threshold. Where the primary electrochemical cell system includes a single electrochemical cell, the Nernst voltage portion of the first signals is extracted and compared to the second output voltage. When the second difference threshold is reached, the second comparator output causes (through the second flip-flop) the second switching current source to change direction again. The order of steps 2402, 2404, 2406, and 2408 may vary during operation. For example, since the frequency of oscillation of the primary pump current is much lower than the frequency of the secondary pump current, steps 2406 and 2408 may repeat several times before step 2404 is executed.

Figure 25:
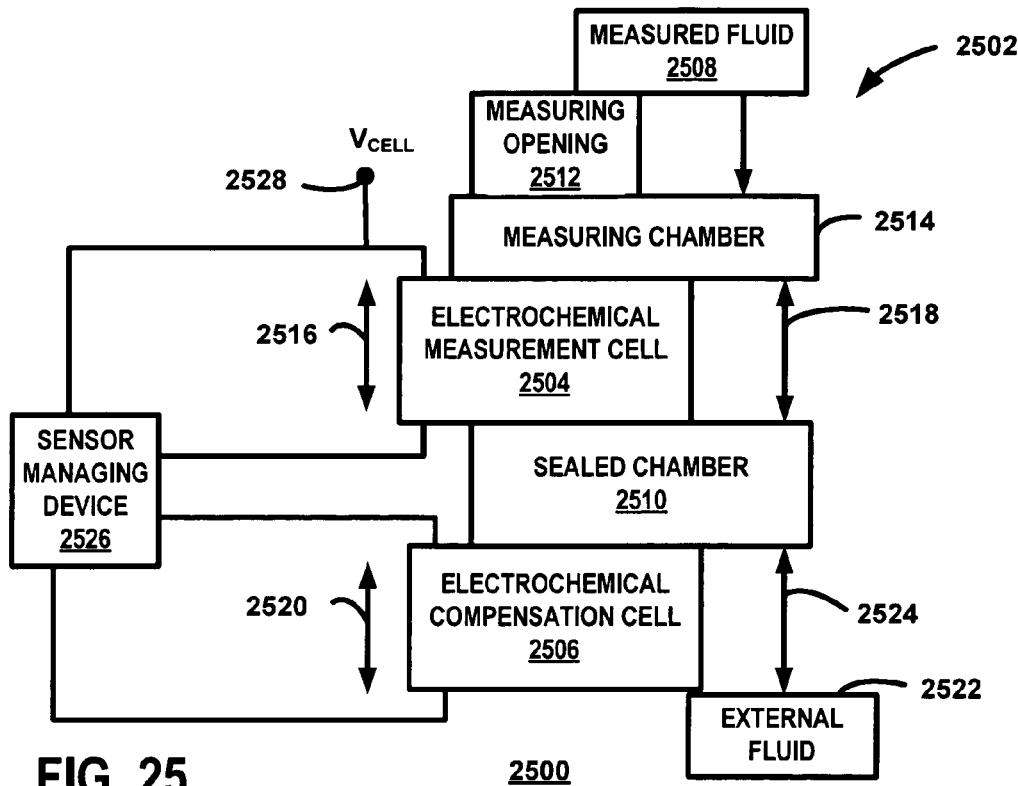
FIG. 25 is a block diagram of a sensor system including a sealed chamber sensor.

FIG. 25 is a block diagram of a sensor system 2500 including a sealed chamber sensor 2502. The sealed chamber sensor 2502 includes an electrochemical measuring cell 2504 and an electrochemical compensation cell 2506 where both cells 2504, 2506 are connected to a sealed chamber 2508. A measured fluid 2510 such as measured gas or liquid, is received through a measuring opening 2512 into a measuring chamber 2514. The measuring opening 2512 may be a diffusion gap, diffusion layer, or other membrane or orifice that allows measured fluid 2508 to enter the measuring chamber 2514. The electrochemical measuring cell 2504 operates in accordance with the description of the operation of the electrochemical cell 1006 discussed above. The sealed chamber sensor 2500, however, is less susceptible to adverse performance resulting from contamination from dirt, water, and other environmental elements. The electrochemical compensation cell 2506 insolates the electrochemical measuring cell 2504 from direct exposure to these contaminates.

A measuring cell current 2516 is directed through the electrochemical measuring cell 2504 to move ions between the sealed chamber 2510 and the measuring chamber 2512. Accordingly, a first ion flow 2518 corresponds to the measuring cell current 2516. A compensation cell current 2520 directed though the electrochemical compensation cell 2506 moves ions between the sealed chamber 2508 and an external fluid 2522 which may be ambient liquid, ambient air, exhaust gas or other gas or liquid depending on the particular implementation of the sensor 2500. The external fluid 2522 has an adequate ion concentration to allow sufficient ion flow into the sealed chamber 2510 from the external fluid 2522 through the electrochemical compensation cell 2506. Accordingly, a second ion flow 2524 corresponds to the compensation cell current 2520.

All ions entering and exiting the sealed air chamber 2510 enter and exit through one of the electrochemical cells 2504, 2506. Accordingly, the sealed chamber 2510 is sealed in the sense that no ions enter or exit the sealed chamber 2510 without passing through one of the electrochemical cells 2504, 2506.

A sensor managing device 2526 includes any combination of hardware, software and/or firmware for managing the currents 2516, 2520 and measuring the cell voltage ($V_{CELL}$) 2528 across the electrochemical measuring cell 2504 to determine an ion concentration. The sensor managing device 2526, therefore, operates as discussed above except that sensor managing device 2526 also directs the appropriate compensation current 2520 through the electrochemical compensation cell 2506. The compensation cell current 2520 causes the ion flow 2524 that results in the same volume of ions to flow out from sealed chamber 2510 through the electrochemical compensation cell 2506 as the volume of ions flowing into the sealed chamber 2510 through the electrochemical measuring cell 2504 and the same number of ions to flow into the sealed chamber 2510 through the electrochemical compensation cell 2506 as the volume of ions flowing out from the sealed chamber 2510 through the electrochemical measuring cell 2504. In certain situations where the structure of the two cells 2504, 2506 is the same, the currents 2516, 2520 have equal magnitudes but opposite polarities. The sensor system 2500 may be implemented using any combination of hardware, software and firmware. Various functions and operations of the functional blocks described herein may be implemented in any number of devices, circuits or elements. Any of the functional blocks may be integrated in a single device and the functions of the blocks may be distributed over several devices, circuits and elements.

Figure 26:
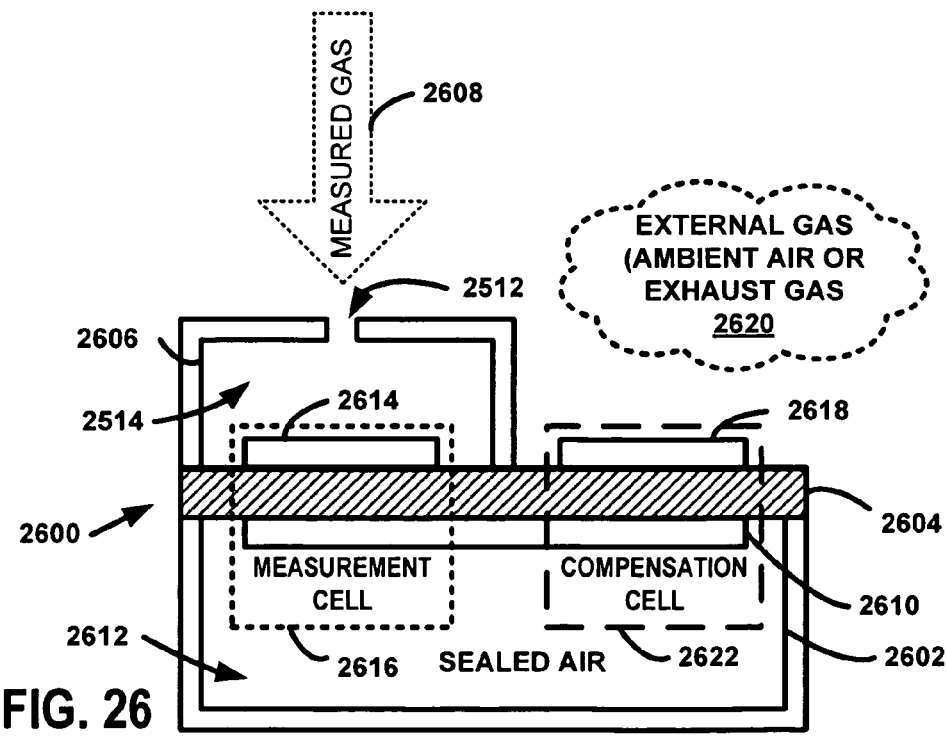
FIG. 26 is a block diagram of a cross section of an electrochemical sensor including a sealed air chamber for measuring exhaust gas.

FIG. 26 is a block diagram of a cross section of an electrochemical sensor 2600 including a sealed air chamber for measuring exhaust gas. The sensor 2600, therefore, is an example of the sensor 2502 of FIG. 25 where the measured fluid and external fluid are gases. For the example of FIG. 26, the sensor 2600 is a wideband single measuring cell sensor for measuring oxygen concentration within the exhaust system of a combustion engine. The sensor 2600 may also be used within other systems and for other uses in some situations.

The sensor 2600 includes a single laminated zirconium dioxide ($ZrO_2$) ceramic layer 2604. A space between the $ZrO_2$ layer 2604 and a chamber housing 2606 forms the measuring chamber 2514. A hole 2512 within the chamber housing 2606 forms a diffusion gap for receiving a measured gas 2608. The measured exhaust gas 2608, therefore, is an example of the measured fluid 2508. The hole 2512 may be a diffusion gap, diffusion layer, or other opening into the measuring chamber 2514.

A single platinum electrode (air electrode) 2610 is disposed on the $ZrO_2$ layer 2604 such that the air electrode 2510 is opposite the measuring chamber 2514 and exposed to sealed air 2612 within a sealed air chamber 2602. The sealed air chamber 2602 is an example of the sealed chamber 2510.

A second platinum electrode (measuring electrode) 2614 is disposed on the $ZrO_2$ layer 2604 opposite the air electrode 2610 and is exposed to the measured gas 2608 within the measuring chamber 2512 to form an oxygen electrochemical measuring cell 2616 with the air electrode 2610 and the $ZrO_2$ layer 2604. A third platinum electrode 2618 is disposed on the same side of $ZrO_2$ layer 2604 as the second platinum electrode 2614 and is positioned outside of the measuring chamber 2514 such that the third platinum electrode 2618 is exposed to an external gas 2620 which may be ambient air, exhaust gas or any other gas that includes adequate volume of oxygen ions. The third platinum electrode 2618 is a compensation electrode 2618 that forms a compensation electrochemical cell 2622 with the air electrode 2610 and the $ZrO_2$ layer 2604. Accordingly, the measuring electrode 2614, air electrode 2610, and $ZrO_2$ layer 2604 form the electrochemical oxygen measuring cell 2616 and the compensation electrode 2618, air electrode 2610, and $ZrO_2$ layer 2604 form the compensation electrochemical cell 2522.

An electrical current (measuring cell current) through the electrochemical oxygen measuring cell 2616 transports oxygen ions in an opposite direction to the direction of the electrical current. A compensation current with an opposite polarity to the measuring cell current is directed through the compensation cell which moves oxygen ions in a direction opposite the compensation cell current. The currents are selected such that the volume of oxygen ions pumped in to the measuring chamber by one of the cells is equal to the volume of oxygen ions pumped out from the measuring chamber by the other electrochemical cell. For example, where the compensation electrode 2618 has the same surface area as the measurement electrode 2614 and the electrochemical compensation cell 2622 has similar structure to the electrochemical oxygen measuring cell 2616, the compensation current is equal in magnitude to the measurement current, but opposite in polarity.

As mentioned above, the external gas 2620 must have an adequate volume of oxygen ions to allow the electrochemical compensation cell 2622 to pump the same volume of oxygen ions depleted from the sealed air chamber 2602 by the electrochemical oxygen measuring cell 2616. Accordingly, for the example of FIG. 26, the external gas 2620 may be exhaust gas, air, or other gas where there is adequate water, carbon dioxide, carbon monoxide or other compounds containing sufficient oxygen ions to supply the ion flow 2524.

The sealed air chamber 2602 ensures an adequate volume of ambient gas to minimize or eliminate the possibility of oxygen-depleted or oxygen-enriched gas being exposed to the air electrode 2610. In sensors where a single cell is exposed to ambient air through an opening, it may be possible for the opening to become obstructed and air flow restricted. For example, off-road vehicles are often exposes to dirt, dust, mud, and water and the sensor may come in contact with these contaminants or sometimes be submerged. Accordingly, an opening within a sensor opening may become obstructed. A sensor with a sealed chamber, however, does not require the air electrode to be exposed to ambient air directly. The compensation cell provides an interface to the outside air without using an opening.

Clearly, other embodiments and modifications of this invention will occur readily to those of ordinary skill in the art in view of these teachings. Therefore, this invention is to be limited only by following claims, which include all such embodiments, equivalents, and modifications when viewed in conjunction with the above specification and accompanying drawings.

What is claimed is:

1. A method comprising:
directing a primary pump current through a primary electrochemical cell system between a first constant primary pump current and a second constant primary pump current to direct a first ion flow into a shared measuring chamber and out from the shared measuring chamber;
detecting a first output signal generated by the primary electrochemical cell system in accordance with a first ion concentration within the shared measuring chamber;
detecting a second output signal generated by a secondary electrochemical cell system in accordance with a second ion concentration within the shared measuring chamber;
directing, based on a relationship between the first output signal and the second output signal, a secondary pump current through the secondary electrochemical cell system between a first constant secondary pump current and a second constant secondary pump current to direct a second ion flow into the shared measuring chamber and out from the shared measuring chamber.

2. A method in accordance with claim 1, wherein the first ion concentration and the second ion concentration are concentrations of an ion of an element, the first ion concentration within a first region of the shared measuring chamber and the second ion concentration within a second region within the shared measuring chamber.

3. A method in accordance with claim 2, wherein the second ion concentration is a ion concentration of an ion of an element of a compound that is reduced into the ion of the element and at least one other ion of another element at the secondary electrochemical cell system.

4. A method in accordance with claim 3, wherein the first ion concentration is a general oxygen ion concentration and the second ion concentration is a local oxygen ion concentration closer to an electrode than general oxygen ion concentration, the secondary electrochemical cell system comprising a nitrogen sensitive electrochemical cell having the electrode that reduces oxides of nitrogen into oxygen ions and nitrogen ions at the electrode.

5. A method in accordance with claim 1, wherein directing the primary current comprises directing the primary current through a pump cell of the first electrochemical cell system and wherein detecting the first output signal comprises detecting a measuring cell output signal of a measuring cell of the primary electrochemical cell system.

6. A method in accordance with claim 1, wherein directing the primary pump current comprises directing the primary pump current through a single electrochemical cell and wherein detecting the first output signal comprises detecting a single cell output signal of the single electrochemical cell.

7. A method in accordance with claim 3, further comprising:
directing the primary pump current in a positive direction at a first constant magnitude until the first output signal reaches an upper threshold;
directing the primary pump current in a negative direction at the first constant magnitude until the first output signal reaches a lower threshold;
directing the secondary pump current in a positive direction at a second constant magnitude until a first difference between the second output signal and the first output signal reaches a first difference threshold; and
directing the secondary pump current in a negative direction at the second constant magnitude until a second difference between the second output signal and the first output signal reaches a second threshold difference.

8. A method in accordance with claim 7, further comprising:
determining an ion concentration of the at least one other ion of another element.

9. A method in accordance with claim 8, wherein the determining the ion concentration comprises determining the ion concentration of the at least one other ion of another element based on a duty cycle of the secondary pump current.

10. A method of determining a concentration of oxides of nitrogen (NOx), the method comprising:
receiving, from an oxygen electrochemical cell, a first output signal corresponding to a first oxygen ion concentration within a shared measuring chamber;
varying a primary pump current through the oxygen electrochemical cell between a first constant primary pump current and second constant primary pump current;
receiving from a nitrogen sensitive electrochemical cell, a second output signal corresponding to a second oxygen ion concentration within the shared measuring chamber, the second oxygen ion concentration resulting from a reduction of NOx into nitrogen ions and oxygen ions;
varying a secondary pump current through the nitrogen sensitive electrochemical cell between a first constant secondary pump current and a second constant secondary pump current in accordance with a relationship between the first output signal and the second output signal; and
determining a NOx concentration based on a waveform of a signal in accordance with the secondary pump current.

11. A method in accordance with claim 10, wherein the varying the secondary pump current comprises:
directing the first constant secondary pump current through the nitrogen sensitive electrochemical cell until a difference between the first output signal and the second output signal reaches first threshold; and
directing the second constant secondary pump current through the nitrogen sensitive electrochemical cell until the difference between the first output signal and the second output signal reaches a second threshold.

12. A method in accordance with claim 11, wherein:
at least a portion of the first output signal is an oxygen cell Nernst voltage generated by the oxygen electrochemical cell in response to the first oxygen ion concentration; and
at least a portion of the second output signal is an nitrogen cell Nernst voltage generated by the nitrogen sensitive electrochemical cell in response to the second oxygen ion concentration.

13. A method in accordance with claim 1, wherein the shared measuring chamber is configured to permit unrestricted flow of ions throughout the shared measuring chamber.

14. A method in accordance with claim 1, wherein the shared measuring chamber is not divided by a diffusion gap.

15. A method in accordance with claim 1, further comprising operating an electronic circuit together with the primary electrochemical cell system and the secondary electrochemical cell system to form an oscillator having a varying pulse width ratio, a varying amplitude, and a varying frequency.

16. A method in accordance with claim 6, wherein the single electrochemical cell comprises a single pair of electrodes configured to perform functionality of the primary electrochemical cell system related to both pumping the first ion flow and detecting the first output signal.

17. A method in accordance with claim 10, wherein the shared measuring chamber is configured to permit unrestricted flow of ions throughout the shared measuring chamber.

18. A method in accordance with claim 10, wherein the shared measuring chamber is not divided by a diffusion gap.

19. A method in accordance with claim 10, further comprising operating an electronic circuit together with the oxygen electrochemical cell and the nitrogen sensitive electrochemical cell to form an oscillator having a varying pulse width ratio, a varying amplitude, and a varying frequency.

* * * * *